(12) United States Patent
Navia et al.

(10) Patent No.: US 11,419,921 B2
(45) Date of Patent: *Aug. 23, 2022

(54) METHODS OF TREATING NEUROLOGICAL DISORDERS

(71) Applicant: EnClear Therapies, Inc., Newburyport, MA (US)

(72) Inventors: Manuel A. Navia, Lexington, MA (US); Kasper Roet, Somerville, MA (US); Jonathan Fleming, Newton Lower Falls, MA (US)

(73) Assignee: EnClear Therapies, Inc., Newburyport, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/153,548

(22) Filed: Jan. 20, 2021

(65) Prior Publication Data

US 2021/0154276 A1     May 27, 2021

Related U.S. Application Data

(63) Continuation of application No. PCT/US2019/042880, filed on Jul. 22, 2019.

(60) Provisional application No. 62/815,115, filed on Mar. 7, 2019, provisional application No. 62/702,186, filed on Jul. 23, 2018.

(51) Int. Cl.
*A61P 25/28* (2006.01)
*G01N 33/53* (2006.01)
*A61K 38/48* (2006.01)

(52) U.S. Cl.
CPC ........ *A61K 38/4826* (2013.01); *A61K 38/486* (2013.01); *A61K 38/4833* (2013.01); *A61K 38/4846* (2013.01); *A61K 38/4853* (2013.01); *A61P 25/28* (2018.01)

(58) Field of Classification Search
None
See application file for complete search history.

(56) References Cited

U.S. PATENT DOCUMENTS 3,929,992 A   12/1975  Sehgal et al.
4,316,885 A    2/1982  Rakhit
(Continued)

FOREIGN PATENT DOCUMENTS

WO    98/02441 A2   1/1998
WO    99/15530 A1   4/1999
(Continued)

OTHER PUBLICATIONS

McRae et al., Mapping the active sites of bovine thrombin, factor IXa, factor Xa, factor XIa, factor XIIa, plasma kallikrein, and trypsin with amino acid and peptide thioesters: development of new sensitive substrates. Biochemistry 1981, 20, 25, 7196-7206 (Year: 1981).*

(Continued)

*Primary Examiner* — Aurora M Fontainhas
(74) *Attorney, Agent, or Firm* — Nutter McClennen & Fish LLP

(57) ABSTRACT

Disclosed is a method for treating a subject having a neurological disorder characterized by the presence of dipeptide repeat proteins comprising contacting the cerebrospinal fluid (CSF) of the subject with an agent capable of removing or degrading the toxic protein.

22 Claims, 18 Drawing Sheets
Specification includes a Sequence Listing.

(56) References Cited

U.S. PATENT DOCUMENTS

| | | |
|---|---|---|
| 4,366,241 A | 12/1982 | Tom et al. |
| 4,376,110 A | 3/1983 | David et al. |
| 4,382,445 A | 5/1983 | Sommers |
| 4,517,288 A | 5/1985 | Giegel et al. |
| 4,650,803 A | 3/1987 | Stella et al. |
| 4,655,745 A | 4/1987 | Corbett |
| 4,830,849 A | 5/1989 | Osterholm |
| 4,837,168 A | 6/1989 | de Jaeger et al. |
| 4,950,232 A | 8/1990 | Ruzicka et al. |
| 5,023,263 A | 6/1991 | Von Burg |
| 5,023,264 A | 6/1991 | Caufield et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,162,333 A | 11/1992 | Failli et al. |
| 5,177,203 A | 1/1993 | Failli et al. |
| 5,221,670 A | 6/1993 | Caufield |
| 5,233,036 A | 8/1993 | Hughes |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,405,316 A | 4/1995 | Magram |
| 5,411,967 A | 5/1995 | Kao et al. |
| 5,434,260 A | 7/1995 | Skotnicki et al. |
| 5,463,048 A | 10/1995 | Skotnicki et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,531,673 A | 7/1996 | Helenowski |
| 5,563,145 A | 10/1996 | Failli et al. |
| 5,665,772 A | 9/1997 | Cottens et al. |
| 5,780,462 A | 7/1998 | Lee et al. |
| 5,957,912 A | 9/1999 | Heitzmann |
| 6,193,691 B1 | 2/2001 | Beardsley |
| 6,210,346 B1 | 4/2001 | Hall et al. |
| 6,273,913 B1 | 8/2001 | Wright et al. |
| 6,277,983 B1 | 8/2001 | Shaw et al. |
| 6,358,969 B1 | 3/2002 | Shelley et al. |
| 6,471,960 B1 | 10/2002 | Anderson |
| 6,585,764 B2 | 7/2003 | Wright et al. |
| 6,599,275 B1 | 7/2003 | Fischer, Jr. |
| 6,670,168 B1 | 12/2003 | Katz et al. |
| 6,689,085 B1 | 2/2004 | Rubenstein et al. |
| 6,696,488 B2 | 2/2004 | Wolfe et al. |
| 6,808,536 B2 | 10/2004 | Wright et al. |
| 7,025,739 B2 | 4/2006 | Saul |
| 7,037,288 B2 | 5/2006 | Rosenberg et al. |
| 7,717,871 B2 | 5/2010 | Odland |
| 7,763,142 B2 | 7/2010 | Watson |
| 7,887,503 B2 | 2/2011 | Geiger |
| 8,206,334 B2 | 6/2012 | Kralick et al. |
| 8,216,173 B2 | 7/2012 | Dacey, Jr. et al. |
| 8,292,856 B2 | 10/2012 | Bertrand et al. |
| 8,435,204 B2 | 5/2013 | Lad et al. |
| 9,421,348 B2 | 8/2016 | Lenihan et al. |
| 9,603,792 B2 | 3/2017 | John |
| 9,629,987 B2 | 4/2017 | Anand et al. |
| 9,687,670 B2 | 6/2017 | Dacey, Jr. et al. |
| 9,744,338 B2 | 8/2017 | East et al. |
| 9,770,180 B2 | 9/2017 | Radojicic |
| 9,895,518 B2 | 2/2018 | Lad et al. |
| 9,919,138 B2 | 3/2018 | Lenihan et al. |
| 10,258,781 B2 | 4/2019 | Choi et al. |
| 10,272,188 B1 | 4/2019 | Geiger et al. |
| 2002/0025521 A1 | 2/2002 | Lu et al. |
| 2003/0135148 A1 | 7/2003 | Dextradeur et al. |
| 2004/0068241 A1 | 4/2004 | Fischer |
| 2004/0110250 A1 | 6/2004 | Wischik et al. |
| 2004/0138153 A1 | 7/2004 | Ramesh et al. |
| 2004/0220510 A1 | 11/2004 | Koullick et al. |
| 2004/0236309 A1 | 11/2004 | Yang |
| 2006/0025726 A1 | 2/2006 | Fischer et al. |
| 2006/0079740 A1 | 4/2006 | Silver et al. |
| 2007/0167867 A1 | 7/2007 | Wolf |
| 2007/0173787 A1 | 7/2007 | Huang et al. |
| 2007/0243179 A1 | 10/2007 | Elia |
| 2008/0082036 A1 | 4/2008 | Trescony et al. |
| 2008/0242590 A1 | 10/2008 | Andersson et al. |
| 2010/0030196 A1 | 2/2010 | Hildebrand et al. |
| 2010/0234792 A1 | 9/2010 | Dacey, Jr. et al. |
| 2011/0033463 A1 | 2/2011 | Thakker et al. |
| 2012/0238835 A1 | 9/2012 | Hyde et al. |
| 2012/0238936 A1 | 9/2012 | Hyde et al. |
| 2014/0018257 A1 | 1/2014 | Suga et al. |
| 2014/0206102 A1 | 7/2014 | Petrucelli et al. |
| 2014/0303455 A1 | 10/2014 | Shachar et al. |
| 2014/0377319 A1 | 12/2014 | Leuthardt et al. |
| 2015/0374898 A1 | 12/2015 | Fujieda et al. |
| 2016/0002627 A1 | 1/2016 | Bennett et al. |
| 2016/0025747 A1 | 1/2016 | Ranum et al. |
| 2016/0089521 A1 | 3/2016 | Dragoon et al. |
| 2016/0361365 A1 | 12/2016 | Lee et al. |
| 2017/0059586 A1 | 3/2017 | Petrucelli et al. |
| 2017/0157038 A1 | 6/2017 | Peyman |
| 2017/0157374 A1 | 6/2017 | Hedstrom et al. |
| 2017/0313687 A1 | 11/2017 | Hendrickson et al. |
| 2018/0028746 A1 | 2/2018 | Abrams et al. |
| 2018/0185058 A1 | 7/2018 | Anand et al. |
| 2018/0371010 A1 | 12/2018 | Vassylyev et al. |
| 2019/0009014 A1 | 1/2019 | Chen et al. |
| 2019/0048371 A1 | 2/2019 | Basheer et al. |
| 2019/0089521 A1 | 3/2019 | Coulthard et al. |
| 2019/0317099 A1 | 10/2019 | Halbert et al. |
| 2020/0046954 A1 | 2/2020 | Lad et al. |
| 2020/0330497 A1 | 10/2020 | Marcotulli et al. |
| 2021/0023293 A1 | 1/2021 | DePasqua et al. |
| 2021/0033620 A1 | 2/2021 | Porter et al. |
| 2021/0145944 A1 | 5/2021 | Navia et al. |

FOREIGN PATENT DOCUMENTS

| | | |
|---|---|---|
| WO | 2000/056335 A1 | 9/2000 |
| WO | 01/14387 A1 | 3/2001 |
| WO | 03/057218 A1 | 7/2003 |
| WO | 2003/015710 A3 | 2/2004 |
| WO | 2004/058337 A1 | 7/2004 |
| WO | 2004/091444 A2 | 10/2004 |
| WO | 2008/105959 A2 | 9/2008 |
| WO | 2011114260 A1 | 9/2011 |
| WO | 2014124365 A2 | 8/2014 |
| WO | 2014159247 A1 | 10/2014 |
| WO | 2015/049588 A2 | 4/2015 |
| WO | 2017096228 A1 | 6/2017 |
| WO | 2018005621 A1 | 1/2018 |
| WO | 2020/023417 A1 | 1/2020 |
| WO | 2020/023418 A1 | 1/2020 |

OTHER PUBLICATIONS

Lin et al., Facile synthesis of enzyme-inorganic hybrid nanoflowers and their application as an immobilized trypsin reactor for highly efficient protein digestion. (Communication) RSC Adv., 2014. 4, 13888-13891 (Year: 2014).*

Arai, T., et al., "TDP-43 is a component of ubiquitin-positive tau-negative inclusions in frontotemporal lobar degeneration and amyotrophic lateral sclerosis," Biochemical and Biophysical Research Communications, vol. 351, Issue 3, 2006, pp. 602-611.

(56) References Cited

OTHER PUBLICATIONS

Arai, T., et al., "Phosphorylated and cleaved TDP?43 in ALS, FTLD and other neurodegenerative disorders and in cellular models of TDP-43 proteinopathy," Neuropathology, vol. 30, 2010, pp. 170-181.
Andersen, P., et al., "Clinical genetics of amyotrophic lateral sclerosis: what do we really know?" Nature Reviews Neurology, vol. 7, 2011, pp. 603-615.
Brat, D., et al., "Tau-associated neuropathology in ganglion cell tumours increases with patient age but appears unrelated to ApoE genotype," Neuropathy and Applied Neurobiology, vol. 27, Issue 3, 2001, pp. 197-205.
Buee, L., et al., "Tau protein isoforms, phosphorylation and role in neurodegenerative disorders," Brain Research Reviews, vol. 33, Issue 1, 2000, pp. 95-130.
Chang, Y., et al., "The Glycine-Alanine Dipeptide Repeat from C9orf72 Hexanucleotide Expansions Forms Toxic Amyloids Possessing Cell-to-Cell Transmission Properties" Journal of Biological Chemistry, vol. 291, Issue 10, 2016, pp. 4903-4911.
Coatti, G., et al., "Pericytes Extended Survival of ALS SOD1 Mice and Induce the Expression of Antioxidant Enzymes in the Murine Model and in IPSCs Dervised Neuronal Cells from an ALS Patient," Stem Cell Reviews and Reports (2017) 13: 686-698.
De Souza, P., et al., "A biotechnology perspective of fungal proteases," Brazilian Journal of Microbiology, vol. 46, 2, 2015, pp. 337-346.
Diamond, S., "Methods for mapping protease specificity," Current Opinion in Chemical Biology, vol. 11, Issue 1, 2007, pp. 46-51.
Evidente, V., et al., "Post-encephalitic parkinsonism," Journal of Neurology, Neurosurgery & Psychiatry, vol. 63, Issue 1, 1998, pp. 5.
Grad, L., et al., "Prion-like activity of Cu/Zn superoxide dismutase: implications for amyotrophic lateral sclerosis," 8:1, 2014, pp. 33-41.
Giordana, M., et al., "Dementia and cognitive impairment in amyotrophic lateral sclerosis: a review," Neurological Sciences, vol. 32, 2011, pp. 9-16.
Hasegawa, M., et al., "Molecular Dissection of TDP-43 Proteinopathies," Journal of Molecular Neuroscience, vol. 45, 2011, pp. 480-485.
International Search Report and Written Opinion for International Application No. PCT/US2019/042880, dated Oct. 16, 2019 (10 pages).
International Search Report and Written Opinion for International Application No. PCT/US2019/042879, dated Oct. 8, 2019 (14 pages).
International Search Report and Written Opinion for International Application No. PCT/US2020/027683, dated Aug. 3, 2020 (19 pages).
International Preliminary Report on Patentability for International Application No. PCT/US2019/042880, dated Jan. 21, 2021 (8 pages).
Written Opinion of the International Preliminary Examining Authority for International Application No. PCT/US2019/042879, dated Feb. 25, 2021 (6 pages).
Written Opinion of the International Preliminary Examining Authority for International Application No. PCT/US2019/042880, dated Sep. 11, 2020 (8 pages).
Kaufman, S., et al., "Prion-Like Propagatio of Protein Aggregation and Related Therapeutic Strategies," Neurotherapeutics, 10, 2013, pp. 371-382.
Kopeikina, K., et al., "Soluble forms of tau are toxic in Alzheimer's disease," Translational Neuroscience 3(3), 2012, pp. 223-233.
Kouzehgarani, G., et al., "Harnessing cerebrospinal fluid circulation for drug delivery to brain tissues," Advanced Drug Delivery Reviews, 2021, vol. 173, pp. 20-59.
Lee, V., et al., "Neurodegenerative tauopathies," Annual Review of Neuroscience, vol. 24, 2001, pp. 1121-1159.
Lei, P., et al., "Tau protein: relevance to Parkinson's disease," The International Journal of Biochemistry & Cell Biology, vol. 42, Issue 11, 2010, pp. 1775-1778.

Martin, L., et al., "Post-translational modifications of tau protein: implications for Alzheimer's disease," Neurochemistry International, vol. 58, Issue 4, pp. 458-471.
May, S., et al., "C9orf72 FTLD/ALS-associated Gly-Ala dipeptide repeat proteins cause neuronal toxicity and Unc119 sequestration," Acta Neuropathologica, vol. 128, 2014, pp. 485-503.
McKee, A., et al., "The Neuropathology of Chronic Traumatic Encephalopathy," Brain Pathology 253), 2015, pp. 350-364.
Narasimhan, S., et al., "Pathological Tau Strains from Human Brains Recapitulate the Diversity of Tauopathies in Nontransgenic Mouse Brain," The Jorunal of Neuroscience, vol. 37, Issue 47, 2017, pp. 11406-11423.
Neumann, M., et al., "Ubiquitinated TDP-43 in frontotemporal lobar degeneration and amyotrophic lateral sclerosis," Science, vol. 314, 2006, pp. 130-133.
Ohki, Y., et al., "Glycine-alanine dipeptide repeat protein contributes to toxicity in a zebrafish model of C9orf72 associated neurodegeneration," Molecular Neurodegeneration (2017) 12:6, pp. 1-11.
Phukan, J., et al., "Cognitive impairment in amyotrophic lateral sclerosis," The Lancet Neurology, vol. 6, Issue 11, pp. 994-1003.
Renton, A., et al., "A Hexanucleotide Repeat Expansion in C9ORF72 Is the Cause of Chromosome 9p21-Linked ALS-FTD," Neuron, vol. 27, Issue 2, pp. 257-268.
Westergard, T., et al., "Cell-to-Cell Transmission of Dipeptide Repeat Proteins Linked to C9orf72-ALS/FTD," Cell Reports, vol. 17, Issue 3, 2016, pp. 645-652.
Wray, S., et al., "Direct analysis of tau from PSP brain identifies new phosphorylation sites and a major fragment of N-terminally cleaved tau containing four microtubule-binding repeats," Journal of Neurochemistry, vol. 105, 2008, pp. 2343-2352.
Wszolek, Z., et al., "Frontotemporal dementia and parkinsonism linked to chromosome 17 (FTDP-17)" Orphanet Journal of Rare Diseases, 2006, 1:30, pp. 1-9.
Zhang, Y., et al., "Aggregation-prone c9FTD/ALS poly(GA) RAN-translated proteins cause neurotoxicity by inducing ER stress," Acta Neuropathologica, vol. 128, 2014, pp. 504-524.
Abbott, N., et al., "The role of brain barriers in fluid movement in the CNS: is there a 'glymphatic' system?" Acta Neuropathologica vol. 135, 2018, pp. 387-407.
Allen, J., et al., "Abstract 3483: Modeling circulating tumor cells in the peripheral blood and CSF of breast cancer patients," Cancer Research vol. 73, Issue 8, 2013, abstract only.
Allen, J., et al., "Abstract 5565: Circulating tumor cells in the peripheral blood and cerebrospinal fluid of patients with central nervous system metastases," Cancer Research vol. 72, Issue 8, 2012, abstract only.
Bioline "Proteinase K" accessed from bioline.com on Jun. 22, 2021 (Year: 2013).
Finsterer, J., et al., "Liquorpheresis (CSF filtration) in familial amyotrophic lateral sclerosis," Spinal Cord, vol. 39, 1999, pp. 592-593.
Hersh, D., et al., "MR-guided transcranial focused ultrasound safely enhances interstitial dispersion of large polymeric nanoparticles in the living brain," PLOS ONE 13(2): e0192240, 2018, 19 pages.
International Search Report and Written Opinion for International Application No. PCT/US2021/013458, dated Jun. 9, 2021 (20 pages).
Indivero, V., "Technique filters cancer where chemo can't reach: A new therapy may help cancer patients with malignant cells near the spinal cord and in the brain," dated Jul. 30, 2013. Retrieved from the internet under https://news.psu.edu/story/282970/2013/07/30/research/technique-filters-cancer-where-chemo-cant-reach, 4 pages.
Jessen, N., et al., "The Glymphatic System—A Beginner's Guide," Neurochemical Research, 2015, 40(2), pp. 2583-2599.
Legon, W., et al., "Transcranial focused ultrasound modulates the activity of primary somatosensory cortex in humans," Nature Neuroscience vol. 17, No. 2, 2014, pp. 322-329.
Lipsman, N., et al., "Blood-brain barrier opening in Alzheimer's disease using MR-guided focused ultrasound," Nature Communications vol. 9, Article 2336, 2018, pp. 1-8.

(56) References Cited

OTHER PUBLICATIONS

Menendez-Gonzalez, M., et al., "Targeting Beta-Amyloid at the CSF: A New Therapeutic Strategy in Alzheimer's Disease," Frontiers in Aging Neuroscience, vol. 10, 2018, pp. 1-8.
Ozcelik, A., et al., "Acoustic tweezers for the life sciences," Nature Methods vol. 15, 2018, pp. 1021-1028.
Paraskevas, G., et al., "The emerging TDP-43 proteinpathy" Neuroimmunol Neuroinflammation 5:17 (Year 2018).
Pardridge, W., et al., "CSF, blood-brain barrier, and brain drug delivery," Expert Opinion on Drug Delivery, vol. 13, 2016, pp. 1-13.
Patel, A., et al., "Identification and enumeration of circulating tumor cells in the cerebrospinal fluid of breast cancer patents with central nervous system metastases," Oncotarget, vol. 2, No. 10, 2011, pp. 752-760.
Reinhard, M., et al., "Blood-Brain Barrier Disruption by Low-Frequency Ultrasound," Stroke, vol. 37, 2006, pp. 1546-1548.
Sonabend, A., et al., "Overcoming the Blood-Brain Barrier with an Implantable Ultrasound Device," Clinical Cancer Research, vol. 25, Issue 13, 2019, pp. 3750-3752.
Song, J., et al., "Investigation of standing wave formation in a human skull for a clinical prototype of a large-aperture, transcranial MR-guided Focused Ultrasound (MRgFUS) phased array: An experimental and simulation study," IEEE Transactions on Biomedical Engineering, vol. 59, Issue 2, 2012, pp. 435-444.
Takalo, M., et al., "Protein aggregation and degradation mechanisms in neurodegenerative diseases," American Journal of Neurodegenerative Disease, 2013; 2(1), pp. 1-14.
Tarasoff-Conway, J., et al., "Clearance systems in the brain implications for Alzheimer disease," Nature Reviews Neurology 11(8), 2015, pp. 457-470.
Tyler, W., et al., "Remote Excitation of Neuronal Circuits Using Low-Intensity, Low-Frequency Ultrasound," PLOS ONE vol. 3, Issue 10, 2008, e3511, 11 pages.
Xie, L., et al., "Sleep Drives Metabolite Clearance from the Adult Brain," Science vol. 342, Issue 6156, 2013, pp. 373-377.
Arriagada, P., et al., "Neurofibrillary tangles but not senile plaques parallel duration and severity of Alzheimer's disease," Neurology 42, 1992, pp. 631-639.
Asai, D., et al., "Chapter 3 Making Monoclonal Antibodies," Methods in Cell Biology, vol. 37, 1993, pp. 57-74.
Dejesus-Hernandez, M., et al., "Expanded GGGGCC Hexanucleotide Repeat in Noncoding Region of C9ORF72 Causes Chromosome 9p-Linked FTD and ALS," Neuron, vol. 72, 2011, pp. 245-256.
Giannakopoulos, P., et al., Tangle and neuron numbers, but not amyloid load, predict cognitive status in Alzheimer's disease, Neurology, vol. 60, 2003, pp. 1495-1500.
Gomez-Isla, T., et al., Neuronal loss correlates with but exceeds neurofibrillary tangles in Alzheimer's disease, Annals of Neurology, vol. 41, 1997, pp. 17-24.
Graff-Radford, N., et al., "Frontotemporal dementia," Seminars in Neurology vol. 27, 2007, pp. 48-57.
Hasegawa, M., et al., "Phosphorylated TDP-43 in frontotemporal lobar degeneration and amyotrophic lateral sclerosis," Annals of Neurology, vol. 62, Issue 1, 2008, pp. 60-70.
Lomen-Hoerth, C., et al., "The overlap of amyotrophic lateral sclerosis and frontotemporal dementia," Neurology, vol. 59, 2002, pp. 1077-1079.
Marx, S., et al., "Bench to Bedside: The Development of Rapamycin and Its Application to Stent Restenosis", Journal of the American Heart Association 104, 2001, pp. 852-855.
Paulson, H., et al., "Genetics of Dementia," Seminars in Neurology, vol. 31, 2011, pp. 449-460.
Poreba, M., et al., "Current Strategies for Probing Substrate Specificity of Proteases," Current Medicinal Chemistry, vol. 17, Issue 33, 2010, pp. 3968-3995.
Quinn, J., et al., "Tau Proteolysis in the Pathogenesis of Tauopathies: Neurotoxic Fragments and Novel Biomarkers," Journal of Alzheimer's Disease, vol. 63, No. 1, 2018, pp. 13-33.
Steele, J., et al., "Progressive Supranuclear Palsy A Heterogeneous Degeneration Involving the Brain Stem, Basal Ganglia and Cerebellum With Vertical Gaze and Pseudobulbar Palsy, Nuchal Dystonia and Dementia," Arch Neurol. vol. 10, No. 4, 1964, pp. 333-359.
International Preliminary Report on Patentability for International Application No. PCT/US2019/042879, dated May 18, 2021 (6 pages).
International Preliminary Report on Patentability for International Application No. PCT/US2020/027683, dated Oct. 21, 2021 (11 pages).
Extended European Search Report for European Application No. 19840444.4 dated Jun. 28, 2022, 7 pages.
Mori, K., et al., "The C9orf72 GGGGCC repeat is translated into aggregating dipeptide-repeat proteins in FTLD/ALS," Science, vol. 339, No. 6125, Feb. 7, 2013, pp. 1335-1338.

\* cited by examiner

SEQUENCE LISTING

<160> NUMBER OF SEQ ID NOS: 13

<210> SEQ ID NO 1
<211> LENGTH: 224
<212> TYPE: PRT
<213> ORGANISM: Bos taurus

<400> SEQUENCE: 1

```
Ile Val Gly Gly Tyr Thr Cys Ala Glu Asn Ser Val Pro Tyr Gln Val
1               5                   10                  15

Ser Leu Asn Ala Gly Tyr His Phe Cys Gly Gly Ser Leu Ile Asn Asp
                20                  25                  30

Gln Trp Val Val Ser Ala Ala His Cys Tyr Gln Tyr His Ile Gln Val
            35                  40                  45

Arg Leu Gly Glu Tyr Asn Ile Asp Val Leu Glu Gly Gly Glu Gln Phe
        50                  55                  60

Ile Asp Ala Ser Lys Ile Ile Arg His Pro Lys Tyr Ser Ser Trp Thr
65                  70                  75                  80

Leu Asp Asn Asp Ile Leu Leu Ile Lys Leu Ser Thr Pro Ala Val Ile
                85                  90                  95

Asn Ala Arg Val Ser Thr Leu Leu Leu Pro Ser Ala Cys Ala Ser Ala
                100                 105                 110

Gly Thr Glu Cys Leu Ile Ser Gly Trp Gly Asn Thr Leu Ser Ser Gly
            115                 120                 125

Val Asn Tyr Pro Asp Leu Leu Gln Cys Leu Val Ala Pro Leu Leu Ser
        130                 135                 140

His Ala Asp Cys Glu Ala Ser Tyr Pro Gly Gln Ile Thr Asn Asn Met
145                 150                 155                 160

Ile Cys Ala Gly Phe Leu Glu Gly Gly Lys Asp Ser Cys Gln Gly Asp
                165                 170                 175

Ser Gly Gly Pro Val Ala Cys Asn Gly Gln Leu Gln Gly Ile Val Ser
                180                 185                 190

Trp Gly Tyr Gly Cys Ala Gln Lys Gly Lys Pro Gly Val Tyr Thr Lys
        195                 200                 205

Val Cys Asn Tyr Val Asp Trp Ile Gln Glu Thr Ile Ala Ala Asn Ser
        210                 215                 220
```

<210> SEQ ID NO 2
<211> LENGTH: 224
<212> TYPE: PRT
<213> ORGANISM: Homo sapiens

<400> SEQUENCE: 2

```
Ile Val Gly Gly Tyr Thr Cys Glu Glu Asn Ser Val Pro Tyr Gln Val
1               5                   10                  15

Ser Leu Asn Ser Gly Ser His Phe Cys Gly Gly Ser Leu Ile Ser Glu
                20                  25                  30

Gln Trp Val Val Ser Ala Gly His Cys Tyr Lys Pro His Ile Gln Val
            35                  40                  45

Arg Leu Gly Glu His Asn Ile Glu Val Leu Glu Gly Asn Glu Gln Phe
        50                  55                  60

Ile Asn Ala Ala Lys Ile Ile Arg His Pro Lys Tyr Asn Arg Ile Thr
65                  70                  75                  80

Leu Asn Asn Asp Ile Met Leu Ile Lys Leu Ser Thr Pro Ala Val Ile
                85                  90                  95
```

```
Asn Ala His Val Ser Thr Ile Ser Leu Pro Thr Ala Pro Pro Ala Ala
            100                 105                 110

Gly Thr Glu Cys Leu Ile Ser Gly Trp Gly Asn Thr Leu Ser Ser Gly
            115                 120                 125

Ala Asp Tyr Pro Asp Glu Leu Gln Cys Leu Asp Ala Pro Val Leu Thr
130                 135                 140

Gln Ala Lys Cys Lys Ala Ser Tyr Pro Leu Lys Ile Thr Ser Lys Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Ile Val Ser
            180                 185                 190

Trp Gly Tyr Gly Cys Ala Gln Lys Arg Arg Pro Gly Val Tyr Thr Lys
            195                 200                 205

Val Tyr Asn Tyr Val Asp Trp Ile Lys Asp Thr Ile Ala Ala Asn Ser
            210                 215                 220

<210> SEQ ID NO 3
<211> LENGTH: 224
<212> TYPE: PRT
<213> ORGANISM: Homo sapiens

<400> SEQUENCE: 3

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Gln Tyr Asp Arg Lys Thr
65                  70                  75                  80

Leu Asp Asn Asp Ile Leu Leu Ile Lys Leu Ser Ser Pro Ala Val Ile
                85                  90                  95

Asn Ser Arg Val Ser Ala Ile Ser Leu Pro Thr Ala Pro Pro Ala Ala
            100                 105                 110

Gly Thr Glu Ser Leu Ile Ser Gly Trp Gly Asn Thr Leu Ser Ser Gly
            115                 120                 125

Ala Asp Tyr Pro Asp Glu Leu Gln Cys Leu Asp Ala Pro Val Leu Ser
130                 135                 140

Gln Ala Glu Cys Glu Ala Ser Tyr Pro Gly Lys Ile Thr Asn Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Ser Asn Gly Glu Leu Gln Gly Ile Val Ser
            180                 185                 190

Trp Gly Tyr Gly Cys Ala Gln Lys Asn Arg Pro Gly Val Tyr Thr Lys
            195                 200                 205

Val Tyr Asn Tyr Val Asp Trp Ile Lys Asp Thr Ile Ala Ala Asn Ser
            210                 215                 220

<210> SEQ ID NO 4
<211> LENGTH: 240
<212> TYPE: PRT
```

<213> ORGANISM: Sus scrofa

<400> SEQUENCE: 4

Val Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
            20                  25                  30

Thr Leu Ile Arg Gln Asn Trp Val Met Thr Ala Ala His Cys Val Asp
        35                  40                  45

Arg Glu Leu Thr Phe Arg Val Val Gly Glu His Asn Leu Asn Gln
    50                  55                  60

Asn Asn Gly Thr Glu Gln Tyr Val Gly Val Gln Lys Ile Val Val His
65                  70                  75                  80

Pro Tyr Trp Asn Thr Asp Asp Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Arg Ala Gly Thr Ile Leu Ala Asn Asn Ser Pro Cys Tyr
        115                 120                 125

Ile Thr Gly Trp Gly Leu Thr Arg Thr Asn Gly Gln Leu Ala Gln Thr
130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Gln Tyr Ala Val His Gly Val Thr Ser Phe
        195                 200                 205

Val Ser Arg Leu Gly Cys Asn Val Thr Arg Lys Pro Thr Val Phe Thr
    210                 215                 220

Arg Val Ser Ala Tyr Ile Ser Trp Ile Asn Asn Val Ile Ala Ser Asn
225                 230                 235                 240

<210> SEQ ID NO 5
<211> LENGTH: 240
<212> TYPE: PRT
<213> ORGANISM: Homo sapiens

<400> SEQUENCE: 5

Val Val Gly Gly Thr Glu Ala Gly Arg Asn Ser Trp Pro Ser Gln Ile
1               5                   10                  15

Ser Leu Gln Tyr Arg Ser Gly Gly Ser Arg Tyr His Thr Cys Gly Gly
            20                  25                  30

Thr Leu Ile Arg Gln Asn Trp Val Met Thr Ala Ala His Cys Val Asp
        35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

-continued

```
Val Leu Pro Gln Glu Gly Ala Ile Leu Ala Asn Asn Ser Pro Cys Tyr
        115                 120                 125

Ile Thr Gly Trp Gly Lys Thr Lys Thr Asn Gly Gln Leu Ala Gln Thr
    130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Lys Tyr Ser Val His Gly Val Thr Ser Phe
        195                 200                 205

Val Ser Ser Arg Gly Cys Asn Val Ser Arg Lys Pro Thr Val Phe Thr
    210                 215                 220

Gln Val Ser Ala Tyr Ile Ser Trp Ile Asn Asn Val Ile Ala Ser Asn
225                 230                 235                 240

<210> SEQ ID NO 6
<211> LENGTH: 241
<212> TYPE: PRT
<213> ORGANISM: Homo sapiens

<400> SEQUENCE: 6

Val Val Gly Gly Glu Glu Ala Arg Pro Asn Ser Trp Pro Trp Gln Val
1               5                   10                  15

Ser Leu Gln Tyr Ser Ser Asn Gly Lys Trp Tyr His Thr Cys Gly Gly
            20                  25                  30

Ser Leu Ile Ala Asn Ser Trp Val Leu Thr Ala Ala His Cys Ile Ser
        35                  40                  45

Ser Ser Arg Thr Tyr Arg Val Gly Leu Gly Arg His Asn Leu Tyr Val
    50                  55                  60

Ala Glu Ser Gly Ser Leu Ala Val Ser Val Ser Lys Ile Val Val His
65                  70                  75                  80

Lys Asp Trp Asn Ser Asn Gln Ile Ser Lys Gly Asn Asp Ile Ala Leu
                85                  90                  95

Leu Lys Leu Ala Asn Pro Val Ser Leu Thr Asp Lys Ile Gln Leu Ala
            100                 105                 110

Cys Leu Pro Pro Ala Gly Thr Ile Leu Pro Asn Asn Tyr Pro Cys Tyr
        115                 120                 125

Val Thr Gly Trp Gly Arg Leu Gln Thr Asn Gly Ala Val Pro Asp Val
    130                 135                 140

Leu Gln Gln Gly Arg Leu Leu Val Val Asp Tyr Ala Thr Cys Ser Ser
145                 150                 155                 160

Ser Ala Trp Trp Gly Ser Ser Val Lys Thr Ser Met Ile Cys Ala Gly
                165                 170                 175

Gly Asp Gly Val Ile Ser Ser Cys Asn Gly Asp Ser Gly Gly Pro Leu
            180                 185                 190

Asn Cys Gln Ala Ser Asp Gly Arg Trp Gln Val His Gly Ile Val Ser
        195                 200                 205

Phe Gly Ser Arg Leu Gly Cys Asn Tyr Tyr His Lys Pro Ser Val Phe
    210                 215                 220

Thr Arg Val Ser Asn Tyr Ile Asp Trp Ile Asn Ser Val Ile Ala Asn
225                 230                 235                 240

Asn
```

<210> SEQ ID NO 7
<211> LENGTH: 241
<212> TYPE: PRT
<213> ORGANISM: Homo sapiens

<400> SEQUENCE: 7

Met Leu Gly Gly Glu Ala Arg Pro Asn Ser Trp Pro Trp Gln Val
1               5                   10                  15

Ser Leu Gln Tyr Ser Ser Asn Gly Gln Trp Tyr His Thr Cys Gly Gly
                20                  25                  30

Ser Leu Ile Ala Asn Ser Trp Val Leu Thr Ala Ala His Cys Ile Ser
            35                  40                  45

Ser Ser Gly Ile Tyr Arg Val Met Leu Gly Gln His Asn Leu Tyr Val
    50                  55                  60

Ala Glu Ser Gly Ser Leu Ala Val Ser Val Ser Lys Ile Val Val His
65                  70                  75                  80

Lys Asp Trp Asn Ser Asp Gln Val Ser Lys Gly Asn Asp Ile Ala Leu
                85                  90                  95

Leu Lys Leu Ala Asn Pro Val Ser Leu Thr Asp Lys Ile Gln Leu Ala
            100                 105                 110

Cys Leu Pro Pro Ala Gly Thr Ile Leu Pro Asn Asn Tyr Pro Cys Tyr
            115                 120                 125

Val Thr Gly Trp Gly Arg Leu Gln Thr Asn Gly Ala Leu Pro Asp Asp
            130                 135                 140

Leu Lys Gln Gly Gln Leu Leu Val Val Asp Tyr Ala Thr Cys Ser Ser
145                 150                 155                 160

Ser Gly Trp Trp Gly Ser Thr Val Lys Thr Asn Met Ile Cys Ala Gly
                165                 170                 175

Gly Asp Gly Val Ile Cys Thr Cys Asn Gly Asp Ser Gly Gly Pro Leu
            180                 185                 190

Asn Cys Gln Ala Ser Asp Gly Arg Trp Glu Val His Gly Ile Gly Ser
            195                 200                 205

Leu Thr Ser Val Leu Gly Cys Asn Tyr Tyr Lys Pro Ser Ile Phe
    210                 215                 220

Thr Arg Val Ser Asn Tyr Asn Asp Trp Ile Asn Ser Val Ile Ala Asn
225                 230                 235                 240

Asn

<210> SEQ ID NO 8
<211> LENGTH: 242
<212> TYPE: PRT
<213> ORGANISM: Homo sapiens

<400> SEQUENCE: 8

Val Val His Gly Glu Asp Ala Val Pro Tyr Ser Trp Pro Trp Gln Val
1               5                   10                  15

Ser Leu Gln Tyr Glu Lys Ser Gly Ser Phe Tyr His Thr Cys Gly Gly
                20                  25                  30

Ser Leu Ile Ala Pro Asp Trp Val Val Thr Ala Gly His Cys Ile Ser
            35                  40                  45

Arg Asp Leu Thr Tyr Gln Val Val Leu Gly Glu Tyr Asn Leu Ala Val
    50                  55                  60

Lys Glu Gly Pro Glu Gln Val Ile Pro Ile Asn Ser Glu Glu Leu Phe
65                  70                  75                  80

```
Val His Pro Leu Trp Asn Arg Ser Cys Val Ala Cys Gly Asn Asp Ile
            85                  90                  95
Ala Leu Ile Lys Leu Ser Arg Ser Ala Gln Leu Gly Asp Ala Val Gln
            100                 105                 110
Leu Ala Ser Leu Pro Pro Ala Gly Asp Ile Leu Pro Asn Lys Thr Pro
            115                 120                 125
Cys Tyr Ile Thr Gly Trp Gly Arg Leu Tyr Thr Asn Gly Pro Leu Pro
            130                 135                 140
Asp Lys Leu Gln Gln Ala Arg Leu Pro Val Val Asp Tyr Lys His Cys
145                 150                 155                 160
Ser Arg Trp Asn Trp Trp Gly Ser Thr Val Lys Lys Thr Met Val Cys
            165                 170                 175
Ala Gly Gly Tyr Ile Arg Ser Gly Cys Asn Gly Asp Ser Gly Gly Pro
            180                 185                 190
Leu Asn Cys Pro Thr Glu Asp Gly Gly Trp Gln Val His Gly Val Thr
            195                 200                 205
Ser Phe Val Ser Ala Phe Gly Cys Asn Phe Ile Trp Lys Pro Thr Val
            210                 215                 220
Phe Thr Arg Val Ser Ala Phe Ile Asp Trp Ile Glu Glu Thr Ile Ala
225                 230                 235                 240

Ser His

<210> SEQ ID NO 9
<211> LENGTH: 242
<212> TYPE: PRT
<213> ORGANISM: Homo sapiens

<400> SEQUENCE: 9

Val Val Asn Gly Glu Asp Ala Val Pro Tyr Ser Trp Pro Trp Gln Val
1               5                   10                  15
Ser Leu Gln Tyr Glu Lys Ser Gly Ser Phe Tyr His Thr Cys Gly Gly
            20                  25                  30
Ser Leu Ile Ala Pro Asp Trp Val Val Thr Ala Gly His Cys Ile Ser
            35                  40                  45
Ser Ser Arg Thr Tyr Gln Val Val Leu Gly Glu Tyr Asp Arg Ala Val
            50                  55                  60
Lys Glu Gly Pro Glu Gln Val Ile Pro Ile Asn Ser Gly Asp Leu Phe
65                  70                  75                  80
Val His Pro Leu Trp Asn Arg Ser Cys Val Ala Cys Gly Asn Asp Ile
            85                  90                  95
Ala Leu Ile Lys Leu Ser Arg Ser Ala Gln Leu Gly Asp Ala Val Gln
            100                 105                 110
Leu Ala Ser Leu Pro Pro Ala Gly Asp Ile Leu Pro Asn Glu Thr Pro
            115                 120                 125
Cys Tyr Ile Thr Gly Trp Gly Arg Leu Tyr Thr Asn Gly Pro Leu Pro
            130                 135                 140
Asp Lys Leu Gln Glu Ala Leu Leu Pro Val Val Asp Tyr Glu His Cys
145                 150                 155                 160
Ser Arg Trp Asn Trp Trp Gly Ser Ser Val Lys Lys Thr Met Val Cys
            165                 170                 175
Ala Gly Gly Asp Ile Arg Ser Gly Cys Asn Gly Asp Ser Gly Gly Pro
            180                 185                 190
Leu Asn Cys Pro Thr Glu Asp Gly Gly Trp Gln Val His Gly Val Thr
            195                 200                 205
```

Ser Phe Val Ser Ala Phe Gly Cys Asn Thr Arg Arg Lys Pro Thr Val
210                 215                 220

Phe Thr Arg Val Ser Ala Phe Ile Asp Trp Ile Glu Glu Thr Ile Ala
225                 230                 235                 240

Ser His

<210> SEQ ID NO 10
<211> LENGTH: 98
<212> TYPE: PRT
<213> ORGANISM: Homo sapiens

<400> SEQUENCE: 10

Gly Pro Ile Pro Glu Val Leu Lys Asn Tyr Met Asp Ala Gln Tyr Tyr
1               5                   10                  15

Gly Glu Ile Gly Ile Gly Thr Pro Pro Gln Cys Phe Thr Val Val Phe
                20                  25                  30

Asp Thr Gly Ser Ser Asn Leu Trp Val Pro Ser Ile His Cys Lys Leu
            35                  40                  45

Leu Asp Ile Ala Cys Trp Ile His His Lys Tyr Asn Ser Asp Lys Ser
50                  55                  60

Ser Thr Tyr Val Lys Asn Gly Thr Ser Phe Asp Ile His Tyr Gly Ser
65                  70                  75                  80

Gly Ser Leu Ser Gly Tyr Leu Ser Gln Asp Thr Val Ser Val Pro Cys
                85                  90                  95

Gln Ser

<210> SEQ ID NO 11
<211> LENGTH: 244
<212> TYPE: PRT
<213> ORGANISM: Homo sapiens

<400> SEQUENCE: 11

Leu Gly Gly Val Lys Val Glu Arg Gln Val Phe Gly Glu Ala Thr Lys
1               5                   10                  15

Gln Pro Gly Ile Thr Phe Ile Ala Ala Lys Phe Asp Gly Ile Leu Gly
                20                  25                  30

Met Ala Tyr Pro Arg Ile Ser Val Asn Asn Val Leu Pro Val Phe Asp
            35                  40                  45

Asn Leu Met Gln Gln Lys Leu Val Asp Gln Asn Ile Phe Ser Phe Tyr
50                  55                  60

Leu Ser Arg Asp Pro Asp Ala Gln Pro Gly Gly Glu Leu Met Leu Gly
65                  70                  75                  80

Gly Thr Asp Ser Lys Tyr Tyr Lys Gly Ser Leu Ser Tyr Leu Asn Val
                85                  90                  95

Thr Arg Lys Ala Tyr Trp Gln Val His Leu Asp Gln Val Glu Val Ala
            100                 105                 110

Ser Gly Leu Thr Leu Cys Lys Glu Gly Cys Glu Ala Ile Val Asp Thr
            115                 120                 125

Gly Thr Ser Leu Met Val Gly Pro Val Asp Glu Val Arg Glu Leu Gln
            130                 135                 140

Lys Ala Ile Gly Ala Val Pro Leu Ile Gln Gly Glu Tyr Met Ile Pro
145                 150                 155                 160

Cys Glu Lys Val Ser Thr Leu Pro Ala Ile Thr Leu Lys Leu Gly Gly
                165                 170                 175

Lys Gly Tyr Lys Leu Ser Pro Glu Asp Tyr Thr Leu Lys Val Ser Gln
            180                 185                 190

```
Ala Gly Lys Thr Leu Cys Leu Ser Gly Phe Met Gly Met Asp Ile Pro
        195                 200                 205

Pro Pro Ser Gly Pro Leu Trp Ile Leu Gly Asp Val Phe Ile Gly Arg
210                 215                 220

Tyr Tyr Thr Val Phe Asp Arg Asp Asn Arg Val Gly Phe Ala Glu
225                 230                 235                 240

Ala Ala Arg Leu

<210> SEQ ID NO 12
<211> LENGTH: 271
<212> TYPE: PRT
<213> ORGANISM: Homo sapiens

<400> SEQUENCE: 12

Val Thr Glu His Val Leu Ala Asn Asn Asp Val Ser Cys Asp His Pro
1               5                   10                  15

Ser Asn Thr Val Pro Ser Gly Ser Asn Gln Asp Leu Gly Ala Gly Ala
                20                  25                  30

Gly Glu Asp Ala Arg Ser Asp Asp Ser Ser Arg Ile Ile Asn Gly
        35                  40                  45

Ser Asp Cys Asp Met His Thr Gln Pro Trp Gln Ala Ala Leu Leu Leu
50                  55                  60

Arg Pro Asn Gln Leu Tyr Cys Gly Ala Val Leu Val His Pro Gln Trp
65                  70                  75                  80

Leu Leu Thr Ala Ala His Cys Arg Lys Lys Val Phe Arg Val Arg Leu
                85                  90                  95

Gly His Tyr Ser Leu Ser Pro Val Tyr Glu Ser Gly Gln Gln Met Phe
            100                 105                 110

Gln Gly Val Lys Ser Ile Pro His Pro Gly Tyr Ser His Pro Gly His
            115                 120                 125

Ser Asn Asp Leu Met Leu Ile Lys Leu Asn Arg Arg Ile Arg Pro Thr
130                 135                 140

Lys Asp Val Arg Pro Ile Asn Val Ser Ser His Cys Pro Ser Ala Gly
145                 150                 155                 160

Thr Lys Cys Leu Val Ser Gly Trp Gly Thr Thr Lys Ser Pro Gln Val
                165                 170                 175

His Phe Pro Lys Val Leu Gln Cys Leu Asn Ile Ser Val Leu Ser Gln
            180                 185                 190

Lys Arg Cys Glu Asp Ala Tyr Pro Arg Gln Ile Asp Asp Thr Met Phe
            195                 200                 205

Cys Ala Gly Asp Lys Ala Gly Arg Asp Ser Cys Gln Gly Asp Ser Gly
            210                 215                 220

Gly Pro Val Val Cys Asn Gly Ser Leu Gln Gly Leu Val Ser Trp Gly
225                 230                 235                 240

Asp Tyr Pro Cys Ala Arg Pro Asn Arg Pro Gly Val Tyr Thr Asn Leu
                245                 250                 255

Cys Lys Phe Thr Lys Trp Ile Gln Glu Thr Ile Gln Ala Asn Ser
            260                 265                 270

<210> SEQ ID NO 13
<211> LENGTH: 223
<212> TYPE: PRT
<213> ORGANISM: Homo sapiens
```

```
<400> SEQUENCE: 13

Leu Val His Gly Gly Pro Cys Asp Lys Thr Ser His Pro Tyr Gln Ala
1               5                   10                  15

Ala Leu Tyr Thr Ser Gly His Leu Leu Cys Gly Gly Val Leu Ile His
            20                  25                  30

Pro Leu Trp Val Leu Thr Ala Ala His Cys Lys Lys Pro Asn Leu Gln
            35                  40                  45

Val Phe Leu Gly Lys His Asn Leu Arg Gln Arg Glu Ser Ser Gln Glu
        50                  55                  60

Gln Ser Ser Val Val Arg Ala Val Ile His Pro Asp Tyr Asp Ala Ala
65                  70                  75                  80

Ser His Asp Gln Asp Ile Met Leu Leu Arg Leu Ala Arg Pro Ala Lys
                85                  90                  95

Leu Ser Glu Leu Ile Gln Pro Leu Pro Leu Glu Arg Asp Cys Ser Ala
                100                 105                 110

Asn Thr Thr Ser Cys His Ile Leu Gly Trp Gly Lys Thr Ala Asp Gly
            115                 120                 125

Asp Phe Pro Asp Thr Ile Gln Cys Ala Tyr Ile His Leu Val Ser Arg
        130                 135                 140

Glu Glu Cys Glu His Ala Tyr Pro Gly Gln Ile Thr Gln Asn Met Leu
145                 150                 155                 160

Cys Ala Gly Asp Glu Lys Tyr Gly Lys Asp Ser Cys Gln Gly Asp Ser
                165                 170                 175

Gly Gly Pro Leu Val Cys Gly Asp His Leu Arg Gly Leu Val Ser Trp
            180                 185                 190

Gly Asn Ile Pro Cys Gly Ser Lys Glu Lys Pro Gly Val Tyr Thr Asn
        195                 200                 205

Val Cys Arg Tyr Thr Asn Trp Ile Gln Lys Thr Ile Gln Ala Lys
210                 215                 220
```

METHODS OF TREATING NEUROLOGICAL DISORDERS

CROSS-REFERENCE TO RELATED APPLICATIONS

This application is a continuation of International Patent Application No. PCT/US19/42880, filed on Jul. 22, 2019, which claims the benefit of and priority to U.S. Provisional Application Nos. 62/702,186, filed Jul. 23, 2018; and 62/815,115, filed Mar. 7, 2019, the disclosure of each of which is hereby incorporated by reference in its entirety for all purposes.

SEQUENCE LISTING

The instant application contains a Sequence Listing which has been submitted electronically in ASCII format and is hereby incorporated by reference in its entirety. The ASCII copy, created on Jul. 22, 2019, is named 120902-10202_ST25.txt and is 26 kb in size.

FIELD OF THE INVENTION

The invention relates generally to a method for treating a subject having a neurological disorder characterized by the presence of a dipeptide repeat protein, the method comprising contacting the cerebrospinal fluid (CSF) of the subject with an agent capable of removing or degrading the dipeptide repeat protein.

BACKGROUND

Amyotrophic lateral sclerosis (ALS) and frontotemporal lobar degeneration (FTLD) (including frontotemporal dementia (FTD)) are progressive, terminal neurological diseases. ALS affects 2 in 100,000 people and has historically been characterized by the degeneration of motor neurons in the brain and spinal cord, leading to progressive spasticity, muscle weakness and wasting and ultimately death due to respiratory failure, typically within three years from symptom onset. More recently, ALS has been increasingly recognized as a multisystem disorder with impairment of frontotemporal functions such as cognition and behavior in up to 50% of patients (Giordana et al., *Neurol. Sci.,* 2001 32, 9-16; Lomen-Hoerth et al., *Neurology,* 2003, 59, 1077-1079; and Phukan et al., *Lancet Neurol.,* 2007, 6, 994-1003).

Frontotemporal lobar degeneration (FTLD), is the second most common cause of presenile dementia, characterized by the degeneration of the frontal and temporal lobes of the brain, resulting in progressive changes in personality and behavior accompanied by language dysfunction, but with relative preservation of perception and memory (Graff-Radford and Woodruf, *Neurol.* 2007, 27, 48-57).

Both diseases are etiologically complex, and environmental factors, in addition to genetic factors, are likely to contribute to their onset (Andersen and Al-Chalabi, *Nat. Rev. Neurol.* 2011, 7, 603-615; Paulson and Igo, *Semin Neurol.,* 2011, 31, 449-360).

Approximately one in ten ALS patients and about half of the FTD patients have a family history of one or both of the diseases (ALS-FTD), but until relatively recently, little was known about the genes that could explain these familial forms of the diseases. Two independent studies published in 2011 identified hexanucleotide GGGGCC repeat expansions in the non-coding region of chromosome 9 open reading frame 72 gene (C9orf72) in two distinct families with a positive history of ALS-FTD. (DeJesus-Hernandez et al. *Neuron,* 2011, 72, 245-256; Renton et al. *Neuron,* 2011, 72, 257-268). RNA transcripts containing these expansions undergo repeat associated non-ATG (RAN) translation to form five dipeptide repeat proteins (GA, GP, GR, AP, and PR) which have been shown to cause neurodegeneration when expressed in vitro in neuronal cultures and in vivo in animal models (Westergard et al., *Cell Rep.* 2016, 17, 645-652).

SUMMARY

One aspect of the invention provides a method for treating a neurological disorder characterized by the presence of a dipeptide repeat protein in cerebrospinal fluid (CSF), the method comprising contacting the CSF of a subject in need thereof with an effective amount of a protease capable of removing or degrading the dipeptide repeat protein, wherein the dipeptide repeat protein comprises two or more repeats of a dipeptide amino acid sequence.

In certain embodiments, the dipeptide amino acid sequence is selected from the group consisting of glycine-alanine (GA), glycine-arginine (GR), alanine-proline (AP), glycine-proline (GP), and proline-arginine (PR). In certain embodiments, the dipeptide amino acid sequence is glycine-arginine (GR). In certain embodiments, the dipeptide amino acid sequence is glycine-alanine (GA).

In certain embodiments, the dipeptide repeat protein comprises four or more repeats of the dipeptide amino acid sequence. In certain embodiments, the dipeptide repeat protein comprises six or more repeats of the dipeptide amino acid sequence. In certain embodiments, the dipeptide repeat protein comprises eight or more repeats of the dipeptide amino acid sequence. In certain embodiments, the dipeptide repeat protein comprises ten or more repeats of the dipeptide amino acid sequence. In certain embodiments, the dipeptide repeat protein comprises 75 or more repeats of the dipeptide amino acid sequence. In certain embodiments, the dipeptide repeat protein comprises 150 or more repeats of the dipeptide amino acid sequence. In certain embodiments, the dipeptide repeat protein comprises 700 or more repeats of the dipeptide amino acid sequence.

In certain embodiments, the dipeptide repeat protein is a mutant chromosome 9 open reading frame 72 (C9orf72) protein. In certain embodiments, the neurological disorder is selected from the group consisting of amyotrophic lateral sclerosis (ALS), frontotemporal dementia (FTD), and frontotemporal lobar degeneration (FTLD).

In certain embodiments, the protease is selected from the group consisting of trypsin, thrombin, proteinase K, elastase, Factor Xa, kallikreins, clostripains, calpains, cathepsins, and thermolysin. In certain embodiments, the protease is trypsin. In certain embodiments, the protease is elastase. In certain embodiments, the protease is clostripain. In certain embodiments, the clostripain is not activated with a reducing agent. In certain embodiments, the protease is a kallikrein. In certain embodiments, the kallikrein is kallikrein-6 (neurosin) or kallikrein-5. In certain embodiments kallikrein 6 is in a proform and activated by lysyl endopeptidase before or during use in the methods of treatment of the present disclosure.

In certain embodiments, the protease is immobilized to a solid substrate. In certain embodiments, the solid substrate comprises a porous solid substrate. In certain embodiments, the solid substrate comprises a cross-linked resin. In certain embodiments, the cross-linked resin comprises an agarose resin. In certain embodiments, the protease is immobilized by covalent cross-linking to the solid substrate.

In certain embodiments, the protease is contacted with the CSF in situ. In certain embodiments, the solid substrate is comprised in a system that is implanted into the subject. In certain embodiments, the system is implanted into the subarachnoid space of the subject. In certain embodiments, the system further comprises a size filter that removes large biomolecules.

In certain embodiments, the CSF is removed from the subject prior to being contacted with the protease and is administered back to the subject after being contacted with the protease. In certain embodiments, the method further comprises a step of filtering the CSF to remove large biomolecules prior to administration of the CSF back to the subject.

In certain embodiments, the method further comprises the step of detecting the dipeptide repeat protein from the CSF of the subject. In certain embodiments, the step of detection is conducted prior to the step of contacting, thereby identifying the subject as suitable for the treatment. In certain embodiments, the subject identified as suitable for the treatment has an elevated level of the dipeptide repeat protein in the CSF compared to a subject that does not have any neurological disorder.

In certain embodiments, the subject is a human.

Other objects and advantages will become apparent to those skilled in the art from a consideration of the ensuing Detailed Description, Examples, and Claims.

BRIEF DESCRIPTION OF THE DRAWINGS

FIG. 1A is a bar graph of a control immobilized reaction, resin and no protease; FIG. 1B is a bar graph of a control solution reaction, buffer and no protease; FIG. 1C is a bar graph showing digestion of $(GR)_{10}$ by immobilized trypsin and commercial immobilized trypsin in PBS buffer; FIG. 1D is a bar graph showing digestion of $(GR)_{10}$ by trypsin in solution.

FIG. 2A is a bar graph of a control immobilized reaction, resin and no protease; FIG. 2B is a bar graph of a control solution reaction, buffer and no protease; FIG. 2C is a bar graph showing digestion of $(GR)_{10}$ by immobilized elastase; FIG. 2D is a bar graph of digestion of $(GR)_{10}$ by solution elastase.

FIG. 3A is a bar graph of a control immobilized reaction, resin and no protease; FIG. 3B is a bar graph of a control solution reaction, buffer and no protease; FIG. 3C is a bar graph showing digestion of $(GR)_{10}$ by immobilized clostripain (not activated); FIG. 3D is a bar graph showing digestion of $(GR)_{10}$ by clostripain (not activated) in solution.

FIG. 4A is a bar graph of a control immobilized reaction, resin and no protease; FIG. 4B is a bar graph of a control solution reaction, buffer and no protease; FIG. 4C is a bar graph showing digestion of $(GR)_{10}$ by immobilized clostripain (activated with 2.5 mM DTT); FIG. 4D is a bar graph showing digestion of $(GR)_{10}$ by clostripain (activated with DTT) in solution.

FIG. 7A is a bar graph showing the results for digestion of $(GR)_{10}$ by clostripain without DTT activation; FIG. 7B is a bar graph showing the results for digestion of $(GR)_{10}$ by clostripain pre-activated with 2.5 mM DTT.

FIG. 8A is a bar graph showing PBS control, no resin, no protease; FIG. 8B is a bar graph showing a resin control reaction, agarose resin, no protease; FIG. 8C is a bar graph showing the results of digestion of $(GR)_{10}$ by immobilized trypsin on agarose resin after storage for over 2 months at 4° C.; FIG. 8D is a bar graph showing the results of digestion of $(GR)_{10}$ by immobilized elastase on agarose resin after storage for over 2 months at 4° C.

FIG. 10A is a LC/MS profile showing baseline peptide data in the absence of elastase; FIG. 10B is a LC/MS profile showing peptide data after treatment with 33 µg/mL of elastase for 60 minutes; FIG. 10C is a LC/MS profile showing peptide data after treatment with 330 µg/mL of elastase for 60 min.

DETAILED DESCRIPTION

Definitions

Figure 1A:
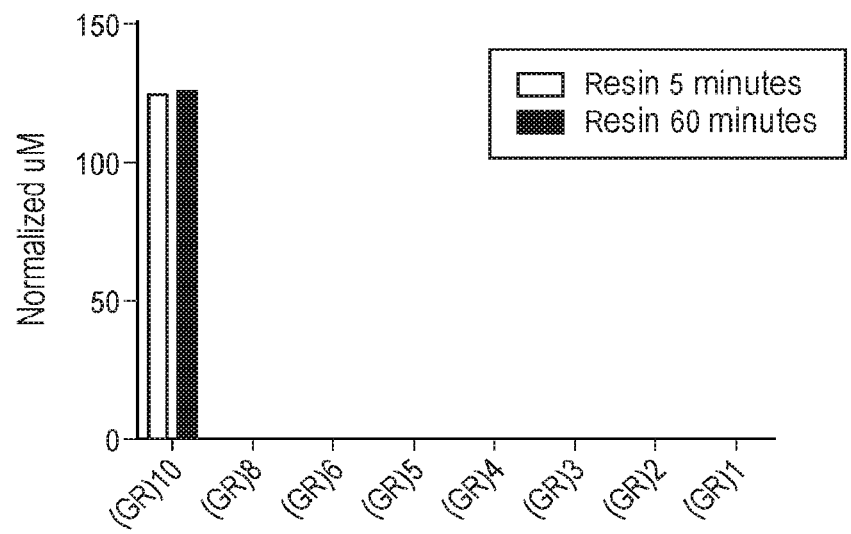
FIGS. 1A-1D are bar graphs showing the results of digestion of $(GR)_{10}$ by trypsin in PBS buffer (normalized)

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomologus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, reduces the severity of at least one symptom of the disease, disorder or condition or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of an agent refers to an amount sufficient to elicit the desired biological response. As will be appreciated by those of ordinary skill in this art, the effective amount of an agent of the invention may vary depending on such factors as the desired biological endpoint, the pharmacokinetics of the agent, the disease being treated, the mode of administration, and the age, health, and condition of the subject. An effective amount encompasses therapeutic and prophylactic treatment.

As used herein, and unless otherwise specified, a "therapeutically effective amount" of an agent is an amount sufficient to provide a therapeutic benefit in the treatment of a disease, disorder or condition, or to delay or minimize one or more symptoms associated with the disease, disorder or condition. A therapeutically effective amount of an agent means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, the term "C9orf72 positive" (e.g., C9orf72 positive neurological disorder, e.g., C9orf72 positive status, e.g., C9orf72 positive subject) refers to the existence of a genetic mutation characterized by the presence of hexanucleotide GGGGCC repeat expansions in the non-coding region of chromosome 9 open reading frame 72 gene (C9orf72).

As used herein, the term "toxic protein" refers to (a) an abnormal protein (e.g., an abnormal variant or mutant of a naturally occurring protein) or an abnormally high amount of a naturally occurring protein that has a negative effect on the health and survival of a target tissue (e.g., brain or neuronal tissue), i.e., in a toxic form; or (b) a protein that can be converted (e.g., by misfolding, aggregation, post-translational modification, or proteolytic cleavage) under pathophysiological conditions to a protein described in (a), i.e., in a nontoxic form.

As used herein, the term "significant effect" refers to an effect that is measurable, has a magnitude that is outside the margin of error of the measurement (i.e., is statistically significant) and is known or predicted to have a clinically meaningful impact in a subject (e.g., it is known or predicted to cause a clinically significant increase or decrease in the severity of a symptom or side effect or to cause or contribute to the development of a symptom or side effect not previously present in the subject).

As used herein, the term "immobilized" refers to an agent (e.g., an antibody or an enzyme) that is attached to an inert, insoluble material or is otherwise made insoluble as a precipitate (e.g., an amorphous precipitate, e.g., a crystalline precipitate), as a cross-linked precipitate (e.g., an amorphous cross-linked precipitate, e.g., a crystalline cross-linked precipitate) or by encapsulation (e.g., encapsulation in a porous container).

Methods of Treating Cerebrospinal Fluid (CSF)

The invention provides for a method for treating a neurological disorder characterized by the presence of a dipeptide repeat protein in cerebrospinal fluid (CSF), the method comprising contacting the CSF of a subject in need thereof with an effective amount of a protease capable of removing or degrading the dipeptide repeat protein, wherein the dipeptide repeat protein comprises two or more repeats of a dipeptide amino acid sequence.

The invention also provides for compositions comprising
a) cerebrospinal fluid (CSF) of a subject having a neurological disorder characterized by the presence of a dipeptide repeat protein in the CSF; and
b) a protease capable of degrading or removing the dipeptide repeat protein.

In an embodiment, the dipeptide repeat protein is a chromosome 9 open reading frame 72 (C9orf72) protein carrying a mutation (e.g., insertion of two or more repeats of a dipeptide amino acid sequence). A neurological disease is designated as a dipeptide repeat protein positive if it is characterized by the presence of a dipeptide repeat protein in the CSF. Accordingly, in certain embodiments, the neurological disorder is a C9orf72 positive neurological disorder.

In a further embodiment, the neurological disorder is selected from the group consisting of C9orf72 positive amyotrophic lateral sclerosis (ALS), C9orf72 positive frontotemporal dementia (FTD), C9orf72 positive frontotemporal lobar degeneration (FTLD).

The dipeptide repeat protein can be present in various forms. In certain embodiments, the dipeptide repeat protein is present in a toxic form (e.g., protein aggregate, protein tangles, protein oligomer, protein fibril, hyperphosphorylated protein, or misfolded protein) in the CSF. In certain embodiments, the dipeptide repeat protein is present in a nontoxic form in the CSF.

In certain embodiments, the subject is a human. In certain embodiments, the subject is a non-human animal (e.g. a dog, a cat, a horse, a cow, a pig, a sheep, a goat, a chicken, or a non-human primate).

Figure 11:
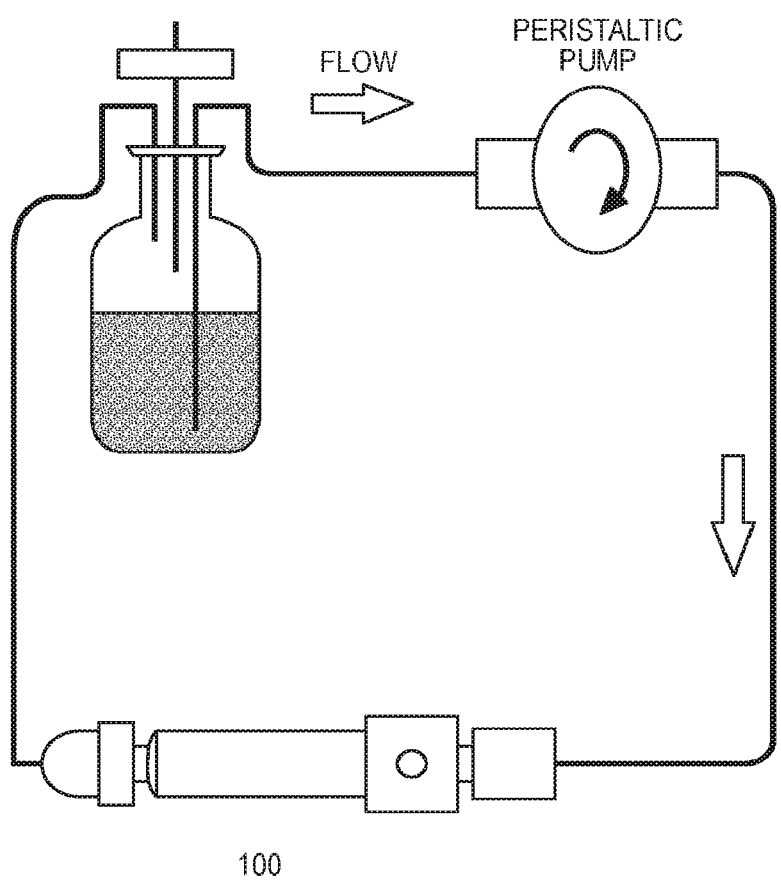
FIG. 11 is a representative diagram showing an exemplary apparatus for removal of CSF containing a dipeptide repeat protein and reintroduction of CSF following contact with a device 100 comprising protease immobilized on an agarose column.

In some embodiments, the CSF is removed from the subject prior to contacting with the agent and is reintroduced into the subject after contacting with the agent for the necessary length of time to effect treatment. For example, CSF may be removed by a peristaltic pump according to the flow diagram in FIG. 11 and reintroduced into the subject after the CSF contacts a device (100) comprising protease immobilized on an agarose column.

In certain embodiments, the present disclosure provides a method by which the CSF of a subject (e.g., human) is contacted with a protease immobilized or connected to a solid surface, e.g., the inner surface of a device (e.g., a cartridge 100 of FIG. 11), implanted into the body of the subject. In certain embodiments, during or after use of the agent, the agent or the solid surface to which the protease is immobilized is extracted and a new batch of the protease or solid support (e.g., resin) to which a new batch of the protease is immobilized is reintroduced by injection to the device implanted in the subject. In certain embodiments, the removal or degradation of the dipeptide repeat protein by contacting the CSF with the protease creates a concentration gradient of the dipeptide repeat protein within the device. In exemplary embodiments, the direction of the concentration gradient is from the input to the output ends of the device, with higher concentration on the input end.

In certain other embodiments, the present disclosure provides a method comprising a step of removing the CSF from the subject (e.g., a non-human mammal (e.g., a dog, a cat, a horse, a cow, a pig, a sheep, a goat, a chicken, or a non-human primate)) prior to contacting the CSF with the protease and a step of reintroducing the CSF back into the subject after contacting it with the protease. For example, in some embodiments, the method comprises a step of removing the CSF from the subject prior to contacting the CSF with a device comprising an agent immobilized on an agarose column, and a step of reintroducing the CSF back into the subject after contacting the CSF with the device.

In certain embodiments, the protease used to perform the method is immobilized (e.g., immobilized on a solid substrate). In a further embodiment, the agent is immobilized by cross-linking to porous beads or porous membranes. In certain embodiments, the dipeptide repeat protein is removed or degraded by contacting the CSF with a concentration gradient of the protease.

In some embodiments, the protease is immobilized on a solid support. In further embodiments, the solid support is a porous solid support. In some embodiments of the invention, the protease is attached to the support by covalent binding. In certain embodiments, the support is a cross-linked resin. In a further embodiment, the cross-linked resin is an agarose resin. In certain embodiments, the protease is immobilized on the solid support at a concentration of about 1 mg/mL to about 10 mg/mL.

In a further embodiment, before or after contacting with the protease, the CSF is filtered to remove the treatment agent prior to being reintroduced into the subject.

In some embodiments, the CSF is continually circulated between the patient and an ex-vivo compartment containing the treatment agent.

In other embodiments of the invention, the protease is contacted with the CSF in situ. An in situ method can be implemented by implanting a system comprising an agent disclosed herein into the subject, for example, into the subarachnoid space of the subject. Such implantation allows continual degradation and removal of a dipeptide repeat protein from the CSF, and may have a lower risk of CNS infection than repeated ex corporeal methods. Accordingly, in certain embodiments, the method comprises contacting the CSF with a device implanted in the subject, wherein the device comprises the agent immobilized on a substrate. In some embodiments, the agent can be delivered into or extracted from the device implanted in the subject by injection (e.g., through a subcutaneous injection port).

In a further embodiment, the method comprises administering the agent capable of removing or degrading the dipeptide repeat protein directly to the CSF of the patient.

In certain embodiments, the dipeptide repeat protein is removed or degraded by contacting the CSF with a concentration gradient of the protease (e.g., contacting the CSF with a concentration gradient of protease immobilized on a substrate). In certain embodiments, the protein is removed or degraded by contacting the CSF with immobilized proteases (e.g., contacting the CSF with a protease immobilized on a substrate).

Removal and/or Degradation of Dipeptide Repeat Proteins

The invention provides for a method for treating a neurological disorder characterized by the presence of a dipeptide repeat protein in cerebrospinal fluid (CSF), the method comprising contacting the CSF of a subject in need thereof with an effective amount of a protease capable of removing or degrading the dipeptide repeat protein, wherein the dipeptide repeat protein comprises two or more repeats of a dipeptide amino acid sequence.

A dipeptide repeat is a sequence of any two amino acids (a "dipeptide sequence") that repeats 2 or more times within the structure of a polypeptide or protein. The dipeptide repeat proteins can cause neurodegeneration for example through impaired proteasome activity, induction of endoplasmic reticulum stress (Zhang et al., *Acta Neuropathol*, 2014, 128, 505-524), formation of toxic amyloids (May et al., *Acta Neuropathol*, 2014, 128, 485-503), and prion-like propagation (Chang et al., *J. Biol. Chem*, 2016, 291, 4903-4911).

The method provides for the removal and/or degradation of dipeptide-repeat proteins where the dipeptide repeat can have various lengths. For example, the protein can have 2 or more 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 75 or more, 100 or more, 150 or more, 200 or more, 250 or more, 300 or more, 350 or more, 400 or more, 450 or more, 500 or more, 600 or more, 700 or more, 800 or more, 900 or more, or 1,000 or more repeats of a dipeptide sequence. A person skilled in the art will understand that these ranges are provided for exemplary purposes only, and dipeptide repeats of other lengths are within the scope of the invention.

In certain embodiments, the dipeptide repeat protein comprises dipeptide repeats selected from glycine-alanine (GA) repeats, glycine-arginine (GR) repeats, alanine-proline (AP) repeats, glycine-proline (GP) repeats and proline-arginine (PR) repeats. In certain embodiments, the dipeptide repeat protein comprises dipeptide repeats selected from (AG) repeats, (RG) repeats, (PA) repeats, (PG) repeats and (RP) repeats. In certain embodiments the dipeptide repeat protein comprises (GR) dipeptide repeats. In certain embodiments the dipeptide repeat protein comprises (GA) dipeptide repeats. The dipeptide repeats are sometimes described in the specification and claims herein with an indicator of the length of the repeat such as $(GA)_x$, $(GR)_x$, $(AP)_x$, $(GP)_x$ and $(PR)_x$, wherein x is an integer denoting the number of repeats of the dipeptide sequence. In exemplary embodiments, x can be 2, 3, 4, 5, 6, 7, 8, 9, 10, 15, 20, 25, 30, 35, 40, 45, 50, 75, 100, 150, 200, 250, 300, 350, 400, 450, 500, 600, 700, 800, 900, or 1,000.

Proteases

The invention provides for a method for treating a neurological disorder characterized by the presence of a dipeptide repeat protein in cerebrospinal fluid (CSF), the method comprising contacting the CSF of a subject in need thereof with an effective amount of a protease capable of removing or degrading the dipeptide repeat protein, wherein the dipeptide repeat protein comprises two or more repeats of a dipeptide amino acid sequence.

The invention also provides for compositions comprising
a) cerebrospinal fluid (CSF) of a subject having a neurological disorder characterized by the presence of a dipeptide repeat protein in the CSF; and
b) a protease capable of degrading or removing the dipeptide repeat protein.

The selective degradation of the dipeptide repeat protein by the protease of the present invention is accomplished by a combination of substrate selectivity (proteases that preferentially recognize the dipeptide repeat protein), cleavage-site specificity (proteases that have specificity for cleaving the peptide bonds of the residue motifs encountered in the dipeptide repeat protein, substrate affinity (based on binding kinetics) and cleavage efficiency (rate of cleavage reaction). In certain embodiments of the invention, the protease is a mammalian, microbial (e.g., fungal, bacterial, or viral), or plant protease.

In certain embodiments, the protease is a serine protease. Exemplary mammalian serine proteases include trypsin, thrombin, elastase, kallikreins (KLK1-KLK15), tryptase a/b 1, chymotrypsin, cathepsin G, granzyme A, granzyme B, granzyme G, granzyme N, granzyme O, granzyme D, granzyme E, granzyme F, high temperature requirement serine protease A1 (HTRA1), matriptase 1, matriptase 2, matriptase 3, and hepsin. Exemplary bacterial serine proteases include subtilisin novo, subtilisin Carlsberg, Alcalase, Glutamyl endopeptidase, Endoproteinase Glu-C, Savirase, and Endoproteinase Lys-C. Exemplary fungal serine proteases include Proteinase K, and any one of the fungal proteases described in de Souza et al., *Brazilian J. of Microbiol.*, 46(2): 337-346 (2015), which can digest a dipeptide repeat protein of the present disclosure. Exemplary plant serine proteases include Benghalensin, HbSPA, HbSPB, and HbSPC. Exemplary viral serine proteases include HRV3C. For example, the serine protease can be chymotrypsin A, glutamyl endopeptidase I, DegP peptidase, lysyl endopeptidase, streptogrisin A, astrovirus serine peptidase, togavirin, IgA1-specific serine peptidase, flavivirin, subtilisin Carlsberg, kexin, prolyl oligopeptidase, dipeptidyl-peptidase IV, acylaminoacyl-peptidase, glutamyl endopeptidase C, carboxypeptidase Y, D-Ala-D-Ala carboxypeptidase A, D-Ala-D-Ala carboxypeptidase B, D-Ala-D-Ala peptidase C, peptidase Clp, Xaa-Pro dipeptidyl-peptidase, Lon-A peptidase, cytomegalovirus assembling, repressor LexA, signal peptidase I, signalase 21 kDa component, TraF peptidase, lysosomal Pro-Xaa carboxypeptidase, hepacivirin, potyvirus P1 peptidase, pestivirus NS3 polyprotein peptidase, equine arteritis virus serine peptidase, prolyl aminopeptidase, PS-10 peptidase, sobemovirus peptidase, luteovirus peptidase, C-terminal processing peptidase-1, tricorn core peptidase, penicillin G acylase precursor, dipeptidyl-peptidase 7, HetR putative peptidase, signal peptide peptidase A, protein C, archaean signal peptide peptidase 1, infectious pancreatic necrosis birnavirus Vp4 peptidase, dipeptidase E, sedolisin, rhomboid-1, SpoIVB peptidase, nucleoporin 145, influenza A PA peptidase, Ssy5 peptidase, picornain-like serine peptidase, murein tetrapeptidase LD-carboxypeptidase, PIDD auto-processing protein unit 1, Tellina virus 1 VP4, MUC1 self-cleaving, dystroglycan, gpO peptidase, *Escherichia coli* phage K1F endosialidase CIMCD self-cleaving protein, White bream virus serine peptidase, prohead peptidase gp21, prohead peptidase, CARD8 self-cleaving protein prohead peptidase gp175, destabilase, or autocrine proliferation repressor protein A. For example, in certain embodiments, the serine protease is trypsin, elastase or thrombin.

In certain embodiments, the protease is a threonine protease. Exemplary mammalian threonine proteases include proteasome catalytic subunits (1, 2, 3, 1i, 2i, 3i), proteasome beta (1, 2, 3, 4, 3-like) subunits, proteasome alpha (1-8, 3-like) subunits, taspase, and glycosylasparaginase.

In certain embodiments, the protease is an aspartic protease. Exemplary mammalian aspartic proteases include pepsin A, pepsin C, chymosin, cathepsin D, cathepsin E, napsin A, napsin B, b-secretase 1, b-secretase 2, presinilin 1, and presinilin 2. Exemplary bacterial aspartic proteases include signal peptidase II and prepilin. Exemplary fungal aspartic proteases include pepsin (A1), retropepsin (A2), and saccharopepsin. Exemplary plant aspartic proteases include nepenthisen. Exemplary viral aspartic proteases include retropepsin. For example, the aspartic protease can be pepsin, endothiapepsin, cathepsin D, cathepsin E, BACE1, BACE2, renin, napsin-A, nepenthesin, signal peptidase II, presenilin, GPR endopeptidase, Omptin, HIV-1 retropepsin, Ty3 transposon peptidase, Gypsy transposon peptidase, Osvaldo retrotransposon peptidase, cauliflower mosaic virus-type peptidase, bacilliform virus peptidase, thermopsin, spumapepsin, Copia transposon peptidase, Ty1 transposon peptidase, impas 1 peptidase, type 4 prepilin peptidase 1, FlaK peptidase, DNA-damage inducible protein 1, skin SASPase, HybD peptidase, PerP peptidase, sporulation factor SpoIIGA, or sso1175 g.p. For example in certain embodiments, the aspartic protease is pepsin or endothiapepsin.

In certain embodiments, the protease is a cysteine protease. Exemplary mammalian cysteine proteases include cathepsin B, cathepsin C, cathepsin F, cathepsin H, cathepsin K, cathepsin L, cathepsin L2, cathepsin O, cathepsin S, cathepsin W, cathepsin Z, cathepsin M, cathepsin Q, calpain 1, calpain 2, calpain 3, calpain 5, calpain 6, calpain 7, calpain 8, calpain 9, calpain 10, calpain 11, calpain 12, calpain 13, calpain 14, caspase 1, caspase 2, caspase 3, caspase 4, caspase 5, caspase 6, caspase 7, caspase 8, caspase 9, caspase 10, caspase 11, caspase 12, caspase 13, caspase 14, and asparagine endopeptidase AEP. Exemplary bacterial cysteine proteases include clostripain (Endoproteinase Arg-C) and gingapain. Exemplary fungal cysteine proteases include macrocypins. Exemplary plant cysteine proteases include papain and Bromelain. Exemplary viral cysteine proteases include adenovirus proteinase. The catalytic activity of certain cysteine proteases may be dependent upon the redox state. In certain embodiments, the cysteine protease is in an oxidized state (e.g., by placing in proximity to an oxidative agent). In certain embodiments, the cysteine protease is in a reduced state (e.g., by placing in proximity to an reducing agent). The oxidized enzyme may retain enough residual activity to be useful given, in particular, the very long treatment time (hours or days, for example) that could be employed in practice, compared to the very short timelines of chemical/enzymatic reactions (micro-seconds to even seconds), as well as the large amount of enzyme relative to substrate (approaching stoichiometric levels vs. substrate) that can be achieved. In certain embodiments, the oxidation time might be slow enough to retain significant levels of reduced enzyme.

In certain embodiments, the protease is a glutamic acid protease. Exemplary bacterial glutamic acid proteases include pepG1. Exemplary fungal glutamic acid proteases include proteases in the Eqolosins family (e.g., Scytalido-glutamic peptidase B).

In certain embodiments, the protease is a metalloprotease. Exemplary mammalian metalloproteases include aminopeptidase A, aminopeptidase B, aminopeptidase N, aminopeptidase PILS, aminopeptidase O, aminopeptidase Q, aminopeptidase B-like 1, stromelysin 1, matrilysin, meprin, ADAM (1-33), and neprilysin. Exemplary bacterial metalloproteases include thermolysin, neutrase, and endopeptidase Asp-N. Exemplary fungal metalloproteases include fungalysin and Mpr1. Exemplary plant metalloproteases include metzincins. The catalytic activity of a metalloprotease is dependent upon the presence of a metal ion in the protease, and leaching of the metal ion may result in a loss of the activity in an in situ method. Accordingly, in certain embodiments, the metalloprotease binds the metal ion with a dissociation constant ($K_D$) lower than (i.e., affinity greater than) $1 \times 10^{-11}$ M, $1 \times 10^{-12}$ M, or $1 \times 10^{-13}$ M.

In certain embodiments, the protease is not a metalloprotease. For example, in certain embodiments, the protease is not thermolysin, carboxypeptidase A1, angiotensin-converting enzyme, aminopeptidase N, matrix metalloproteinase-1, cytosolic carboxypeptidase 6, eutrilysin, aminopeptidase P, glutamate carbodypeptidase II, pappalysin-1, site 2 peptidase, Atp23 peptidase, chloride channel accessory protein 1, Tiki1 peptidase, or Spartan peptidase.

In certain embodiments the protease is not a cysteine protease. For example, in certain embodiments, the protease is not papain, bromelain, clostripain, cathepsin B, cathepsin C, cathepsin F, cathepsin H, cathepsin K, cathepsin L1, cathepsin L2, cathepsin O, cathepsin S, cathepsin W, cathepsin Z, catepcalpain 2, ubiquitinyl hydrolase-L1, streptopain, ubiquitinyl hydrolase-L1, ubiquitin-specific peptidase 14, aminophosphoribosyltransferase precursor, autophagin-1, Cezanne peptidase, otubain, CyID peptidase, caspase-1, OTLD1 deubiquitinylating enzyme, ataxin-3, acid ceramidase precursor, USPL1 peptidase, OTULIN peptidase, coagulation factor XIIIa, or MINDY-1 protein.

In certain embodiments, the protease is not an enzyme that is dependent on a non-covalently bound co-factor for proteolytic activity. For example, in certain embodiments, the protease is not serine protease factor VIIa.

Table 1 lists exemplary proteases that can be used in the method disclosed herein.

TABLE 1

Exemplary Proteases

| Protease | Amino Acid Sequence |
|---|---|
| Bovine trypsin | IVGGYTCAENSVPYQVSLNAGYHFCGGSLINDQWVVSAAHCYQY HIQVRLGEYNIDVLEGGEQFIDASKIIRHPKYSSWTLDNDILLIKLS TPAVINARVSTLLLPSACASAGTECLISGWGNTLSSGVNYPDLLQC LVAPLLSHADCEASYPGQITNNMICAGFLEGGKDSCQGDSGGPVA CNGQLQGIVSWGYGCAQKGKPGVYTKVCNYVDWIQETIAANS (SEQ ID NO: 1) |
| Human trypsin (mature form of Trypsinogen C) | IVGGYTCEENSVPYQVSLNSGSHFCGGSLISEQWVVSAGHCYKPH IQVRLGEHNIEVLEGNEQFINAAKIIRHPKYNRITLNNDIMLIKLST PAVINAHVSTISLPTAPPAAGTECLISGWGNTLSSGADYPDELQCL DAPVLTQAKCKASYPLKITSKMFCVGFLEGGKDSCQGDSGGPVV CNGQLQGIVSWGYGCAQKRRPGVYTKVYNYVDWIKDTIAANS (SEQ ID NO: 2) |
| Human trypsin (mature form of PRSS1) | IVGGYNCEENSVPYQVSLNSGYHFCGGSLINEQWVVSAGHCYKS RIQVRLGEHNIEVLEGNEQFINAAKIIRHPQYDRKTLDNDILLIKLS SPAVINSRVSAISLPTAPPAAGTESLISGWGNTLSSGADYPDELQCL DAPVLSQAECEASYPGKITNNMFCVGFLEGGKDSCQGDSGGPVV SNGELQGIVSWGYGCAQKNRPGVYTKVYNYVDWIKDTIAANS (SEQ ID NO: 3) |
| Porcine pancreatic elastase | VVGGTEAQRNSWPSQISLQYRSGSSWAHTCGGTLIRQNWVMTA AHCVDRELTFRVVVGEHNLNQNNGTEQYVGVQKIVVHPYWNTD DVAAGYDIALLRLAQSVTLNSYVQLGVLPRAGTILANNSPCYITG WGLTRTNGQLAQTLQQAYLPTVDYAICSSSSYWGSTVKNSMVC AGGDGVRSGCQGDSGGPLHCLVNGQYAVHGVTSFVSRLGCNVT RKPTVFTRVSAYISWINNVIASN (SEQ ID NO: 4) |
| Mature human chymotrypsin-like elastase 1 (CELA1) | VVGGTEAGRNSWPSQISLQYRSGGSRYHTCGGTLIRQNWVMTAA HCVDYQKTFRVVAGDHNLSQNDGTEQYVSVQKIVVHPYWNSDN VAAGYDIALLRLAQSVTLNSYVQLGVLPQEGAILANNSPCYITGW GKTKTNGQLAQTLQQAYLPSVDYAICSSSSYWGSTVKNTMVCAG GDGVRSGCQGDSGGPLHCLVNGKYSVHGVTSFVSSRGCNVSRKP TVFTQVSAYISWINNVIASN (SEQ ID NO: 5) |
| Mature human chymotrypsin-like elastase 2A (CELA2A) | VVGGEEARPNSWPWQVSLQYSSNGKWYHTCGGSLIANSWVLTA AHCISSSRTYRVGLGRHNLYVAESGSLAVSVSKIVVHKDWNSNQI SKGNDIALLKLANPVSLTDKIQLACLPPAGTILPNNYPCYVTGWG RLQTNGAVPDVLQQGRLLVVDYATCSSSAWWGSSVKTSMICAG GDGVISSCNGDSGGPLNCQASDGRWQVHGIVSFGSRLGCNYYHK PSVFTRVSNYIDWINSVIANN (SEQ ID NO: 6) |
| Mature human chymotrypsin-like elastase 2B (CELA2B) | MLGGEEARPNSWPWQVSLQYSSNGQWYHTCGGSLIANSWVLTA AHCISSSGIYRVMLGQHNLYVAESGSLAVSVSKIVVHKDWNSDQ VSKGNDIALLKLANPVSLTDKIQLACLPPAGTILPNNYPCYVTGW GRLQTNGALPDDLKQGQLLVVDYATCSSSGWWGSTVKTNMICA GGDGVICTCNGDSGGPLNCQASDGRWEVHGIGSLTSVLGCNYYY KPSIFTRVSNYNDWINSVIANN (SEQ ID NO: 7) |
| Mature human chymotrypsin-like elastase 3A (CELA3A) | VVHGEDAVPYSWPWQVSLQYEKSGSFYHTCGGSLIAPDWVVTA GHCISRDLTYQVVLGEYNLAVKEGPEQVIPINSEELFVHPLWNRS CVACGNDIALIKLSRSAQLGDAVQLASLPPAGDILPNKTPCYITGW GRLYTNGPLPDKLQQARLPVVDYKHCSRWNWWGSTVKKTMVC AGGYIRSGCNGDSGGPLNCPTEDGGWQVHGVTSFVSAFGCNFIW KPTVFTRVSAFIDWIEETIASH (SEQ ID NO: 8) |
| Mature human chymotrypsin-like elastase 3B (CELA3B) | VVNGEDAVPYSWPWQVSLQYEKSGSFYHTCGGSLIAPDWVVTA GHCISSSRTYQVVLGEYDRAVKEGPEQVIPINSGDLFVHPLWNRS CVACGNDIALIKLSRSAQLGDAVQLASLPPAGDILPNETPCYITGW GRLYTNGPLPDKLQEALLPVVDYEHCSRWNWWGSSVKKTMVC AGGDIRSGCNGDSGGPLNCPTEDGGWQVHGVTSFVSAFGCNTRR KPTVFTRVSAFIDWIEETIASH (SEQ ID NO: 9) |
| Mature human cathepsin D light chain | GPIPEVLKNYMDAQYYGEIGIGTPPQCFTVVFDTGSSNLWVPSIHC KLLDIACWIHHKYNSDKSSTYVKNGTSFDIHYGSGSLSGYLSQDT VSVPCQS (SEQ ID NO: 10) |

TABLE 1-continued

Exemplary Proteases

| Protease | Amino Acid Sequence |
|---|---|
| Mature human cathepsin D heavy chain | LGGVKVERQVFGEATKQPGITFIAAKFDGILGMAYPRISVNNVLP VFDNLMQQKLVDQNIFSFYLSRDPDAQPGGELMLGGTDSKYYKG SLSYLNVTRKAYWQVHLDQVEVASGLTLCKEGCEAIVDTGTSLM VGPVDEVRELQKAIGAVPLIQGEYMIPCEKVSTLPAITLKLGGKG YKLSPEDYTLKVSQAGKTLCLSGFMGMDIPPPSGPLWILGDVFIG RYYTVFDRDNNRVGFAEAARL (SEQ ID NO: 11) |
| Human kallikrein-5 | VTEHVLANNDVSCDHPSNTVPSGSNQDLGAGAGEDARSDDSSSRI INGSDCDMHTQPWQAALLLRPNQLYCGAVLVHPQWLLTAAHCR KKVFRVRLGHYSLSPVYESGQQMFQGVKSIPHPGYSHPGHSNDL MLIKLNRRIRPTKDVRPINVSSHCPSAGTKCLVSGWGTTKSPQVH FPKVLQCLNISVLSQKRCEDAYPRQIDDTMFCAGDKAGRDSCQG DSGGPVVCNGSLQGLVSWGDYPCARPNRPGVYTNLCKFTKWIQE TIQANS (SEQ ID NO: 12) |
| Human kallikrein-6 | LVHGGPCDKTSHPYQAALYTSGHLLCGGVLIHPLWVLTAAHCKK PNLQVFLGKHNLRQRESSQEQSSVVRAVIHPDYDAASHDQDIMLL RLARPAKLSELIQPLPLERDCSANTTSCHILGWGKTADGDFPDTIQ CAYIHLVSREECEHAYPGQITQNMLCAGDEKYGKDSCQGDSGGP LVCGDHLRGLVSWGNIPCGSKEKPGVYTNVCRYTNWIQKTIQAK (SEQ ID NO: 13) |

In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to any one of SEQ ID NOs: 1-13. In certain embodiments, the protease comprises an amino acid sequence selected from the group consisting of SEQ ID NOs: 1-13. In certain embodiments, the amino acid sequence of the protease consists of a sequence selected from the group consisting of SEQ ID NOs: 1-13.

In certain embodiments, the protease is a trypsin. In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:1, SEQ ID NO:2, or SEQ ID NO:3. In certain embodiments, the protease comprises the amino acid sequence set forth in SEQ ID NO:1, SEQ ID NO:2, or SEQ ID NO:3. In certain embodiments, the amino acid sequence of the protease consists of the sequence set forth in SEQ ID NO:1, SEQ ID NO:2, or SEQ ID NO:3.

In certain embodiments, the protease is an elastase. In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:4, SEQ ID NO:5, SEQ ID NO:6, SEQ ID NO:7, SEQ ID NO:8, or SEQ ID NO:9. In certain embodiments, the protease comprises the amino acid sequence set forth in SEQ ID NO:4, SEQ ID NO:5, SEQ ID NO:6, SEQ ID NO:7, SEQ ID NO:8, or SEQ ID NO:9. In certain embodiments, the amino acid sequence of the protease consists of the sequence set forth in SEQ ID NO:4, SEQ ID NO:5, SEQ ID NO:6, SEQ ID NO:7, SEQ ID NO:8, or SEQ ID NO:9.

In certain embodiments, the protease is a cathepsin D. In certain embodiments, the protease comprises a first polypeptide chain comprising an amino acid sequence at least 80% (e.g., at least 85%, at least 90% at least 91%, at least 92%, at least 93%, at least 94%, at least 95%, at least 96%, at least 97%, at least 98%, or at least 99%) identical to SEQ ID NO:10 and a second polypeptide chain comprising an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:11. In certain embodiments, the protease comprises a first polypeptide chain comprising the amino acid sequence set forth in SEQ ID NO:10 and a second polypeptide chain comprising the amino acid sequence set forth in SEQ ID NO:11. In certain embodiments, the amino acid sequence of the first polypeptide chain consists of the sequence set forth in SEQ ID NO:10 and the amino acid sequence of the second polypeptide chain consists of the sequence set forth in SEQ ID NO:11.

In certain embodiments, the protease is a kallikrein. In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:12 or SEQ ID NO:13. In certain embodiments, the protease comprises the amino acid sequence set forth in SEQ ID NO:12 or SEQ ID NO:13. In certain embodiments, the amino acid sequence of the protease consists of the sequence set forth in SEQ ID NO:12, or SEQ ID NO:13.

In certain embodiments, the protease is immobilized on the solid support at a concentration of about 1 mg/ml to about 10 mg/ml (e.g., 1-9 mg/ml, 1-8 mg/ml, 1-7 mg/ml, 1-6 mg/ml, 1-5 mg/ml, 1-4 mg/ml, 1-3 mg/ml, 1-2 mg/ml, 2-10 mg/ml, 3-10 mg/ml, 4-10 mg/ml, 5-10 mg/ml, 6-10 mg/ml, 7-10 mg/ml, 8-10 mg/ml, 9-10 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml).

In certain embodiments, the protease is capable of effecting the degradation of the a dipeptide repeat protein faster than the degradation of other proteins (e.g., proteins naturally occurring in the CSF). In certain embodiments, the protease effects the degradation of the dipeptide repeat protein with a similar speed as the degradation of other proteins (e.g., proteins naturally occurring in the CSF). In certain embodiments, the protease is capable of effecting the degradation of a dipeptide repeat protein without significant effects on the concentration of proteins naturally occurring in the CSF. In another embodiment, the protease is not selective for degrading a dipeptide repeat protein versus other proteins (e.g., proteins normally occurring in the CSF). The selective degradation of the dipeptide repeat protein by the protease of the present invention is accomplished by a combination of substrate selectivity (proteases that preferentially recognize the dipeptide repeat protein), cleavage-site specificity (proteases that have specificity for cleaving dipeptide repeat motifs, substrate affinity (based on binding kinetics) and cleavage efficiency (rate of cleavage reaction).

In certain embodiments, the proteases used for performing the method are characterized by an active site capable of selectively recognizing the peptide sequence of the dipeptide repeat protein over other proteins (e.g., proteins normally occurring in the CSF).

In certain embodiments the proteases of the present invention are further capable of higher specificity for the cleavage of at least one peptide bond of a dipeptide repeat protein over cleavage of peptide bonds of other proteins (e.g., proteins normally occurring in the CSF).

In certain embodiments, the protease is characterized by an active site capable of selectively recognizing the dipeptide sequence of the dipeptide repeat protein over other proteins (e.g., proteins normally occurring in the CSF) and is further capable of specific cleavage of the peptide bond of the dipeptide sequence over cleavage of peptide bonds of other proteins (e.g., proteins normally occurring in the CSF).

In certain embodiments, the protease is characterized by an active site capable of specific cleavage at positively charged P1 or P1' residues (e.g., specific cleavage at P1 or P1' arginine residues). In certain embodiments the protease is characterized by an active site capable of specific cleavage at P1 or P1' proline residues. In certain embodiments, the protease is capable of specific cleavage at small hydrophobic P1 or P1' residues (e.g., specific cleavage at P1 or P1' alanine residues, e.g., specific cleavage at P1 or P1' valine residues). The P1 and P1' residue positions are determined according to Schecter and Berger (1967) Biochem. Biophys. Res. Commun. 27(2): 157-62.

There are numerous methods available in the art for assessing the specificity of a protease toward different peptide substrates, including fluorescence resonance energy transfer (FRET), immunocapture, combinations of FRET and enzyme-linked immunosorbent assay (ELISA) based assays, chromatography, combinatorial substrate libraries, use of fluorogenic substrates and labeling techniques. For a review on techniques available for assessing the specificity of proteases see, for example Poreba and Drag, *Curr. Med. Chem.* 2010, 17 (33), 3968-3995 and Diamond, *Curr. Opin. Chem. Biol.* 2007, 11 (1), 46-51.

In certain embodiments of the invention the protease has higher specificity and lower affinity for a dipeptide repeat protein compared to other proteins (e.g., proteins normally occurring in the CSF).

In another embodiment, the protease has higher specificity and higher affinity for a dipeptide repeat protein compared to other proteins (e.g., proteins normally occurring in the CSF).

The affinity of the protease for the substrate can be measured by methods well known in the art, for example by determining the $k_{on}$ and $k_{off}$ rates using surface plasmon resonance.

In certain embodiments of the invention, the protease has higher efficiency cleaving at least one peptide bond of a dipeptide repeat protein compared to the peptide bonds of other proteins (e.g., proteins normally occurring in the CSF).

The efficiency of the protease ($k_{cat}/K_m$) can be determined through enzyme kinetics assays well known in the art, for example spectrophotometric assays, radiometric assays, fluorometric assays, calorimetric assays, light scattering assays, microscale thermophoresis and chromatographic assays. For an overview of enzyme assays that can be used to determine enzyme (e.g., protease) kinetics see, for example Bisswanger, *Practical Enzymology* ($2^{nd}$ edition), Wiley-Blackwell, Weinheim, 2001.

In certain embodiments of the invention, the protease can reduce the concentration of a dipeptide protein by more than 20% in less than a month. In certain embodiments the protease can reduce the concentration of a dipeptide protein by more than 20% in less than a week. In certain embodiments the protease can reduce the concentration of a dipeptide protein by more than 20% in less than a day. In certain embodiments the protease can reduce the concentration of a dipeptide protein by more than 20% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 30% in less than a month. In certain embodiments the protease can reduce the concentration of a dipeptide protein by more than 30% in less than a week. In certain embodiments the protease can reduce the concentration of a dipeptide protein by more than 30% in less than a day. In certain embodiments the protease can reduce the concentration of a dipeptide protein by more than 30% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 40% in less than a month. In certain embodiments the protease can reduce the concentration of a dipeptide protein by more than 40% in less than a week. In certain embodiments the protease can reduce the concentration of a dipeptide protein by more than 40% in less than a day. In certain embodiments the protease can reduce the concentration of a dipeptide protein by more than 40% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 50% in less than a month. In certain embodiments the protease can reduce the concentration of a dipeptide protein by more than 50% in less than a week. In certain embodiments the protease can reduce the concentration of a dipeptide protein by more than 50% in less than a day. In certain embodiments the protease can reduce the concentration of a dipeptide protein by more than 50% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 60% in less than a month. In certain embodiments the protease can reduce the concentration of a dipeptide protein by more than 60% in less than a week. In certain embodiments the protease can reduce the concentration of a dipeptide protein by more than 60% in less than a day. In certain embodiments the protease can reduce the concentration of a dipeptide protein by more than 60% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 70% in less than a month. In certain embodiments the protease can reduce the concentration of a dipeptide protein by more than 20% in less than a week. In certain embodiments the protease can reduce the concentration of a dipeptide protein by more than 70% in less than a day. In certain embodiments the protease can reduce the concentration of a dipeptide protein by more than 70% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 80% in less than a month. In certain embodiments the protease can reduce the concentration of a dipeptide protein by more than 80% in less than a week. In certain embodiments the protease can reduce the concentration of a dipeptide protein by more than 80% in less than a day. In certain embodiments the protease can reduce the concentration of a dipeptide protein by more than 80% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 90% in less than a month. In certain embodiments the protease can reduce the concentration of a dipeptide protein by more than 90% in less than a week. In certain embodiments the protease can reduce the concentration of a dipeptide protein by more than 90% in less than a day. In certain embodiments the protease can reduce the concentration of a dipeptide protein by more than 90% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 95% in less than a month. In certain embodiments the protease can reduce the concentration of a dipeptide protein by more than 95% in less than a week. In certain embodiments the protease can reduce the concentration of a dipeptide protein by more than 95% in less than a day. In certain embodiments the protease can reduce the concentration of a dipeptide protein by more than 95% in less than 60 minutes (e.g., in less than 30 minutes, in less than 20 minutes, in less than 10 minutes, in less than 5 minutes, in less than 2 minutes). In certain embodiments of the invention, the protease can reduce the concentration of a dipeptide protein by more than 99% in less than a month. In certain embodiments the protease can reduce the concentration of a dipeptide protein by more than 99% in less than a week. In certain embodiments the protease can reduce the concentration of a dipeptide protein by more than 99% in less than a day. In certain embodiments the protease can reduce the concentration of a dipeptide protein by more than 99% in less than 60 minutes (e.g., in less than 30 minutes, in less than 20 minutes, in less than 10 minutes, in less than 5 minutes, in less than 2 minutes).

In certain embodiments of the invention, the protease can reduce the concentration of a dipeptide protein below a certain concentration (e.g., below 1000 ng/mL, below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month. In certain embodiments of the invention, the protease can reduce the concentration of a dipeptide protein below a certain concentration (e.g., below 1000 ng/mL, below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a week. In certain embodiments of the invention, the protease can reduce the concentration of a dipeptide protein below a certain concentration (e.g., below 1000 ng/mL, below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a day. In certain embodiments of the invention, the protease can reduce the concentration of a dipeptide protein below a certain concentration (e.g., below 1000 ng/mL, below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than 12 hours. In certain embodiments of the invention, the protease can reduce the concentration of a dipeptide protein below a certain concentration (e.g., below 1000 ng/mL, below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than 6 hours. In certain embodiments of the invention, the protease can reduce the concentration of a dipeptide protein below a certain concentration (e.g., below 1000 ng/mL, below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than 60 minutes (e.g., in less than 30 minutes, in less than 20 minutes, in less than 10 minutes, in less than 5 minutes, in less than 2 minutes).

In certain embodiments of the invention, the protease is selected from the group consisting of trypsin, thrombin, proteinase K, elastase, Factor Xa, kallikreins (e.g., kallikrein-6 or kallikrein-5), clostripains, calpains, cathepsins (e.g., cathepsin-B) and thermolysin. In certain embodiments, the protease is trypsin. In certain embodiments, the proteinase is elastase. In certain embodiments, the protease is a cysteine protease (e.g., clostripains, cathepsins and calpains) activated with a reducing agent (e.g., DTT). In certain embodiments, the protease is a cysteine protease (e.g., clostripains, cathepsins and calpains) in the absence of reducing agents. In certain embodiments, the protease is clostripain. In a further embodiment, the protease is clostripain in the presence of reducing agents. In another embodiment, the protease is clostripain in the absence of reducing agents.

In certain embodiments of the invention, the protease of the treatment method is a protease naturally occurring in CSF. In a further embodiment, the protease is a kallikrein (e.g., kallikrein-6, e.g., kallikrein-5). In a further embodiment, the protease is kallikrein-6. In another embodiment, the protease is kallikrein-5.

Solid Supports

Some embodiments of the present invention provide for the use of immobilized agents (e.g., immobilized enzymes, e.g., immobilized proteases). Advantages of using immobilized agents would be readily apparent to those skilled in the art and comprise ease of manipulation, increased thermal and operational stability, decreased sensitivity to reaction conditions (e.g., pH and temperature), resistance to aggregation, resistance to autodigestion and digestion by other proteases and ease of separation from reaction mixtures.

A variety of modalities for immobilizing biological agents (e.g., enzymes, e.g., proteases) are known in the art and include, without being limited to, affinity-binding to porous materials such as beads and membranes using protein tags, adsorption on porous beads (e.g., glass or alginate beads), adsorption onto membranes, adsorption into matrices and covalent bonding to insoluble supports (e.g., silica gel, e.g., resins), porous supports (e.g., porous beads) or membranes. In some embodiments the biological agents (e.g., enzymes, e.g., proteases) are immobilized on (e.g., by covalent binding to) cross-linked resins. In some embodiments the biological agents (e.g., enzymes, e.g., proteases) are immobilized on (e.g., by covalent binding to) porous beads (e.g., porous resin beads). In further embodiments, the biological agents (e.g., enzymes, e.g., proteases) are immobilized on (e.g., by covalent binding to) cross-linked agarose resins (e.g., 4% or 6% cross-linked agarose resins). For example, the biological agents (e.g., enzymes, e.g., proteases) can be immobilized on porous cross-linked agarose resin beads. In certain embodiments, the agarose resin is an NHS-activated agarose that can be covalently attached to a primary amine. In another embodiment, the agarose resin comprises aldehyde-activated agarose beads for covalent coupling of via primary amines (e.g., AminoLink™ Plus Coupling Resin). In another embodiment the agarose resin is a CDI-activated agarose resin (e.g., Pierce™ resin) that can immobilize proteins that contain N-nucleophiles; pH9-11 O/N reaction. In another embodiment the agarose resin is a resin that can react with sulfhydryl groups to form irreversible thioether bonds (e.g., SulfoLink™ Coupling Resin). In certain embodiments, the biological agents (e.g., enzymes (e.g., proteases)) are immobilized on beads made with a reactive epoxide functionality to react with amines or activated amines to bind enzymes (e.g., proteases) covalently. Beads can be functionalized with reactive entities such as, amongst others, epoxides or succinimides, which can react with enzymes containing free amine groups to form active stable covalently linked immobilized enzyme products.

In some embodiments, a protease can be immobilized on a solid support at a concentration of about 1 mg/ml to about 10 mg/ml (e.g., 1-9 mg/ml, 1-8 mg/ml, 1-7 mg/ml, 1-6 mg/ml, 1-5 mg/ml, 1-4 mg/ml, 1-3 mg/ml, 1-2 mg/ml, 2-10 mg/ml, 3-10 mg/ml, 4-10 mg/ml, 5-10 mg/ml, 6-10 mg/ml, 7-10 mg/ml, 8-10 mg/ml, 9-10 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml). For example, in some embodiments, the protease can be immobilized on the solid support at a concentration of about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml. In certain embodiments, the biological agents (e.g., enzymes (e.g., proteases)) are immobilized (at a concentration of about 1 mg/ml to about 10 mg/ml (e.g., 1-9 mg/ml, 1-8 mg/ml, 1-7 mg/ml, 1-6 mg/ml, 1-5 mg/ml, 1-4 mg/ml, 1-3 mg/ml, 1-2 mg/ml, 2-10 mg/ml, 3-10 mg/ml, 4-10 mg/ml, 5-10 mg/ml, 6-10 mg/ml, 7-10 mg/ml, 8-10 mg/ml, 9-10 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml) on beads made with a reactive epoxide functionality to react with amines or activated amines to bind enzymes (e.g., proteases) covalently.

In some embodiments, the biological agents (e.g., enzymes, e.g., proteases) can be immobilized by precipitation either as amorphous or as crystalline precipitates. Furthermore, the precipitates can be cross-linked to form, for example, cross-linked enzyme (e.g., protease) crystals or cross-liked amorphous precipitates.

In some embodiments, the precipitates (e.g., amorphous precipitates, e.g., crystalline precipitate) and cross-linked precipitates (e.g., cross-linked amorphous precipitates, e.g., cross-linked crystalline precipitates) can form porous matrices with a controlled pore size, wherein the pores can function as size exclusion filters to further enhance the selectivity of the agent (e.g., protease) for the dipeptide repeat protein over other proteins naturally occurring in the CNS.

In some embodiments the lyophilized agent (e.g., the lyophilized enzyme, e.g., the lyophilized protease) is encapsulated in a porous coating designed to be permeable to the substrate, generating agent-containing "beads." In some embodiments, the size of the pores in the porous coating is designed to function as size exclusion filters to further enhance the selectivity of the agent (e.g., protease) for the dipeptide repeat protein over other proteins naturally occurring in the CNS.

Patient Diagnosing and Monitoring

The present invention provides a method for diagnosing a neurological disorder in a subject that is susceptible to a treatment, wherein the treatment comprises contacting the CSF of the subject with an agent (e.g., an enzyme, e.g., an antibody) capable of removing or degrading a dipeptide repeat protein, said method comprising:

a) determining, having determined, or receiving information regarding the presence, amount, and/or form of a dipeptide repeat protein in the CSF of the subject or determining, having determined or receiving information regarding the C9orf72 status of the subject;

b) upon determining, having determined, or receiving information that the dipeptide repeat protein is present in the CSF of the subject, or upon determining, having determined, or receiving information that the subject is C9orf72 positive, diagnosing the subject as susceptible to the treatment.

In certain embodiments, upon determining, having determined or receiving information that the subject is C9orf72 positive the method further comprises determining, having determined or receiving information regarding the presence in the CSF of the patient of a dipeptide repeat protein and diagnosing the patient as susceptible to the treatment if at least one dipeptide repeat protein is present in the CSF.

The presence and/or amount of a dipeptide repeat protein in the CSF of the subject can be evaluated by methods known in the art (e.g., antibody based detection methods (e.g., immunoassays (e.g., ELISA)), immunoaffinity coupled with LC/MS methods, targeted mass spectrometry (e.g., mass spectrometry detection of proteotypic peptides (e.g., tau proteotypic peptides)). The form of a dipeptide repeat protein in the CSF of the subject can also be evaluated by methods known in the art (e.g., size-exclusion chromatography, western blotting (to detect certain post-translational modifications such as hyperphosphorylation), and immunoassays). In certain embodiments, the dipeptide repeat protein is detected in a toxic form (e.g., protein aggregate, protein tangles, protein oligomer, protein fibril, hyperphosphorylated protein, or misfolded protein). In certain embodiments, the dipeptide repeat protein is detected in a nontoxic form.

The present invention also provides a method for predicting the efficacy of a treatment of a neurological disorder in a subject, the treatment comprising contacting the CSF of the subject with an agent (e.g., an enzyme, e.g., an antibody) capable of removing or degrading a dipeptide repeat protein, said method comprising:

determining, having determined or receiving information regarding the presence of a dipeptide repeat protein in the CSF of the subject or determining, having determined or receiving information regarding the C9orf72 status of the subject (e.g., by a method or combination of methods selected from PCR, repeat-primed PCR, capillary sequencing, next generation sequencing and fluorescent fragment-length assay); wherein the said determining, having determined or receiving information that the dipeptide repeat protein is present in the subject's CSF or that the subject is C9orf72 positive is predictive of efficacy of the treatment.

In certain embodiments, upon determining, having determined or receiving information that the subject is C9orf72 positive, (e.g., by a method or combination of methods selected from PCR, repeat-primed PCR, capillary sequencing, next generation sequencing and fluorescent fragment-length assay), the method further comprises determining, having determined or receiving information regarding the presence in the CSF of the patient of dipeptide repeats in the C9orf72 protein wherein the combination of the C9orf72 positive status and presence of dipeptide repeats in the C9orf72 protein in the CSF is predictive of efficacy of the treatment.

The present invention further provides a method for diagnosing and treating a neurological disorder in a subject, wherein the method comprises:

a) determining, having determined or receiving information regarding the presence of a dipeptide repeat protein in the CSF of the subject; or determining, having determined or receiving information regarding C9orf72 status of a subject; and if the subject has been determined to have a dipeptide repeat protein in the CSF, or if the subject has been determined to be C9orf72 positive diagnosing the subject as susceptible to the treatment of step b;

b) treating the subject diagnosed as susceptible in step a) by contacting the cerebrospinal fluid (CSF) of the subject with a protease capable of removing or degrading the dipeptide repeat protein.

In some embodiments, upon determining, having determined or receiving information that the subject is C9orf72 positive, step a) of the method further comprises determining, having determined or receiving information regarding the presence in the CSF of the patient of one or more dipeptide repeat proteins wherein the subject is diagnosed as susceptible to the treatment of step b) by a combination of the C9orf72 positive status and presence of one or more dipeptide repeat proteins in the CSF.

In an embodiment, the C9orf72 status of a subject is determined by analyzing a biological sample from the subject (e.g., a blood sample). In a further embodiment, the biological sample is analyzed for the presence of mutations in the C9orf72 gene (e.g., by a method or combination of methods selected from PCR, repeat-primed PCR, capillary sequencing, next generation sequencing and fluorescent fragment-length assay);

Patient Sample

The terms "patient sample," "subject sample," "biological sample," and "sample" are used interchangeably herein. The subject sample can be a tissue, or bodily fluid, or bodily product. Tissue samples can include fixed, paraffin embedded, fresh, or frozen samples. For example, the tissue sample can include a biopsy or a cheek swab. Exemplary tissues include nervous tissue, brain, skin and hair follicles. Exemplary samples include blood samples and cerebrospinal fluid samples.

Exemplary bodily fluids include blood, plasma, urine, lymph, tears, sweat, saliva, semen, and cerebrospinal fluid. Exemplary bodily products include exhaled breath.

The tissue, fluid or product can be removed from the patient and analyzed. The evaluation can include one or more of: performing the analysis of the tissue, fluid or product; requesting analysis of the tissue fluid or product; requesting results from analysis of the tissue, fluid or product; or receiving the results from analysis of the tissue, fluid or product.

The sample tissue, fluid or product can be analyzed for the presence of a genetic mutation (e.g., mutations in the C9orf72 gene). The sample, tissue, fluid or product can be analyzed for the presence of a dipeptide repeat protein (e.g., comprising GA, GP, AP, GR or PR repeats).

Methods of Evaluating Samples

Evaluating Samples for Genetic Mutations

The presence of a mutation in a gene associated with a neurological disorder (e.g., C9orf72) can be assessed using any of a wide variety of well-known methods for detecting expression of a transcribed molecule, gene, protein, mRNA, genomic DNA, or cDNA. Non-limiting examples of such methods include nucleic acid hybridization-based methods, amplification-based methods, microarray analysis, flow cytometry analysis, DNA sequencing, next generation sequencing, repeat-primed PCR, fluorescent fragment length assays, capillary sequencing, primer extension, PCR, in situ hybridization, dot blot, and Southern blot.

Evaluating Samples for the Presence of Dipeptide Repeat Proteins

The methods described herein can pertain to the evaluation of a patient sample for the presence of a dipeptide repeat protein, e.g., a $(GA)_x$, $(GR)_x$, $(AP)_x$, $(PR)_x$, $(GP)_x$ dipeptide repeat protein, wherein x represents the number of dipeptide repeats and can be any integer equal or higher than 2 (e.g., 2, 3, 4, 5, 6, 7, 8, 9, 10, 15, 20, 25, 30, 35, 40, 45, 50, 75, 100, 150, 200, 250, 300, 350, 400, 450, 500, 600, 700, 800, 900, 1,000, or above). The presence and amount of a dipeptide repeat protein associated with a neurological disorder (e.g., ALS, FTLD, FTD) can be assessed using any of a variety of methods available in the art for detecting and quantifying proteins and/or protein fragments.

In an embodiment, the sample to be analyzed is cerebrospinal fluid (CSF).

In an embodiment, the dipeptide repeat protein can be detected using an immunoassay. As used herein, immunoassays include assays that utilize an antibody to specifically bind to a protein or polypeptide. The polypeptide can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition. Immunoassays for the detection and/or quantification of a protein or polypeptide can take a wide variety of formats well known to those of skill in the art.

An antibody capable of binding to a protein or polypeptide, e.g., an antibody with a detectable label (either directly or indirectly labeled), can be used to detect a dipeptide repeat protein disclosed herein. For a method of detecting dipeptide repeat proteins in brain and CSF see, e.g., U.S. patent application Ser. No. 15/246,267, incorporated herein by reference.

Kits

Described herein are kits comprising a means to treat the CSF of a subject suffering from a neurological disease characterized by the presence of a dipeptide repeat protein. For example, the kit can include a suitably formulated protease capable to degrade or remove the dipeptide repeat protein from the CSF of a subject. The kit can also include means to remove the CSF from the subject for the purpose of contacting it with the agent, means to separate the agent from the CSF after completion of the treatment and means to reintroduce the treated CSF back into the subject. The kit can also include instructions for performing the treatment of the CSF with the provided agent.

Also described herein are kits comprising a means to assay the presence of a dipeptide repeat protein in the CSF of a subject. For example, the kit can include an agent or a plurality of agents (e.g., a monoclonal or polyclonal antibody or a plurality of monoclonal or polyclonal antibodies with a detectable label) capable of interacting specifically with one or more dipeptide repeat proteins (e.g., GA, AP, GP, PR, GR repeat proteins) and means to detect the presence of the labeled antibody-protein conjugate.

EXAMPLES

Example 1. Cleavage of GR Dipeptide Repeats by Exemplary Enzymes in Solution

Reagents:
$(GR)_{10}$ dipeptide (also $(GR)_8$, $(GR)_6$, $(GR)_4$, $(GR)_2$) were synthesized by solid-phase synthesis by CanPeptide; All peptides are uncapped and supplied lyophilized with TFA as counter ions. Purity was always above 95%.
Buffer: PBS buffer containing $CaCl_2$ and $MgCl_2$.
Stock solution of enzyme (e.g., 10 mg/mL) (prepared per manufacturer instructions) in PBS. Activators added as necessary.
Working solution of protein of the desired concentration (e.g., 100 µg/mL) prepared immediately before use by diluting the stock solution (e.g., 5 µL of 10 mg/mL stock solution) in PBS buffer (e.g., in 495 µL of PBS).

Exemplary Procedure Using 50 µM Concentrations of (GR)10

25 µL of a 100 µM solution of $(GR)_{10}$ was added to each well of a 96-well plate. 25 µL of a solution of enzyme (two times the desired final enzyme concentration) was added, and the plates were incubated at room temperature. At the specified time points (5 minutes, 10 minutes, 30 minutes, 60 minutes, and 180 minutes) 2.5 µL of a 10% TFA solution were added to stop the reaction. For the time 0 min well, the TFA was added to the well before addition of the enzyme. After last time point, all samples were further diluted with 150 µL of dilution solution. The quenched reaction mixtures were analyzed by LC/MS to determine the concentration of GR repeats of different lengths.

Detection

The chromatography and mass spectrometry conditions utilized are shown in Table 2 and Table 3, respectively. The limits of quantification for the individual lengths of GR repeats are shown in Table 4.

TABLE 2

HPLC conditions for detecting GR repeats of different lengths:

| LC/MS System | Thermo Accela UPLC/ TSQ Quantum Ultra |
|---|---|
| Column | Waters Xbridge Amide 2.1X50 mm, 3.5 µm |
| Injection Volume | 2 µL |
| Temperature | 45° C. |

Gradient

| Mobile phase A | 0.2% FA in water |
| Mobile phase B | 0.2% FA in acetonitrile |

| Time (Min) | % A | % B | Flow rate (µL/min) |
|---|---|---|---|
| 0 | 10 | 90 | 600 |
| 2.5 | 50 | 50 | 600 |
| 2.6 | 10 | 90 | 1000 |
| 5 | 10 | 90 | 1000 |

TABLE 3

Mass spectrometry conditions for detecting GR repeats of different lengths

| Name | Precursor ion | Product Ion | CE | Tube Lens |
|---|---|---|---|---|
| $(GR)_1$ | 232.1 | 70.0 | 32 | 90 |
| $(GR)_2$ | 445.2 | 289.1 | 20 | 102 |
| $(GR)_4$ | 436.4 | 427.4 | 15 | 95 |
| $(GR)_6$ | 433.3 | 427.5 | 16 | 104 |
| $(GR)_8$ | 432.0 | 417.0 | 15 | 112 |
| $(GR)_{10}$ | 431.0 | 114.7 | 32 | 120 |

TABLE 4

Limits of quantification for GR peptide repeats

| | Quantification limit (µM) |
|---|---|
| $(GR)_1$ | 0.5 |
| $(GR)_2$ | 0.5 |
| $(GR)_4$ | 0.5 |
| $(GR)_6$ | 1.25 |
| $(GR)_8$ | 2.5 |
| $(GR)_{10}$ | 2.5 |

Example 1.1. Cleavage of Various Concentrations of $(GR)_{10}$ at by 2.5 µg/mL and 10 µg/mL Trypsin Solutions Trypsin is a protease that preferably cleaves peptide chains at the carboxyl side of the amino acids lysine or arginine, except when either is followed by proline.

Digestion of $(GR)_{10}$ (50 µM) by trypsin 2.5 µg/mL and 10 µg/mL was performed as described above in the subsection titled "Exemplary procedure using 50 µM concentrations of $(GR)_{10}$." The results for 2.5 µg/mL and 10 µg/mL trypsin are shown in Table 5 and Table 6, respectively.

TABLE 5

Time dependent cleavage of $(GR)_{10}$ by 2.5 µg/mL trypsin in solution
Dipeptide concentration (µM) at Trypsin 2.5 µg/mL

| $(GR)_{10}$ Conc. (µM) | Dipeptide | \multicolumn{6}{c}{Time (min)} | | | | | |
|---|---|---|---|---|---|---|---|
| | | 0 | 5 | 10 | 30 | 60 | 120 |
| 50 | $(GR)_1$ | BLQ | 114.3 | 124.7 | 137.7 | 163.2 | 215.2 |
| | $(GR)_2$ | BLQ | 157.8 | 167.7 | 144.9 | 134.1 | 107.7 |
| | $(GR)_3$ | BLQ | 0.1 | 0.1 | BLQ | BLQ | BLQ |
| | $(GR)_4$ | BLQ | BLQ | BLQ | BLQ | BLQ | BLQ |
| | $(GR)_5$ | BLQ | BLQ | BLQ | BLQ | BLQ | BLQ |
| | $(GR)_6$ | BLQ | BLQ | BLQ | BLQ | BLQ | BLQ |
| | $(GR)_8$ | 0.5 | 0.1 | BLQ | BLQ | BLQ | BLQ |
| | $(GR)_{10}$ | 52.8 | 2.2 | BLQ | BLQ | BLQ | BLQ |
| Recovery % to initial $(GR)_{10}$* | | 106.7 | 90.6 | 93.9 | 86.7 | 87.1 | 86.6 |

*Normalized to molar concentration of GR, E.g., 50 µM $(GR)_{10}$ = 500 µM total GR

TABLE 6

Time dependent cleavage of $(GR)_{10}$ by 10 µg/mL trypsin in solution
Dipeptide concentration (µM) at Trypsin 10 µg/mL

| $(GR)_{10}$ Conc. (µM) | Dipeptide | \multicolumn{6}{c}{Time (min)} | | | | | |
|---|---|---|---|---|---|---|---|
| | | 0 | 5 | 10 | 30 | 60 | 120 |
| 50 | $(GR)_1$ | 0.1 | 124.4 | 156.5 | 212.6 | 289.7 | 349.9 |
| | $(GR)_2$ | BLQ | 138.9 | 148.1 | 110.1 | 58.6 | 10.7 |
| | $(GR)_3$ | BLQ | BLQ | BLQ | BLQ | BLQ | BLQ |
| | $(GR)_4$ | BLQ | BLQ | BLQ | BLQ | BLQ | BLQ |
| | $(GR)_5$ | BLQ | BLQ | BLQ | BLQ | BLQ | BLQ |
| | $(GR)_6$ | BLQ | BLQ | BLQ | BLQ | BLQ | BLQ |
| | $(GR)_8$ | 0.5 | BLQ | BLQ | BLQ | BLQ | BLQ |
| | $(GR)_{10}$ | 48.9 | 2.0 | BLQ | BLQ | BLQ | BLQ |
| Recovery % to initial $GR(GR)_{10}$ | | 98.8 | 84.4 | 92.4 | 87.1 | 81.8 | 74.7 |

*Normalized to molar concentration of GR, E.g., 50 µM $(GR)_{10}$ = 500 µM total GR Almost complete conversion to $(GR)_1$ and $(GR)_2$ was observed in 5 to 10 min using either 2.5 or 10 µg/mL of trypsin for concentrations 50 µM of $(GR)_{10}$.

Example 1.2. Cleavage of Various Concentrations of $(GR)_{10}$ at 2.5 µg/mL and 10 µg/mL Elastase Solution Elastase is a protease that cleaves protein at the carboxyl side of small hydrophobic amino acids such as Ile, Gly, Ala, Ser, Val, and Leu.

Digestion of $(GR)_{10}$ (50 µM) by elastase 2.5 µg/mL and 10 µg/mL was performed as described above in the subsection titled "Exemplary procedure using 50 µM concentrations of $(GR)_{10}$." The results for 2.5 µg/mL and 10 µg/mL elastase are shown in Table 7 and Table 8, respectively.

TABLE 7

Time dependent cleavage of $(GR)_{10}$ by 2.5 µg/mL elastase in solution
Dipeptide concentration (µM) at Elastase 2.5 µg/mL

| $(GR)_{10}$ Conc. (µM) | Dipeptide | \multicolumn{6}{c}{Time (min)} | | | | | |
|---|---|---|---|---|---|---|---|
| | | 0 | 5 | 10 | 30 | 60 | 120 |
| 50 | $(GR)_1$ | BLQ | 0.2 | 0.3 | 1.3 | 2.3 | 4.3 |
| | $(GR)_2$ | BLQ | 0.2 | 0.2 | 0.8 | 1.4 | 2.1 |
| | $(GR)_4$ | BLQ | BLQ | 0.2 | 0.7 | 1.4 | 2.3 |
| | $(GR)_6$ | BLQ | BLQ | BLQ | 0.7 | 1.0 | 1.5 |
| | $(GR)_8$ | BLQ | 0.3 | 0.6 | 0.6 | 1.6 | 2.5 |
| | $(GR)_{10}$ | 53.8 | 52.6 | 52.5 | 43.6 | 35.3 | 24.9 |

TABLE 7-continued

Time dependent cleavage of $(GR)_{10}$ by 2.5 µg/mL elastase in solution
Dipeptide concentration (µM) at Elastase 2.5 µg/mL

| $(GR)_{10}$ Conc. (µM) | Dipeptide | \multicolumn{6}{c}{Time (min)} | | | | | |
|---|---|---|---|---|---|---|---|
| | | 0 | 5 | 10 | 30 | 60 | 120 |
| Recovery % to initial $(GR)_{10}$* | | 107.6 | 105.7 | 106.2 | 90.1 | 76.5 | 59.3 |

*Normalized to molar concentration of GR, E.g., 50 µM GR(10) = 500 µM total GR

TABLE 8

Time dependent cleavage of $(GR)_{10}$ by 10 µg/mL elastase in solution
Dipeptide concentration (µM) at Elastase 10 µg/mL

| $(GR)_{10}$ Conc. (µM) | Dipeptide | \multicolumn{6}{c}{Time (min)} | | | | | |
|---|---|---|---|---|---|---|---|
| | | 0 | 5 | 10 | 30 | 60 | 120 |
| 50 | $(GR)_1$ | BLQ | 0.8 | 1.4 | 5.1 | 8.3 | 15.1 |
| | $(GR)_2$ | BLQ | 0.5 | 0.8 | 2.5 | 3.7 | 6.3 |
| | $(GR)_4$ | BLQ | 0.5 | 0.7 | 2.2 | 2.8 | 3.2 |
| | $(GR)_6$ | BLQ | 0.4 | 0.8 | 1.6 | 2.2 | 2.0 |
| | $(GR)_8$ | BLQ | 0.9 | 0.9 | 2.8 | 3.3 | 1.3 |
| | $(GR)_{10}$ | 41.6 | 50.5 | 37.8 | 21.1 | 12.2 | 2.4 |
| Recovery % to initial $(GR)_{10}$* | | 83.2 | 103.8 | 79.3 | 52.3 | 37.7 | 17.3 |

*Normalized to molar concentration of GR, Eg., 50 µM $(GR)_{10}$ = 500 µM total GR Example 1.3. Cleavage of Various Concentrations of $(GR)_{10}$ by 0.25 µg/mL and 10 µg/mL Proteinase K Solutions Proteinase K is a protease that cleaves peptide bonds adjacent to the carboxylic group of aliphatic and aromatic amino acids Digestion of $(GR)_{10}$ (50 µM) by Proteinase K 0.25 µg/mL and 10 µg/mL was performed as described above in the subsection titled "Exemplary procedure using 50 µM concentrations of $(GR)_{10}$." The results for 0.25 µg/mL and 10 µg/mL Proteinase K are shown in Table 9 and Table 10, respectively.

TABLE 9

Time dependent cleavage of $(GR)_{10}$ by
0.25 µg/mL Proteinase K in solution
Dipeptide concentration (µM) at Proteinase K 0.25 µg/mL

| $(GR)_{10}$ Conc. (µM) | Dipeptide | \multicolumn{6}{c}{Time (min)} | | | | | |
|---|---|---|---|---|---|---|---|
| | | 0 | 2.5 | 5 | 10 | 30 | 60 |
| 50 | $(GR)_1$ | BLQ | BLQ | 0.1 | 0.2 | 0.6 | 1.0 |
| | $(GR)_2$ | BLQ | BLQ | BLQ | BLQ | 0.2 | 0.3 |
| | $(GR)_4$ | BLQ | BLQ | BLQ | BLQ | 0.1 | BLQ |
| | $(GR)_6$ | BLQ | BLQ | BLQ | BLQ | BLQ | BLQ |
| | $(GR)_8$ | 0.3 | BLQ | BLQ | BLQ | 0.3 | 0.3 |
| | $(GR)_{10}$ | 44.9 | 55.8 | 54.4 | 50.3 | 55.1 | 56.3 |
| Recovery % to initial $(GR)_{10}$* | | 90.4 | 111.5 | 108.8 | 100.5 | 110.9 | 113.5 |

*Normalized to molar concentration of GR, E.g., 50 µM $(GR)_{10}$ = 500 µM total GR

TABLE 10

Time dependent cleavage of $(GR)_{10}$ by 10 μg/mL Proteinase K in solution
Dipeptide concentration (μM) at Proteinase K 10 μg/mL

| $(GR)_{10}$ Conc. (μM) | Dipeptide | Time (min) | | | | | |
|---|---|---|---|---|---|---|---|
| | | 0 | 2.5 | 5 | 10 | 30 | 60 |
| 50 | $(GR)_1$ | BLQ | 3.0 | 5.3 | 11.9 | 44.8 | 64.1 |
| | $(GR)_2$ | BLQ | 0.5 | 0.8 | 1.4 | 5.7 | 10.1 |
| | $(GR)_4$ | BLQ | 0.6 | 1.3 | 2.9 | 9.5 | 13.6 |
| | $(GR)_6$ | BLQ | 0.5 | 0.8 | 2.2 | 5.2 | 6.6 |
| | $(GR)_8$ | BLQ | 0.6 | 1.3 | 2.6 | 3.5 | 5.7 |
| | $(GR)_{10}$ | 49.4 | 55.4 | 48.8 | 44.1 | 16.6 | 10.6 |
| Recovery % to initial $(GR)_{10}$* | | 98.7 | 113.7 | 103.0 | 100.2 | 64.0 | 66.1 |

*Normalized to molar concentration of GR, E.g., 50 μM $(GR)_{10}$ = 500 μM total GR

Example 1.4. Cleavage of Various Concentrations of $(GR)_{10}$ at by 2.5 μg/mL and 10 μg/mL Clostripain Solutions Clostripain generally cleaves at the C-terminus of arginine residues, including sites next to proline. Lysine bonds are also cleaved, but at a much slower rate. It is a sulfhydryl protease and the active site residues include Cysteine (C41). Typically, clostripain is used in the presence of activators (reducing agents) such as dithiothreitol (DTT) or cysteine. Calcium ion is essential for the performance of the enzyme.

Digestion of $(GR)_{10}$ (50 μM) by clostripain 2.5 μg/mL and 10 μg/mL was performed as described above in the subsection titled "Exemplary procedure using 50 μM concentrations of $(GR)_{10}$," in the absence of activators such as DTT. The results for 2.5 μg/mL and 10 μg/mL clostripain in the absence of DTT are shown in Table 11 and Table 12, respectively.

TABLE 11

Time dependent cleavage of $(GR)_{10}$ by 2.5 μg/mL clostripain in solution in the absence of DTT
Dipeptide concentration (μM) at Clostripain 2.5 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | 25.6 | 35.3 | 72.9 | 148.6 | 325.0 |
| | $(GR)_2$ | BLQ | 8.7 | 14.0 | 36.8 | 62.1 | BLQ |
| | $(GR)_4$ | BLQ | 6.7 | 9.8 | 7.5 | 1.9 | BLQ |
| | $(GR)_6$ | BLQ | 3.6 | 4.3 | 1.4 | BLQ | BLQ |
| | $(GR)_8$ | 0.7 | 2.2 | 1.8 | BLQ | BLQ | BLQ |
| | $(GR)_{10}$ | 39.7 | 5.4 | 2.3 | BLQ | BLQ | BLQ |
| Recovery % to initial $(GR)_{10}$* | | 80.5 | 32.7 | 33.0 | 36.9 | 56.1 | 65.0 |

*Normalized to molar concentration of GR, E.g., 50 μM $(GR)_{10}$ = 500 μM total GR

TABLE 12

Time dependent cleavage of $(GR)_{10}$ by 10 μg/mL clostripain in solution in the absence of DTT
Dipeptide concentration (μM) at Clostripain 10 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | 99.0 | 145.9 | 336.9 | 340.3 | 355.8 |
| | $(GR)_2$ | BLQ | 51.8 | 62.2 | BLQ | BLQ | BLQ |
| | $(GR)_4$ | BLQ | 5.4 | 1.8 | BLQ | BLQ | BLQ |
| | $(GR)_6$ | BLQ | 0.6 | BLQ | BLQ | BLQ | BLQ |
| | $(GR)_8$ | 0.6 | BLQ | BLQ | BLQ | BLQ | BLQ |
| | $(GR)_{10}$ | 37.9 | 0.8 | BLQ | BLQ | BLQ | BLQ |
| Recovery % to initial $(GR)_{10}$* | | 76.8 | 47.1 | 55.5 | 67.4 | 68.1 | 71.2 |

*Normalized to molar concentration of GR, Eg., 50 μM $(GR)_{10}$ = 500 μM total GR

Example 1.5. Cleavage of Various Concentrations of $(GR)_{10}$ by 0.25 μg/mL and 10 μg/mL Factor Xa Solutions Factor Xa is a protease that cleaves after arginine in its preferred cleavage site Ile-Glu/Asp-Gly-Arg. The most common secondary site, among those that have been sequenced, is Gly-Arg.

Factor Xa is inhibited by PBS buffer and activated by TRIS buffer. Digestion of $(GR)_{10}$ (50 μM) by Factor Xa 0.25 μg/mL and 10 μg/mL was performed as described above in the subsection titled "Exemplary procedure using 50 μM concentrations of $(GR)_{10}$," replacing the PBS buffer with TRIS buffer. The results for 2.5 μg/mL and 10 μg/mL Factor Xa are shown in Table 13 and Table 14, respectively.

TABLE 13

Time dependent cleavage of $(GR)_{10}$ by 2.5 μg/mL Factor Xa in solution
Dipeptide concentration (μM) at Factor Xa 2.5 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | BLQ | BLQ | BLQ | 1.2 | 3.0 |
| | $(GR)_2$ | BLQ | BLQ | 0.6 | 1.5 | 4.2 | 10.1 |
| | $(GR)_4$ | BLQ | BLQ | BLQ | 1.2 | 2.2 | 5.0 |
| | $(GR)_6$ | BLQ | BLQ | BLQ | 0.9 | 1.8 | 3.3 |
| | $(GR)_8$ | BLQ | 0.8 | 2.5 | 3.2 | 6.0 | |
| | $(GR)_{10}$ | 33.1 | 35.0 | 19.4 | 29.7 | 17.5 | 15.3 |
| Recovery % to initial $(GR)_{10}$* | | 66.2 | 70.9 | 40.2 | 65.9 | 45.9 | 52.9 |

*Normalized to molar concentration of GR, E.g., 50 μM $(GR)_{10}$ = 500 μM total GR

TABLE 14

Time dependent cleavage of $(GR)_{10}$ by 10 μg/mL Factor Xa in solution
Dipeptide concentration (μM) at Factor Xa 10 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | 1.4 | 2.8 | 10.7 | 23.7 | 47.2 |
| | $(GR)_2$ | BLQ | 3.6 | 7.5 | 35.6 | 57.9 | 86.5 |
| | $(GR)_4$ | BLQ | 2.7 | 4.2 | 11.2 | 11.4 | 5.2 |
| | $(GR)_6$ | BLQ | 2.1 | 2.4 | 5.6 | 3.1 | 0.6 |
| | $(GR)_8$ | BLQ | 4.2 | 4.8 | 5.2 | 1.4 | BLQ |
| | $(GR)_{10}$ | 31.0 | 23.5 | 13.6 | 5.4 | 0.7 | BLQ |
| Recovery % to initial $(GR)_{10}$* | | 62.0 | 60.0 | 44.6 | 51.2 | 44.4 | 48.9 |

*Normalized to molar concentration of GR, E.g., 50 μM $(GR)_{10}$ = 500 μM total GR

Example 1.6. Cleavage of Various Concentrations of (GR)10 by 0.25 μg/mL and 10 μg/mL Kallikrein 6 Solutions Kallikrein 6 (neurosin) is a protease that cleaves with much higher efficiency after Arg than Lys and with a preference for Ser or Pro in the P2 position.

Kallikrein 6 is in a proform and needs to be activated by Lysyl Endopeptidase. The activated from of kallikrein 6 is not stable and can proteolyse itself. Kallikrein 6 can be autoactivated. Digestion of $(GR)_{10}$ (50 μM) by 0.25 μg/mL and 10 μg/mL of kallikrein 6 was performed as described above in the subsection titled "Exemplary procedure using 50 μM concentrations of $(GR)_{10}$," using autoactivated kallikrein 6. The results for 0.25 μg/mL and 10 μg/mL kallikrein 6 are shown in Table 15 and Table 16, respectively.

TABLE 15

Time dependent cleavage of $(GR)_{10}$ by 0.25 μg/mL kallikrein 6 in solution
Dipeptide concentration (μM) at Kallikrein 0.25 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | BLQ | BLQ | 0.1 | 0.1 | 0.1 |
| | $(GR)_2$ | BLQ | BLQ | BLQ | BLQ | BLQ | 0.1 |
| | $(GR)_3$ | BLQ | BLQ | BLQ | BLQ | BLQ | BLQ |
| | $(GR)_4$ | BLQ | BLQ | BLQ | BLQ | BLQ | BLQ |
| | $(GR)_5$ | BLQ | BLQ | BLQ | BLQ | BLQ | BLQ |
| | $(GR)_6$ | BLQ | BLQ | BLQ | BLQ | BLQ | BLQ |
| | $(GR)_8$ | 0.1 | 0.3 | 0.1 | 0.3 | 0.3 | 0.2 |
| | $(GR)_{10}$ | 27.8 | 42.2 | 50.1 | 57.8 | 54.2 | 54.3 |
| Recovery % to initial $(GR)_{10}$* | | 55.9 | 85.1 | 100.3 | 116.2 | 109.0 | 109.3 |

*Normalized to molar concentration of GR, E.g., 50 μM $(GR)_{10}$ = 500 μM total GR

TABLE 16

Time dependent cleavage of $(GR)_{10}$ by 10 μg/mL kallikrein 6 in solution
Dipeptide concentration (μM) at Kallikrein 10 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | 0.1 | 0.2 | 0.6 | 0.9 | 1.9 |
| | $(GR)_2$ | BLQ | BLQ | 0.2 | 0.5 | 0.9 | 1.8 |
| | $(GR)_3$ | BLQ | 0.1 | 0.2 | 0.4 | 0.9 | 1.6 |
| | $(GR)_4$ | BLQ | BLQ | BLQ | 0.4 | 0.9 | 1.5 |
| | $(GR)_5$ | BLQ | BLQ | 0.1 | 0.2 | 0.5 | 1.0 |
| | $(GR)_6$ | BLQ | BLQ | BLQ | 0.7 | 1.2 | 2.0 |
| | $(GR)_8$ | 0.1 | 0.2 | 0.4 | 1.3 | 2.0 | 3.9 |
| | $(GR)_{10}$ | 54.7 | 57.5 | 60.8 | 65.0 | 71.5 | 57.4 |
| Recovery % to initial $(GR)_{10}$* | | 109.6 | 115.7 | 122.9 | 133.9 | 150.1 | 127.6 |

*Normalized to molar concentration of GR, E.g., 50 μM $(GR)_{10}$ = 500 μM total GR

Example 1.7. Cleavage of Various Concentrations of $(GR)_{10}$ by 2.5 μg/mL and 10 μg/mL Thrombin Solutions Thrombin is a protease that cleaves preferentially at sites with Arg in position P1 and Gly in position P2 and position P1'. Additionally, it cleaves sites wherein hydrophobic residues are found in position P4 and position P3, Pro in position P2, Arg in position P1, and non-acidic amino-acids in position P1' and position P2'.

Thrombin is in a Proform and needs to be activated by thermolysin and stopped by metal chelation with EDTA. The activated form of thrombin is not stable and can be subject to autolysis.

Digestion of $(GR)_{10}$ (50 μM) by thrombin 2.5 μg/mL and 10 μg/mL was performed as described above in the subsection titled "Exemplary procedure using 50 μM concentrations of $(GR)_{10}$," using thrombin activated by thermolysis and quenched by EDTA. The results for 2.5 μg/mL and 10 μg/mL thrombin are shown in Table 17 and Table 18, respectively.

TABLE 17

Time dependent cleavage of $(GR)_{10}$ by 2.5 μg/mL activated thrombin in solution
Dipeptide concentration (μM) at Thrombin 2.5 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | BLQ | BLQ | BLQ | 0.1 | 0.2 |
| | $(GR)_2$ | BLQ | BLQ | BLQ | 0.1 | 0.2 | 0.2 |
| | $(GR)_4$ | 0.1 | 0.1 | 0.1 | 0.2 | 0.3 | 0.4 |
| | $(GR)_6$ | 0.1 | 0.1 | BLQ | 0.1 | 0.1 | 0.3 |
| | $(GR)_8$ | 1.1 | 1.5 | 1.4 | 1.3 | 1.1 | BLQ |
| | $(GR)_{10}$ | 37.7 | 42.9 | 46.7 | 49.1 | 56.2 | 45.3 |
| Recovery % to initial $(GR)_{10}$* | | 77.3 | 88.3 | 95.8 | 100.4 | 114.6 | 92.3 |

*Normalized to molar concentration of GR, E.g., 50 μM $(GR)_{10}$ = 500 μM total GR

TABLE 18

Time dependent cleavage of $(GR)_{10}$ by 10 μg/mL activated thrombin in solution
Dipeptide concentration (μM) at Thrombin 10 μg/mL

| $(GR)_{10}$ Conc. (μM) | Dipeptide | Time (min) | | | | | |
|---|---|---|---|---|---|---|---|
| | | 0 | 5 | 10 | 30 | 60 | 120 |
| 50 | $(GR)_1$ | BLQ | 0.1 | 0.1 | 0.3 | 0.5 | 1.1 |
| | $(GR)_2$ | BLQ | 0.1 | 0.1 | 0.4 | 0.6 | 1.4 |
| | $(GR)_4$ | 0.1 | 0.2 | 0.2 | 0.4 | 0.8 | 1.6 |
| | $(GR)_6$ | BLQ | BLQ | 0.1 | 0.4 | 0.5 | 1.3 |
| | $(GR)_8$ | 1.3 | BLQ | 1.0 | 1.3 | 2.4 | 3.0 |
| | $(GR)_{10}$ | 52.0 | 54.8 | 59.4 | 48.6 | 55.2 | 48.7 |
| Recovery % to initial $(GR)_{10}$* | | 106.0 | 111.2 | 120.9 | 100.4 | 115.8 | 105.8 |

*Normalized to molar concentration of GR, E.g., 50 μM $(GR)_{10}$ = 500 μM total GR

Example 2. Cleavage of GR(10) by Commercial Immobilized Trypsin

Reagents

Immobilized TPCK-trypsin on agarose resin; ThermoFisher Cat #20230 Lot #TA264999; Activity: 555 TAME units/mL of gel; the resin was washed with PBS TPCK-trypsin; ThermoFisher Cat #20233 Lot #SB241185; Activity: 308 TAME units/mg of protein NOTE: One TAME unit is equal to 1 μmole of TAME (p-toluenesulfonyl-L-arginine methyl ester in the presence of Ca2+) hydrolyzed/min at pH 8.2, 25° C. (One TAME unit=19.2 National Formulatory units=57.5 BAEE units 110 μL of 50 μM $(GR)_{10}$ dipeptide repeats prepared in PBS was added to immobilized trypsin in 0.8 mL centrifuge columns and incubated for the prescribed time at room temperature with end-to-end mixing resin. Columns were spun down 1 minute at 1,000 Xg to recover digested GR dipeptides. Columns were washed with 110 μL of PBS to increase $(GR)_{10}$ recovery. 100 μL of each samples were transferred to a new tube and 5 μL of 10% TFA followed by 300 μL of Dilution Solution were added. The reaction mixtures were analyzed by LC/MS to determine the concentration of GR repeats of different lengths.

Results for the digestion of 50 μM $(GR)_{10}$ with 0.625 TAME and 6.25 TAME immobilized trypsin are shown in Table 19 and Table 20, respectively.

TABLE 19

Time dependent cleavage of $(GR)_{10}$ by 0.625 TAME units immobilized trypsin

Dipeptide concentration (μM) at Immobilized trypsin 0.625 TAME Units#

| $(GR)_{10}$ | | Time (min) | | | | | |
|---|---|---|---|---|---|---|---|
| Conc. (μM) | Dipeptide | 0 | 5 | 10 | 30 | 60 | 120 |
| 50 | $(GR)_1$ | BLQ | 248.4 | 307.0 | 411.7 | 465.4 | 385.8 |
| | $(GR)_2$ | BLQ | 114.9 | 89.6 | 11.8 | 5.6 | 1.0 |
| | $(GR)_4$ | 0.1 | 0.3 | 0.2 | 0.1 | BLQ | BLQ |
| | $(GR)_6$ | BLQ | 0.1 | BLQ | BLQ | BLQ | BLQ |
| | $(GR)_8$ | 1.0 | BLQ | BLQ | BLQ | BLQ | BLQ |
| | $(GR)_{10}$ | 68.4 | 3.1 | 2.1 | 0.6 | 1.0 | 0.1 |
| Recovery % to initial $(GR)_{10}$* | | 138.5 | 102.7 | 101.7 | 88.3 | 97.3 | 77.9 |

*Normalized to molar concentration of GR, E.g., 50 μM $(GR)_{10}$ = 500 μM total GR
One TAME unit is equal to 1 μmol of TAME (p-toluenesulfonyl-L-arginine methyl ester in the presence of Ca2+) hydrolyzed/min at pH 8.2, 25° C. (One TAME unit = 19.2 National Formulatory units = 57.5 BAEE units)

TABLE 20

Time dependent cleavage of (GR)10 by 6.25 TAME units immobilized trypsin

Dipeptide concentration (μM) at Immobilized trypsin at 6.25 TAME Units

| $(GR)_{10}$ | | Time (min) | | | | | |
|---|---|---|---|---|---|---|---|
| Conc. (μM) | Dipeptide | 0 | 5 | 10 | 30 | 60 | 120 |
| 50 | $(GR)_1$ | 0.2 | 391.0 | 505.5 | 480.2 | 409.6 | 396.0 |
| | $(GR)_2$ | 0.2 | 1.2 | 3.8 | 0.2 | 0.1 | 0.2 |
| | $(GR)_4$ | 0.1 | BLQ | 0.1 | BLQ | BLQ | BLQ |
| | $(GR)_6$ | BLQ | BLQ | BLQ | BLQ | BLQ | 0.1 |
| | $(GR)_8$ | BLQ | BLQ | BLQ | BLQ | BLQ | BLQ |
| | $(GR)_{10}$ | 32.7 | 0.9 | 1.6 | 0.9 | 0.2 | 0.1 |
| Recovery % to initial $(GR)_{10}$* | | 66.7 | 80.6 | 106.3 | 98.0 | 82.4 | 79.5 |

*Normalized to molar concentration of GR, E.g., 50 μM $(GR)_{10}$ = 500 μM total GR
One TAME unit is equal to 1 μmol of TAME (p-toluenesulfonyl-L-arginine methyl ester in the presence of Ca2+) hydrolyzed/min at pH 8.2, 25° C. (One TAME unit = 19.2 National Formulatory units = 57.5 BAEE units)

Immobilized trypsin at 6.25 TAME Units digests (GR)10 to almost exclusively (GR)1 in 10 to 30 minutes.

Example 3. Cleavage of $(GR)_{10}$ by Enzymes Immobilized on Agarose Resins

Protease Immobilization on NHS Activated Resin:
Protease solutions were prepared at 2 mg/mL in sterile PBS with calcium, magnesium and 200 μL (400 pg) were applied to 100 μL of pre-washed NHS-activated agarose resin in 0.8 mL centrifuge columns. Reactions were left 1.5 hour at room temperature with end-to-end mixing, after which resins were washed with 12 resin volumes of PBS. Unreacted sites were blocked with 500 μL of 1M ethanolamine for 15 minutes at room temperature and resins were further washed with 24 resin volumes. Resins were stored at 4 degrees in 500 μL of PBS containing 0.05% sodium azide as preservative.

$(GR)_{10}$ Digestion with Immobilized Proteases in PBS:
110 μL of 50 μM $(GR)_{10}$ dipeptide repeats prepared in PBS were added to each immobilized protease and incubated 5 minutes at room temperature with end-to-end mixing. Columns were spun down 1 minute at 1,000 Xg to recover digested GR dipeptides. Columns were washed with 110 μL of PBS to increase $(GR)_{10}$ recovery. This procedure was repeated with 60 minutes digestion time. 100 μL of each samples were transferred to a new tube and 5 μL of 10% TFA followed by 300 μL of Dilution Solution were added. The reaction mixtures were analyzed by LC/MS to determine the concentration of GR repeats of different lengths.

$(GR)_{10}$ Digestion with Immobilized Proteases in CSF:
200 μM of $(GR)_{10}$ were diluted in human cerebrospinal fluid (CSF) and 400 μL were applied to each immobilized proteases. The reaction was incubated 5 minutes at room temperature with end-to-end mixing. Columns were spun down 1 minute at 1,000 Xg to recover digested GR dipeptides. Columns were washed with 12 resin volumes of PBS. The procedure was repeated with 60 minutes digestion time. 100 μL of each samples were transferred to a clean tube, flash-frozen and subsequently used for LC/MS quantification of GR repeats of different lengths. The remaining 300 μL of each samples were flash-frozen and used to assess neuron toxicity.

CSF Treatment with Immobilized Proteases:
300 μL of CSF were applied to each immobilized proteases and incubated 60 minutes at room temperature with end-to-end mixing. Columns were spun down 1 minute at 1,000 Xg to recover treated CSF. Samples were flash-frozen and subsequently used to test neuron toxicity.

Figure 1B:
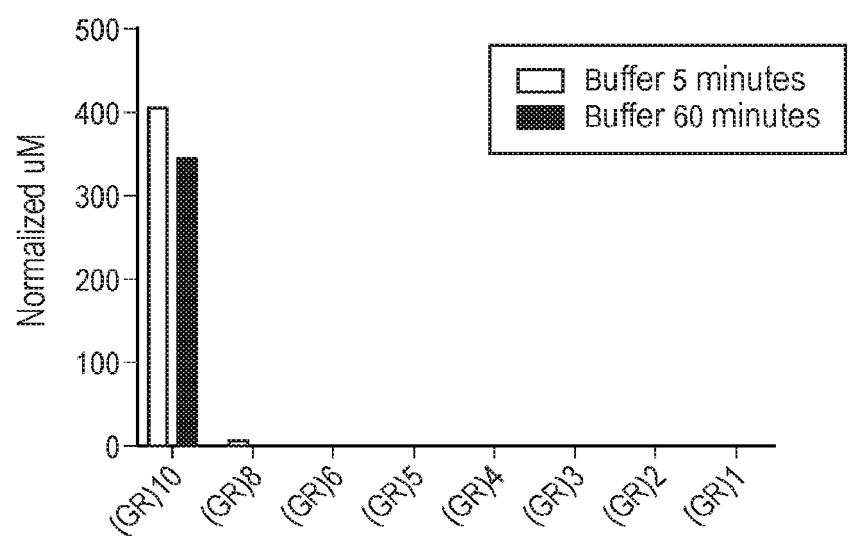
Figure 1C:
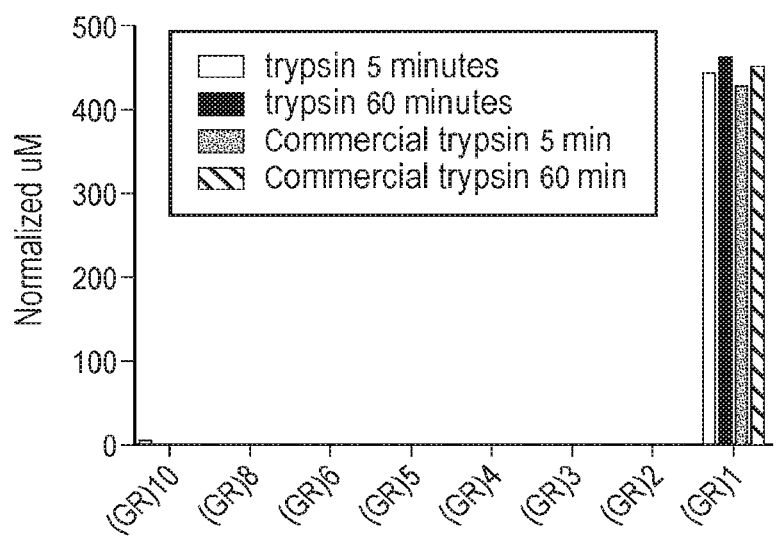
Figure 1D:
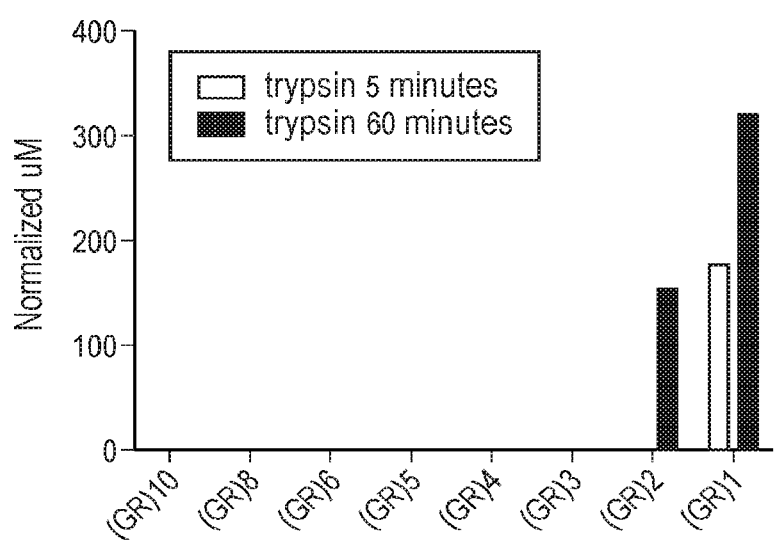

Example 3.1. Cleavage of $(GR)_{10}$ by Trypsin Immobilized on Agarose Resin in PBS $(GR)_{10}$ was digested with immobilized trypsin as described above in the subsection titled "$(GR)_{10}$ digestion with immobilized proteases in CSF" of Example 3. The results obtained after 5 and 60 minutes of reaction time and comparison with the results obtained using commercial immobilized trypsin and solution trypsin are presented in Table 21 and shown in FIG. 1A (control, resin and no protease), FIG. 1B (control, buffer and no protease), FIG. 1C (immobilized trypsin and commercial immobilized trypsin) and FIG. 1D (solution trypsin).

TABLE 21

Cleavage of $(GR)_{10}$ by immobilized trypsin (uM)

| Agent | $(GR)_1$ | $(GR)_2$ | $(GR)_3$ | $(GR)_4$ | $(GR)_5$ | $(GR)_6$ | $(GR)_8$ | $(GR)_{10}$ |
|---|---|---|---|---|---|---|---|---|
| Resin alone - Immobilized - 5 min reaction | 0.0 | 0.0 | 0.0 | 0.0 | 0.0 | 0.0 | 0.0 | 90.3 |
| Resin alone - resin wash from 5 min reaction | 0.0 | 0.0 | 0.0 | 0.0 | 0.0 | 0.0 | 0.0 | 33.3 |
| Resin alone - immobilized - 60 min reaction | 0.0 | 0.0 | 0.0 | 0.0 | 0.0 | 0.0 | 0.0 | 71.1 |

TABLE 21-continued

Cleavage of (GR)$_{10}$ by immobilized trypsin (uM)

| Agent | (GR)$_1$ | (GR)$_2$ | (GR)$_3$ | (GR)$_4$ | (GR)$_5$ | (GR)$_6$ | (GR)$_8$ | (GR)$_{10}$ |
|---|---|---|---|---|---|---|---|---|
| Resin alone - resin wash from 60 min reaction | 0.0 | 0.0 | 0.0 | 0.0 | 0.0 | 0.0 | 0.0 | 54.2 |
| Trypsin - Immobilized - 5 min reaction | 308.8 | 0.0 | 0.0 | 0.0 | 0.0 | 0.0 | 0.0 | 0.0 |
| Trypsin - resin wash from 5 min reaction | 140.2 | 0.0 | 0.0 | 0.0 | 0.0 | 0.0 | 0.0 | 6.6 |
| Trypsin - immobilized - 60 min reaction | 321.8 | 0.0 | 0.0 | 0.0 | 0.0 | 0.0 | 0.0 | 0.0 |
| Trypsin - resin wash from 60 min reaction | 144.6 | 0.0 | 0.0 | 0.0 | 0.0 | 0.0 | 0.0 | 0.0 |
| Commercial Trypsin - Immobilized - 5 min reaction | 301.2 | 0.0 | 0.0 | 0.0 | 0.0 | 0.0 | 0.0 | 0.0 |
| Commercial Trypsin - resin wash from 5 min reaction | 131.9 | 0.0 | 0.0 | 0.0 | 0.0 | 0.0 | 0.0 | 0.0 |
| Commercial Trypsin - immobilized - 60 min reaction | 308.6 | 0.0 | 0.0 | 0.0 | 0.0 | 0.0 | 0.0 | 0.0 |
| Commercial Trypsin - resin wash from 60 min reaction | 145.7 | 0.0 | 0.0 | 0.0 | 0.0 | 0.0 | 0.0 | 0.0 |
| Trypsin - in solution - 5 min reaction | 178.0 | 0.0 | 0.0 | 0.0 | 0.0 | 0.0 | 0.0 | 0.0 |
| Trypsin - in solution - 60 min reaction | 321.4 | 154.0 | 0.0 | 0.0 | 0.0 | 0.0 | 0.0 | 0.0 |
| Buffer only - in solution - 5 min reaction | 0.0 | 0.0 | 0.0 | 0.0 | 0.0 | 0.0 | 4.8 | 403.1 |
| Buffer only - in solution - 60 min reaction | 0.0 | 0.0 | 0.0 | 0.0 | 0.0 | 0.0 | 0.0 | 345.2 |

Figure 2A:
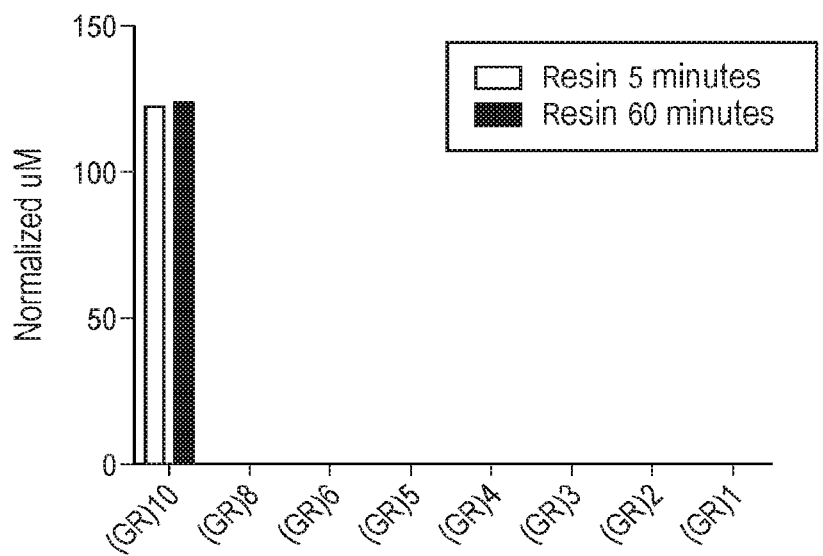
FIGS. 2A-2D are bar graphs showing the results of digestion of $(GR)_{10}$ by elastase in PBS buffer (normalized)
Figure 2B:
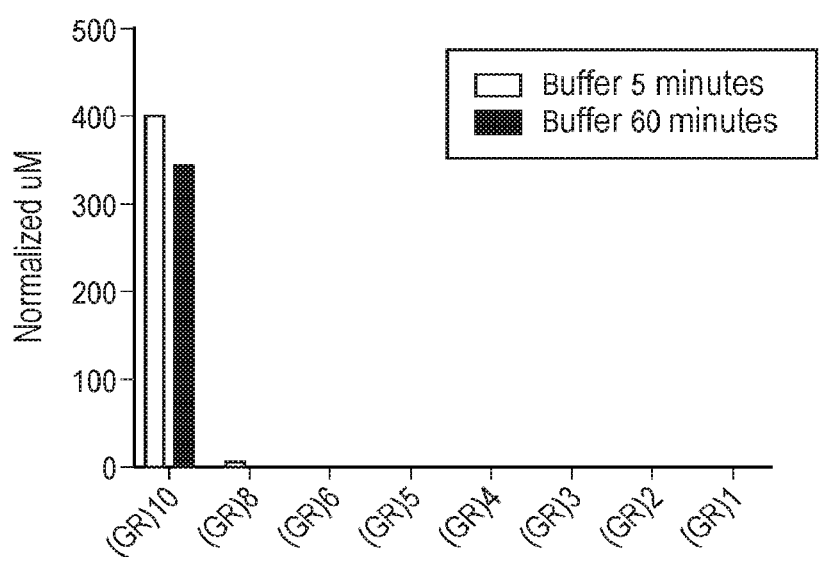
Figure 2C:
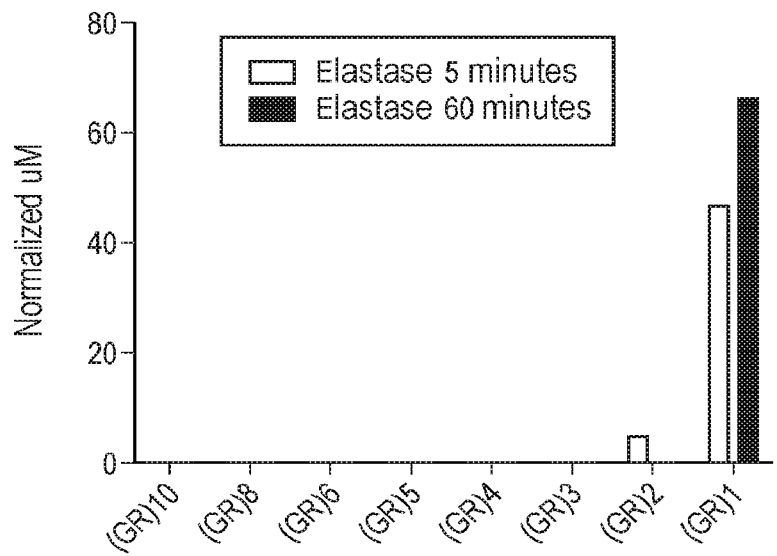
Figure 2D:
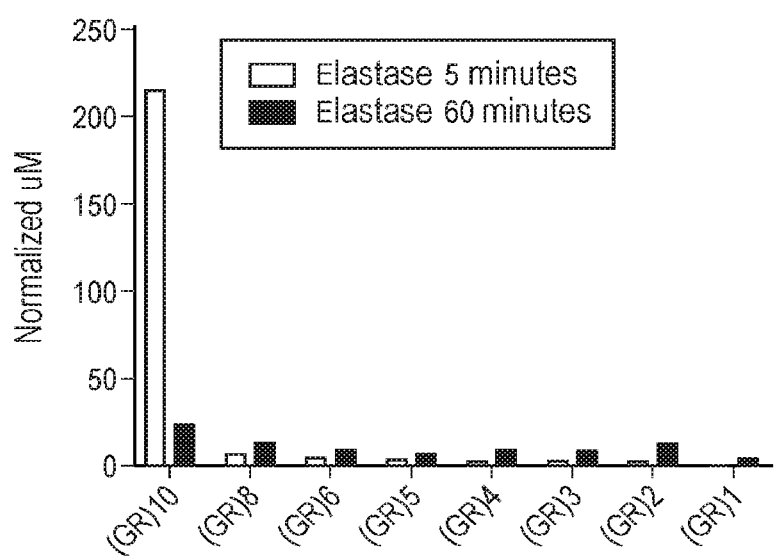

Example 3.2. Cleavage of (GR)$_{10}$ by Elastase Immobilized on Agarose Resin in PBS (GR)$_{10}$ was digested with immobilized elastase as described above in the subsection titled "(GR)$_{10}$ digestion with immobilized proteases in CSF" of Example 3. The results obtained after 5 and 60 minutes of reaction time and comparison with the results obtained using solution elastase are presented in Table 22 and shown in FIG. 2A (control, resin and no protease), FIG. 2B (control, buffer and no protease), FIG. 2C (immobilized elastase) and FIG. 2D (solution elastase).

Figure 3A:
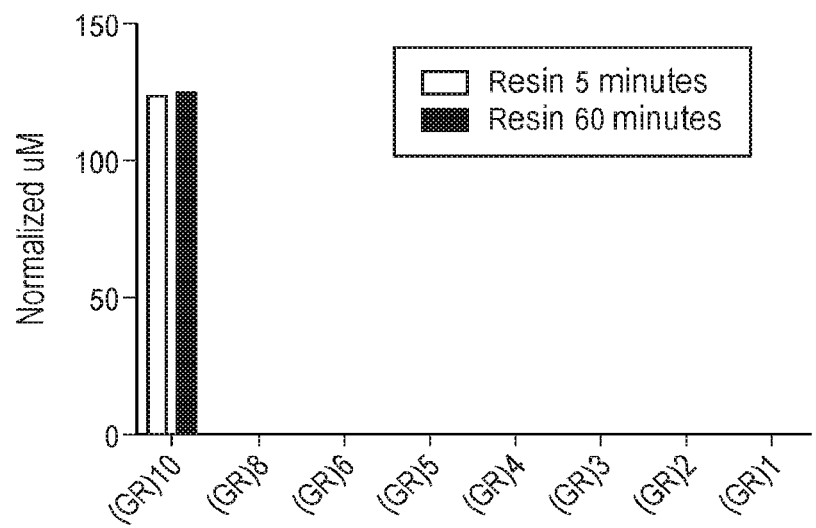
FIGS. 3A-3D are bar graphs showing the results of digestion of $(GR)_{10}$ by clostripain (not activated) in PBS buffer (normalized)

Example 3.3. Cleavage of (GR)$_{10}$ by Clostripain Immobilized on Agarose Resin in the Absence of DTT in PBS (GR)$_{10}$ was digested with immobilized, unactivated clostripain as described above in the subsection titled "(GR)$_{10}$ digestion with immobilized proteases in CSF" of Example 3. The results obtained after 5 and 60 minutes of reaction time and comparison with the results obtained using solution clostripain are presented in Table 23 and shown in FIG. 3A

TABLE 22

Cleavage of (GR)$_{10}$ by immobilized elastase (uM) (normalized to GR concentration)

| Agent | (GR)$_1$ | (GR)$_2$ | (GR)$_3$ | (GR)$_4$ | (GR)$_5$ | (GR)$_6$ | (GR)$_8$ | (GR)$_{10}$ |
|---|---|---|---|---|---|---|---|---|
| Resin alone - Immobilized - 5 min reaction | 0.0 | 0.0 | 0.0 | 0.0 | 0.0 | 0.0 | 0.0 | 90.3 |
| Resin alone - resin wash from 5 min reaction | 0.0 | 0.0 | 0.0 | 0.0 | 0.0 | 0.0 | 0.0 | 33.3 |
| Resin alone - immobilized - 60 min reaction | 0.0 | 0.0 | 0.0 | 0.0 | 0.0 | 0.0 | 0.0 | 71.1 |
| Resin alone - resin wash from 60 min reaction | 0.0 | 0.0 | 0.0 | 0.0 | 0.0 | 0.0 | 0.0 | 54.2 |
| Elastase - Immobilized - 5 min reaction | 33.1 | 4.8 | 0.0 | 0.0 | 0.0 | 0.0 | 0.0 | 0.0 |
| Elastase - resin wash from 5 min reaction | 13.8 | 0.0 | 0.0 | 0.0 | 0.0 | 0.0 | 0.0 | 0.0 |
| Elastase - immobilized - 60 min reaction | 48.1 | 0.0 | 0.0 | 0.0 | 0.0 | 0.0 | 0.0 | 0.0 |
| Elastase - resin wash from 60 min reaction | 18.5 | 0.0 | 0.0 | 0.0 | 0.0 | 0.0 | 0.0 | 0.0 |
| Elastase - in solution - 5 min reaction | 1.4 | 2.9 | 2.1 | 3.1 | 2.3 | 4.4 | 6.8 | 213.3 |
| Elastase - in solution - 60 min reaction | 5.4 | 12.8 | 8.5 | 8.8 | 6.0 | 9 | 12.8 | 21.6 |
| Buffer only - in solution - 5 min reaction | 0.0 | 0.0 | 0.0 | 0.0 | 0.0 | 0.0 | 4.8 | 403.1 |
| Buffer only - in solution - 60 min reaction | 0.0 | 0.0 | 0.0 | 0.0 | 0.0 | 0.0 | 0.0 | 345.2 |

Figure 3B:
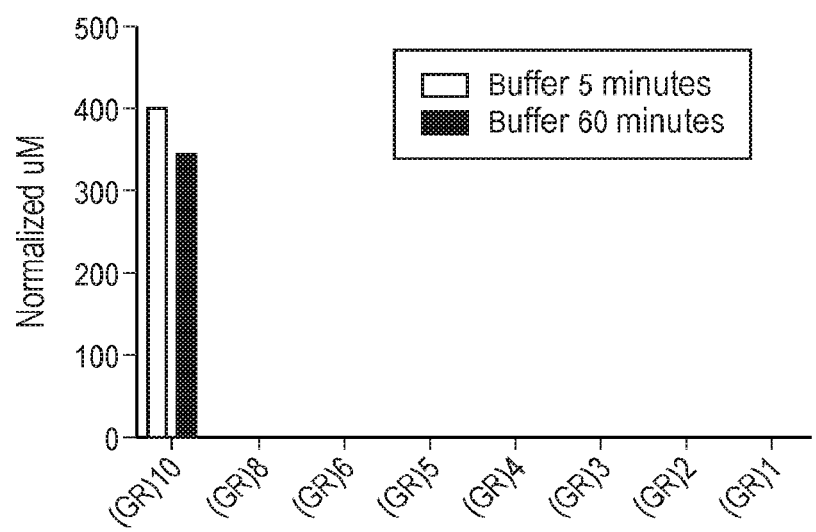
Figure 3C:
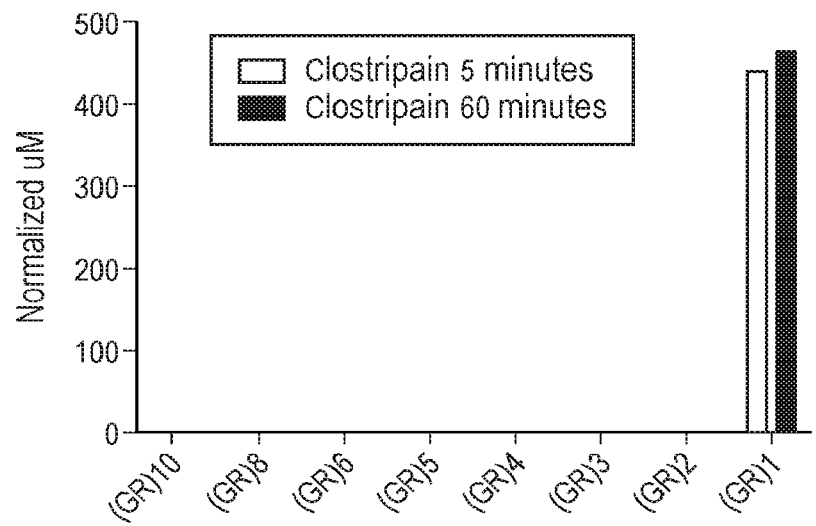
Figure 3D:
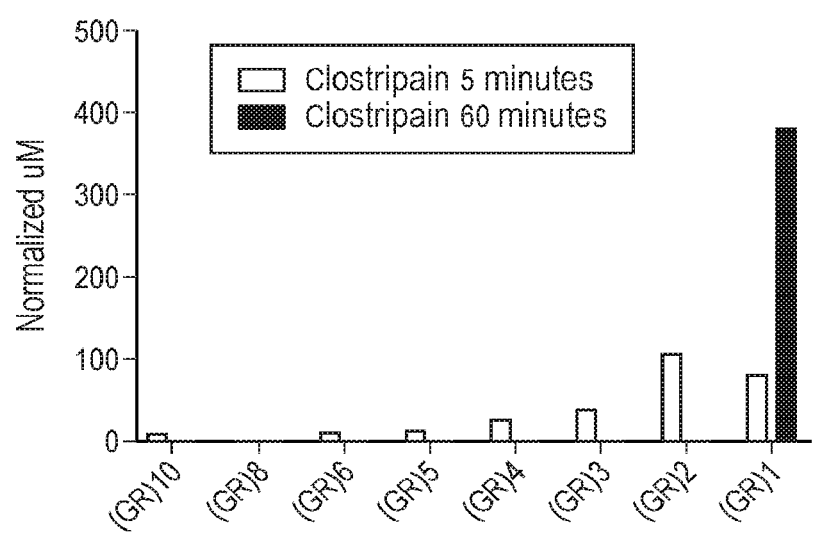

(control, resin and no protease), FIG. 3B (control, buffer and no protease), FIG. 3C (immobilized clostripain) and FIG. 3D (solution clostripain).

TABLE 23

Cleavage of $(GR)_{10}$ by immobilized clostripain (no DTT) (uM)

| Agent | $(GR)_1$ | $(GR)_2$ | $(GR)_3$ | $(GR)_4$ | $(GR)_5$ | $(GR)_6$ | $(GR)_8$ | $(GR)_{10}$ |
|---|---|---|---|---|---|---|---|---|
| Resin alone - Immobilized - 5 min reaction | 0.0 | 0.0 | 0.0 | 0.0 | 0.0 | 0.0 | 0.0 | 90.3 |
| Resin alone - resin wash from 5 min reaction | 0.0 | 0.0 | 0.0 | 0.0 | 0.0 | 0.0 | 0.0 | 33.3 |
| Resin alone - immobilized - 60 min reaction | 0.0 | 0.0 | 0.0 | 0.0 | 0.0 | 0.0 | 0.0 | 71.1 |
| Resin alone - resin wash from 60 min reaction | 0.0 | 0.0 | 0.0 | 0.0 | 0.0 | 0.0 | 0.0 | 54.2 |
| Clostripain - Immobilized - 5 min reaction | 296.5 | 0.0 | 0.0 | 0.0 | 0.0 | 0.0 | 0.0 | 0.0 |
| Clostripain - resin wash from 5 min reaction | 140.2 | 0.0 | 0.0 | 0.0 | 0.0 | 0.0 | 0.0 | 0.0 |
| Clostripain - immobilized - 60 min reaction | 305.9 | 0.0 | 0.0 | 0.0 | 0.0 | 0.0 | 0.0 | 0.0 |
| Clostripain - resin wash from 60 min reaction | 155.8 | 0.0 | 0.0 | 0.0 | 0.0 | 0.0 | 0.0 | 0.0 |
| Clostripain - in solution - 5 min reaction | 82.6 | 106.2 | 39.1 | 28.6 | 12.7 | 8.4 | 0.0 | 12.4 |
| Clostripain - in solution - 60 min reaction | 383.2 | 0.0 | 0.0 | 0.0 | 0.0 | 0.0 | 0.0 | 0.0 |
| Buffer only - in solution - 5 min reaction | 0.0 | 0.0 | 0.0 | 0.0 | 0.0 | 0.0 | 4.8 | 403.1 |
| Buffer only - in solution - 60 min reaction | 0.0 | 0.0 | 0.0 | 0.0 | 0.0 | 0.0 | 0.0 | 345.2 |

Figure 4A:
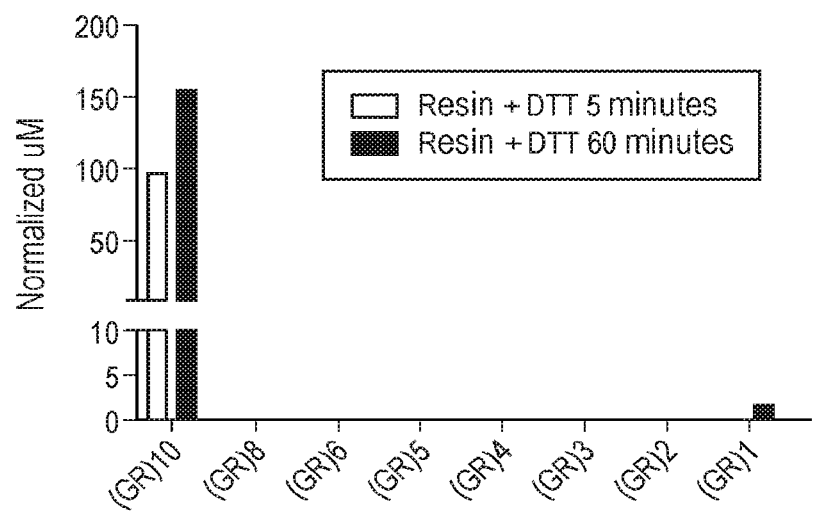
FIGS. 4A-4D are bar graphs showing the results of digestion of $(GR)_{10}$ by clostripain (activated with 2.5 mM DTT) in PBS buffer (normalized)
Figure 4B:
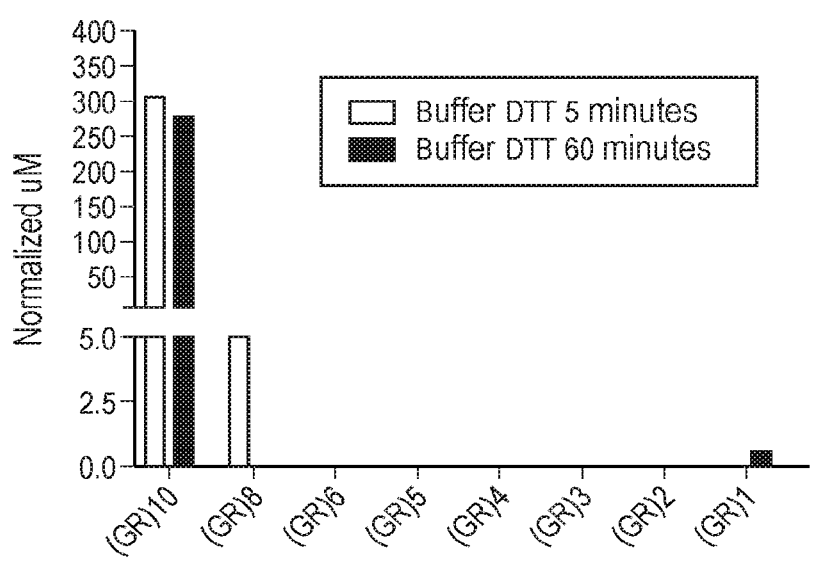
Figure 4C:
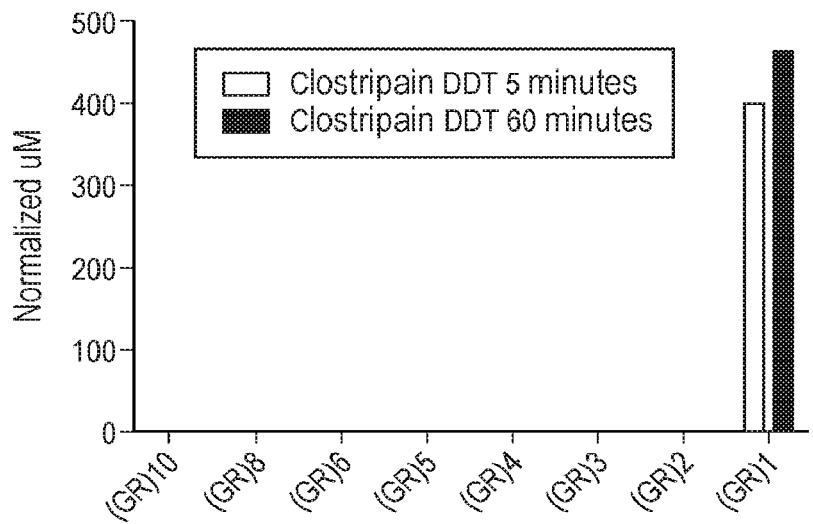
Figure 4D:
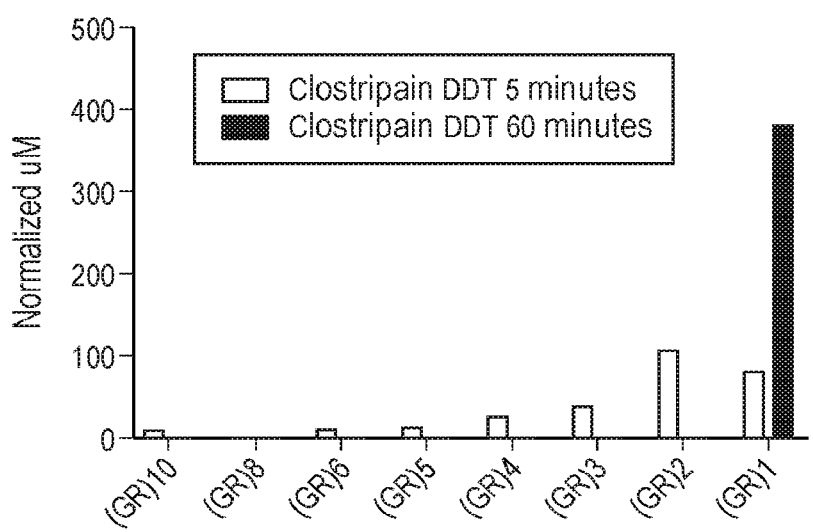

Example 3.4. Cleavage of $(GR)_{10}$ by Clostripain Immobilized on Agarose Resin Re-Activated with DTT in PBS $(GR)_{10}$ was digested in PBS with immobilized clostripain activated with 2.5 mM DTT as described above in the subsection titled "$(GR)_{10}$ digestion with immobilized proteases in CSF" of Example 3 (no DTT during digestion). The results obtained after 5 and 60 minutes of reaction time and comparison with the results obtained using solution clostripain activated with 2.5 mM DTT (no DTT during digestion) are presented in Table 24 and shown in FIG. 4A (control, resin and no protease), FIG. 4B (control, buffer and no protease), FIG. 4C (immobilized clostripain) and FIG. 4D (solution clostripain).

TABLE 24

Cleavage of $(GR)_{10}$ by immobilized clostripain (with 2.5 mM DTT) (uM) (normalized to GR concentration)

| Agent | $(GR)_1$ | $(GR)_2$ | $(GR)_3$ | $(GR)_4$ | $(GR)_5$ | $(GR)_6$ | $(GR)_8$ | $(GR)_{10}$ |
|---|---|---|---|---|---|---|---|---|
| Resin + DTT - Immobilized - 5 min reaction | 0.4 | 0.0 | 0.0 | 0.0 | 0.0 | 0.0 | 0.0 | 75.2 |
| Resin + DTT - resin wash from 5 min reaction | 0.0 | 0.0 | 0.0 | 0.0 | 0.0 | 0.0 | 0.0 | 22.3 |
| Resin + DTT - immobilized - 60 min reaction | 0.6 | 0.0 | 0.0 | 0.0 | 0.0 | 0.0 | 0.0 | 118.6 |
| Resin + DTT - resin wash from 60 min reaction | 0.5 | 0.0 | 0.0 | 0.0 | 0.0 | 0.0 | 0.0 | 36.5 |
| Clostripain + DTT - Immobilized - 5 min reaction | 299.3 | 0.0 | 0.0 | 0.0 | 0.0 | 0.0 | 0.0 | 0.0 |
| Clostripain + DTT - resin wash from 5 min reaction | 99.1 | 0.0 | 0.0 | 0.0 | 0.0 | 0.0 | 0.0 | 0.0 |
| Clostripain + DTT - immobilized - 60 min reaction | 335.6 | 0.0 | 0.0 | 0.0 | 0.0 | 0.0 | 0.0 | 0.0 |
| Clostripain + DTT - resin wash from 60 min reaction | 125.6 | 0.0 | 0.0 | 0.0 | 0.0 | 0.0 | 0.0 | 0.0 |
| Clostripain + DTT - in solution - 5 min reaction | 86.8 | 113.6 | 40.5 | 27.2 | 12.1 | 7.3 | 0.0 | 5.7 |
| Clostripain + DTT - in solution - 60 min reaction | 387.0 | 0.0 | 0.0 | 0.0 | 0.0 | 0.0 | 0.0 | 0.0 |

TABLE 24-continued

Cleavage of (GR)$_{10}$ by immobilized clostripain (with 2.5 mM DTT) (uM) (normalized to GR concentration)

| Agent | (GR)$_1$ | (GR)$_2$ | (GR)$_3$ | (GR)$_4$ | (GR)$_5$ | (GR)$_6$ | (GR)$_8$ | (GR)$_{10}$ |
|---|---|---|---|---|---|---|---|---|
| Buffer + DTT - in solution - 5 min reaction | 0.0 | 0.0 | 0.0 | 0.0 | 0.0 | 0.0 | 5.5 | 308.6 |
| Buffer + DTT - in solution - 60 min reaction | 0.6 | 0.0 | 0.0 | 0.0 | 0.0 | 0.0 | 0.0 | 282.6 |

Example 3.5. Cleavage of (GR)$_{10}$ by Different Enzymes Immobilized on Agarose Resin in Cerebrospinal Fluid (CSF)

Figure 5:
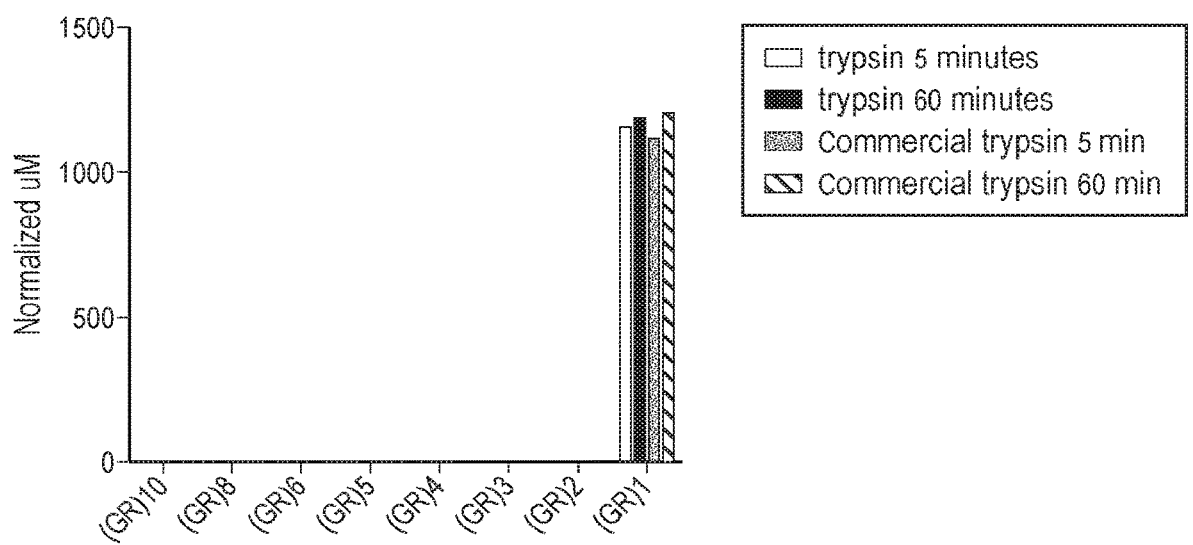
FIG. 5 is a bar graph showing the results of digestion of $(GR)_{10}$ by commercial and in-house immobilized trypsin at 5 and 60 minutes in CSF (normalized).
Figure 6:
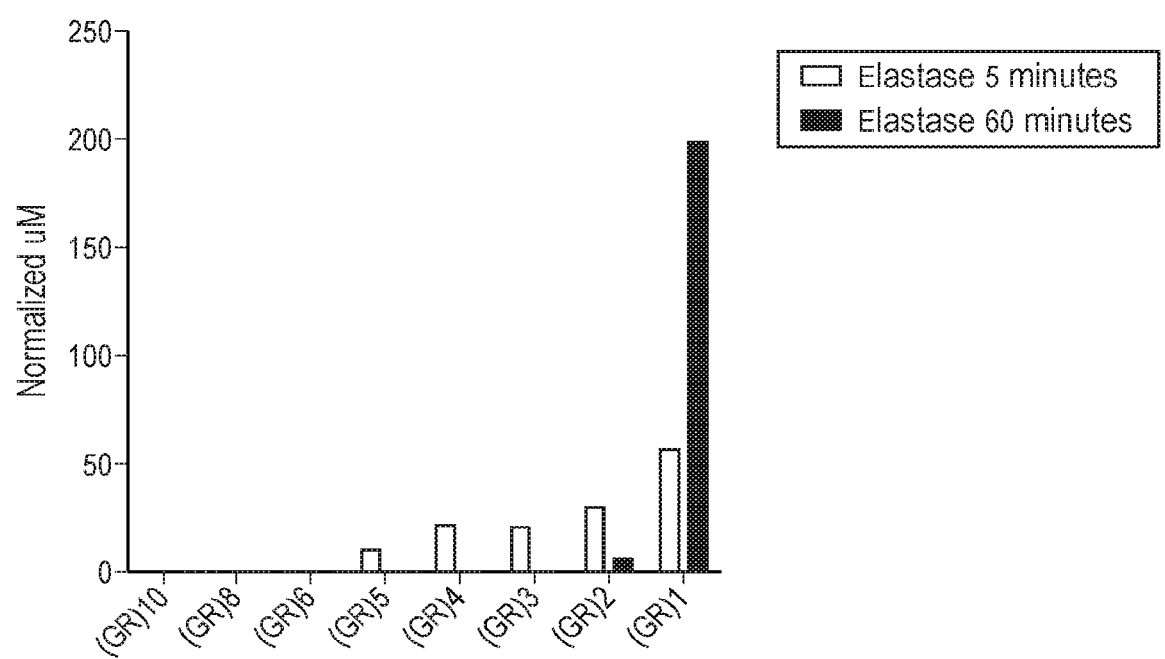
FIG. 6 is a bar graph showing the results of digestion of $(GR)_{10}$ by immobilized elastase at 5 and 60 minutes in CSF (normalized).
Figure 7A:
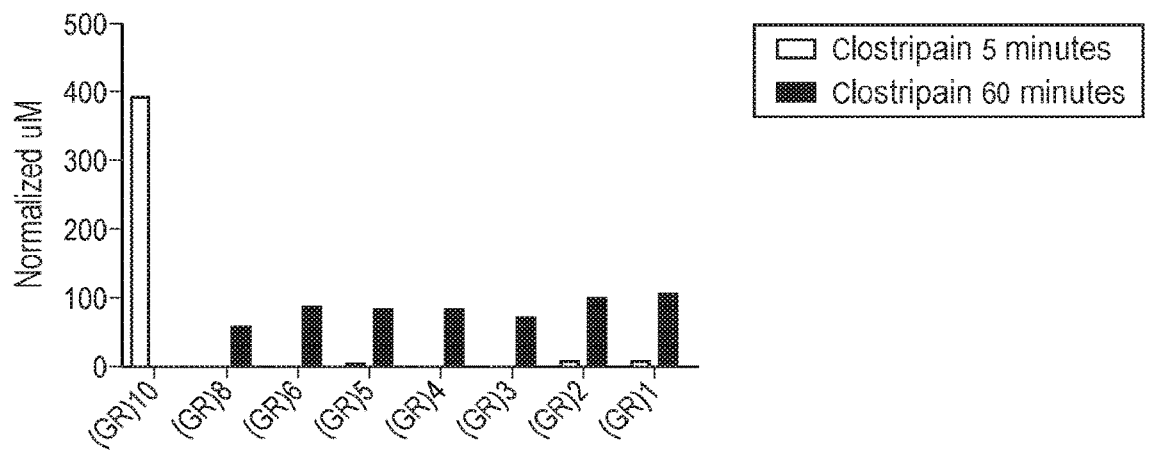
FIGS. 7A and 7B are bar graphs showing the results of digestion of $(GR)_{10}$ by immobilized clostripain at 5 and 60 minutes in CSF (normalized)
Figure 7B:
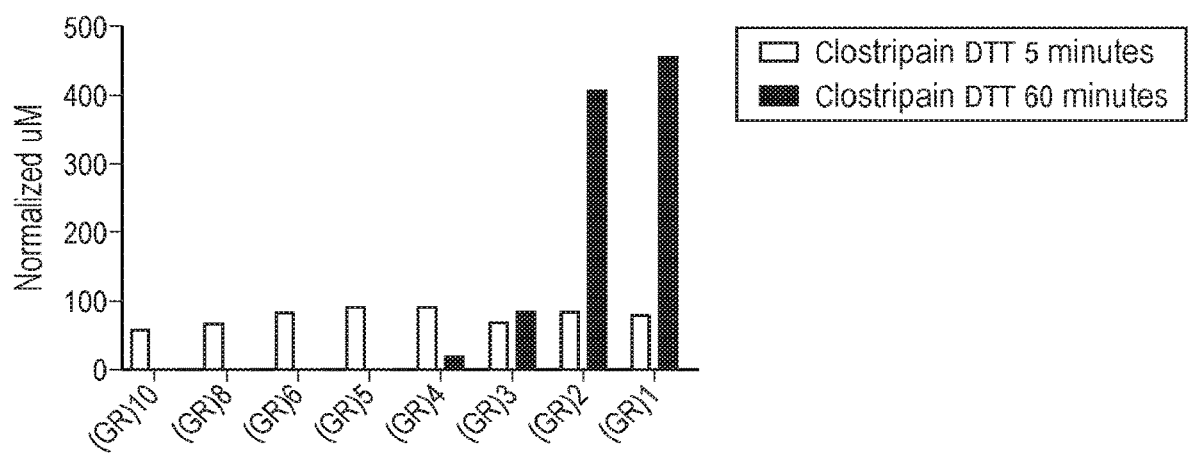

(GR)$_{10}$ was digested with exemplary immobilized enzymes as described above in the subsection titled "(GR)$_{10}$ digestion with immobilized proteases in CSF" of Example 3. Clostripain experiments were conducted with and without DTT activation (no DTT during digestion). The results obtained after 5 and 60 minutes of reaction time are presented in Table 25 and shown in FIG. 5 (commercial and in-house immobilized trypsin), FIG. 6 (immobilized elastase, FIG. 7A (immobilized clostripain without DTT) and FIG. 7 (immobilized clostripain with 2.5 mM DTT).

agarose resins having immobilized trypsin or elastase, PBS alone, or agarose resin alone, for 5 minutes or 60 minutes at room temperature. Resins were prepared by a routine method as commonly used by persons of ordinary skill in the art (e.g., the binding reaction described in the POROS™ 20 AL, EP and OH Perfusion Chromatography Bulk Media for Activated Affinity Chromatography Product Information Sheet, ThermoFisher Scientific, Waltham, Mass., Pub. No. 8-0031-40-0993, Rev. C., (incorporated herein by reference in its entirety)) and stored at 4° C. for over 2 months.

50 µl of treated samples were prepared for LC/MS analysis by adding 2.5 µl of 10% trifluoroacetic acid to each sample and 150 µl of dilution solution (0.5% formic acid in ACN/MeOH [50:50]).

TABLE 25

Cleavage of (GR)$_{10}$ by immobilized clostripain (with 2.5 mM DTT) (normalized uM)

| Agent | (GR)$_1$ | (GR)$_2$ | (GR)$_3$ | (GR)$_4$ | (GR)$_5$ | (GR)$_6$ | (GR)$_8$ | (GR)$_{10}$ |
|---|---|---|---|---|---|---|---|---|
| Resin + DTT - Immobilized - 5 min reaction | 0.0 | 0.0 | 0.0 | 0.0 | 0.0 | 0.0 | 0.0 | 856 |
| Resin alone -5 min reaction | 0.0 | 0.0 | 0.0 | 0.0 | 0.0 | 0.0 | 0.0 | 710 |
| CSF + (GR)$_{10}$ -5 min reaction | 0.0 | 0.0 | 0.0 | 0.0 | 0.0 | 0.0 | 0.0 | 1240 |
| CSF alone - 5 min reaction | 0.0 | 0.0 | 0.0 | 0.0 | 0.0 | 0.0 | 0.0 | 0.0 |
| Trypsin - Immobilized - 5 min reaction | 1153.4 | 9.0 | 0.0 | 0.0 | 0.0 | 0.0 | 0.0 | 0.0 |
| Commercial Trypsin - Immobilized - 5 min reaction | 1117.3 | 0.0 | 0.0 | 0.0 | 0.0 | 0.0 | 0.0 | 0.0 |
| Elastase - Immobilized - 5 min reaction | 57.4 | 29.4 | 20.7 | 22 | 10.5 | 0.0 | 0.0 | 0.0 |
| Clostripain - Immobilized - 5 min reaction | 11.2 | 10.0 | 0.0 | 0.0 | 8.5 | 0.0 | 0.0 | 395 |
| Clostripain + DTT - Immobilized - 5 min reaction | 79.8 | 83.2 | 70.5 | 90.8 | 90.5 | 86.4 | 64.8 | 58 |
| Resin + DTT - Immobilized - 60 min reaction | 2.2 | 0.0 | 0.0 | 0.0 | 0.0 | 0.0 | 0.0 | 803 |
| Resin alone -60 min reaction | 2.6 | 0.0 | 0.0 | 0.0 | 0.0 | 0.0 | 0.0 | 954 |
| CSF + (GR)$_{10}$ -60 min reaction | 1.6 | 0.0 | 0.0 | 0.0 | 0.0 | 0.0 | 0.0 | 1307 |
| CSF alone - 560 min reaction | 0.0 | 0.0 | 0.0 | 0.0 | 0.0 | 0.0 | 0.0 | 0.0 |
| Trypsin - Immobilized - 60 min reaction | 1182.3 | 0.0 | 0.0 | 0.0 | 0.0 | 0.0 | 0.0 | 0.0 |
| Commercial Trypsin - Immobilized - 605 min reaction | 1197.4 | 0.0 | 0.0 | 0.0 | 0.0 | 0.0 | 0.0 | 0.0 |
| Elastase - Immobilized - 605 min reaction | 200.3 | 6 | 0.0 | 0.0 | 0.0 | 0.0 | 0.0 | 0.0 |
| Clostripain - Immobilized - 60 min reaction | 106.2 | 99.2 | 72.3 | 84.7 | 85.5 | 87 | 58.4 | 0 |
| Clostripain + DTT - Immobilized - 60 min reaction | 458.3 | 409.2 | 85.5 | 21.2 | 3 | 0 | 0 | 0 |

Example 3.6—Cleavage of (GR)$_{10}$ by Different Enzymes Immobilized on Agarose Resin and Stored at 4° C. for Over 2 Months This example shows the digestive activity of trypsin or elastase immobilized on agarose resin and stored at 4° C. for over 2 months.

Figure 8A:
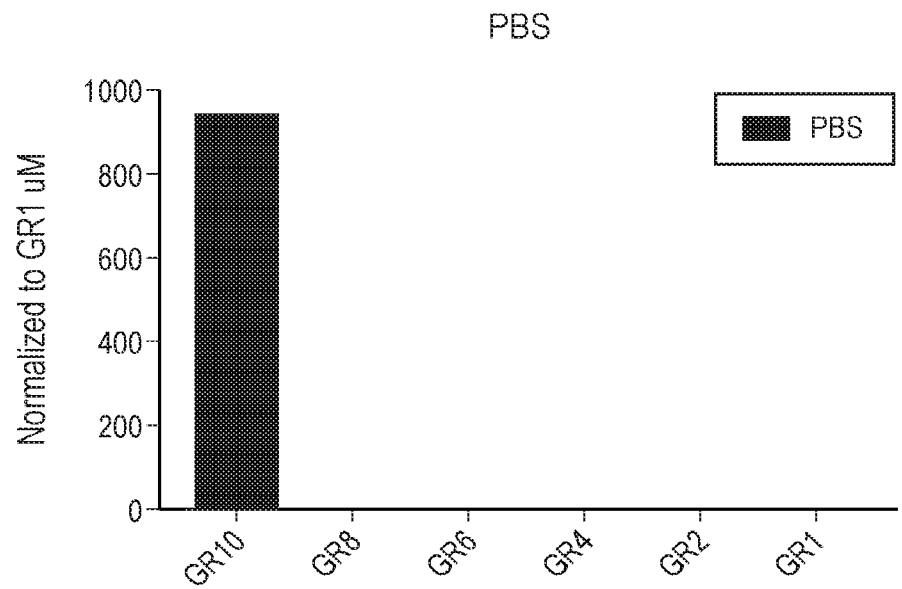
FIGS. 8A-8D are bar graphs showing the results of digestion of $(GR)_{10}$ by immobilized proteases after storage for over 2 months at 4° C.
Figure 8B:
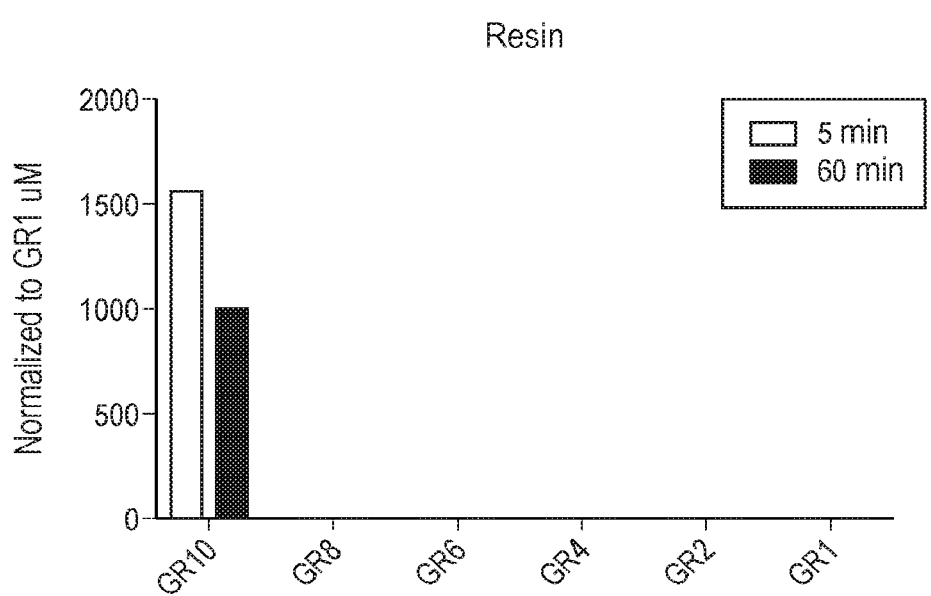
Figure 8C:
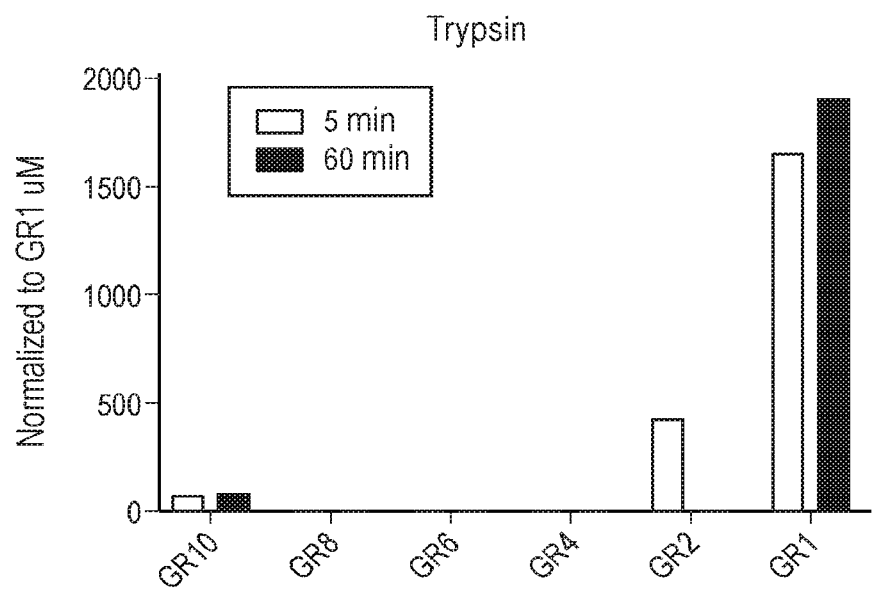
Figure 8D:
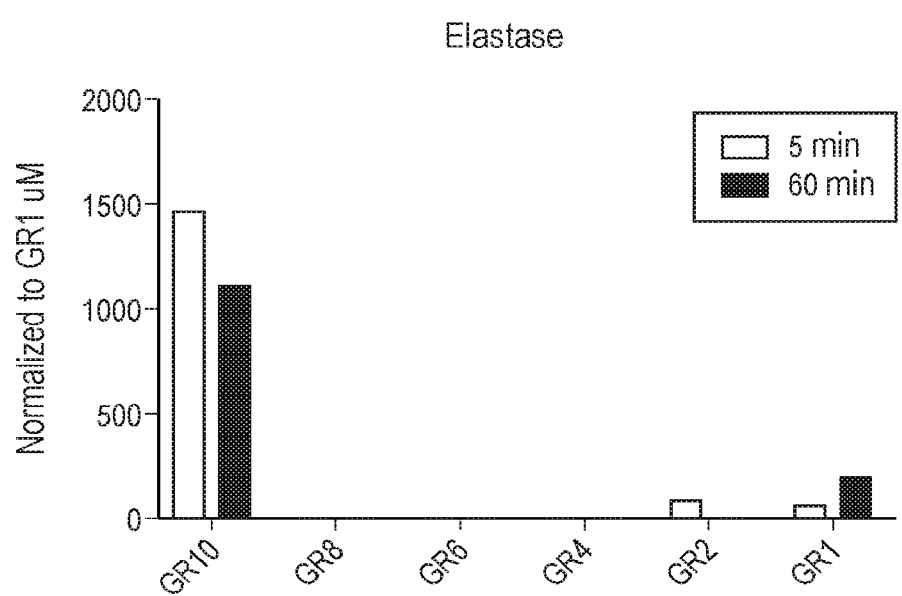

(GR)$_{10}$ was prepared in water to a stock concentration of 10 mM then diluted to a concentration of 200 µM in PBS with Ca$^{2+}$ and Mg$^{2+}$. (GR)$_{10}$ samples were then treated with As shown in FIGS. 8A and 8B, (GR)$_{10}$ samples treated with PBS alone, or agarose resin alone, did not result in degradation of (GR)$_{10}$. As seen in FIG. 8C, agarose resin having immobilized trypsin exhibited proteolytic activity after storage at 4° C. for over 2 months. However, as shown in FIG. 8D, under these specific storage and reaction conditions, agarose resin having immobilized elastase did not exhibit substantial (GR)$_{10}$ proteolytic activity at either 5 minute or 60 minute treatment times.

Example 3.7—Cleavage of Tagged $(GR)_{10}$ by Different Enzymes Immobilized on Agarose Resin This example shows the digestive activity of trypsin or elastase immobilized on agarose resin on biotin-$(PEG)_4$-tagged $(GR)_{10}$.

Biotin-$(PEG)_4$-$(GR)_{10}$ was prepared in water to a stock concentration of 10 mM then diluted to a concentration of 200 µM in PBS with $Ca^{2+}$ and $Mg^{2+}$. Biotin-$(PEG)_4$-$(GR)_{10}$ samples were then treated with agarose resins having immobilized trypsin or elastase, commercially purchased agarose resins having immobilized trypsin, PBS alone, or agarose resin alone, for 5 minutes or 60 minutes at room temperature. Resins were prepared by a routine method as commonly used by persons of ordinary skill in the art (e.g., the binding reaction described in the POROS™ 20 AL, EP and OH Perfusion Chromatography Bulk Media for Activated Affinity Chromatography Product Information Sheet, ThermoFisher Scientific, Waltham, Mass., Pub. No. 8-0031-40-0993, Rev. C., (incorporated herein by reference in its entirety)).

50 µl of treated samples were prepared for LC/MS analysis by adding 2.5 µl of 10% trifluoroacetic acid to each sample and 150 µl of dilution solution (0.5% formic acid in ACN/MeOH [50:50]).

Figure 9:
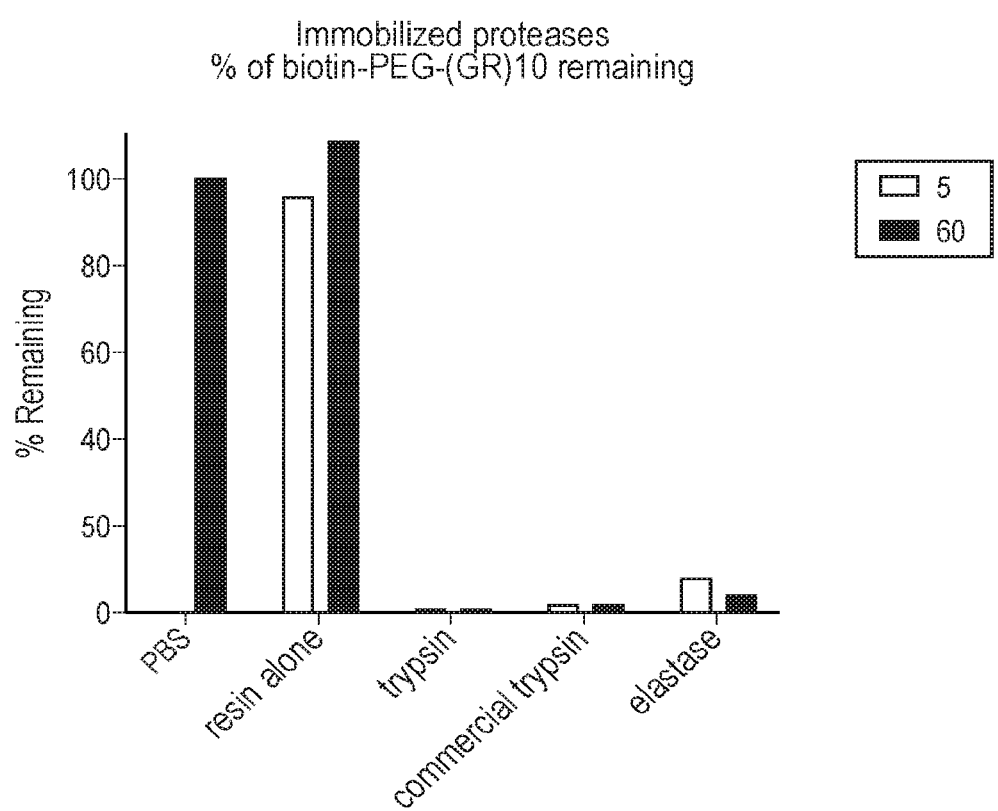
FIG. 9 is a bar graph showing the results of digestion of biotin-$(PEG)_4$-$(GR)_{10}$ by in-house and commercial immobilized trypsin and immobilized elastase.

As shown in FIG. 9, biotin-$(PEG)_4$-$(GR)_{10}$ samples treated with PBS alone, or agarose resin alone, did not result in degradation of tagged-$(GR)_{10}$. However, treatment of samples with agarose resins having immobilized trypsin or elastase, or commercially purchased agarose resin having immobilized trypsin, resulted in over 90% digestion of biotin-$(PEG)_4$-$(GR)_{10}$ after only 5 minutes of incubation time. Resins were prepared by a routine method as commonly used by persons of ordinary skill in the art (e.g., the binding reaction described in the POROS™ 20 AL, EP and OH Perfusion Chromatography Bulk Media for Activated Affinity Chromatography Product Information Sheet, ThermoFisher Scientific, Waltham, Mass., Pub. No. 8-0031-40-0993, Rev. C., (incorporated herein by reference in its entirety)).

Example 3.8—Reduced Toxicity of $(GR)_{10}$ by Treatment with Proteases

This example describes the reduced toxicity of $(GR)_{10}$ on in vitro neuronal cells by digestion of $(GR)_{10}$ with proteases.

Treatment of commercially available iCell® motor neurons (FUJIFILM Cellular Dynamics, Inc., Madison, Wis.) with synthetic $(GR)_{10}$ resulted in dose-dependent toxicity with an $EC_{50}$ of approximately 50 µM. Toxicity was further enhanced when $(GR)_{10}$ was dissolved in DMSO instead of water.

Samples of $(GR)_{10}$ treated with agarose resin alone (as described in Example 3.6) similarly resulted in dose-dependent toxicity of iCell® motor neurons. Treatment of $(GR)_{10}$ with resins having immobilized trypsin, elastase, or clostripain resulted in abrogation of $(GR)_{10}$ toxicity on iCell® motor neurons at $(GR)_{10}$ concentrations of 25, 50 and 100 µM.

Example 4. Cleavage of GA Dipeptide Repeats by Exemplary Enzymes in Solution Reagents:

$(GA)_1$ to $(GA)_{10}$ peptides were synthetized by solid-phase synthesis by Peptide2.0; All peptides are uncapped and supplied lyophilized with TFA as counter ions. Purity was always above 95%.

Buffer: PBS buffer containing $CaCl_2$ and $MgCl_2$.

Stock solution of enzyme (e.g., 10 mg/mL) (prepared per manufacturer instructions) in PBS. Activators added as necessary.

Working solution of protein of the desired concentration (e.g., 33 µg/mL) prepared immediately before use by diluting the stock solution (e.g., 33 µL of 10 mg/mL stock solution) in PBS buffer (e.g., in 967 µL of PBS).

Exemplary Procedure Using 50 µM Concentrations of $(GA)_{10}$

50 µL of a 100 µM solution of $(GA)_{10}$ was added to each well of a 96-well plate. 50 µL of a solution of enzyme (two times the desired final enzyme concentration) was added, and the plates were incubated at room temperature. At the specified time points (2 minutes, 5 minutes, 10 minutes, 30 minutes, 60 minutes and 180 minutes) 900 µL of D1 solution (50/20/20/10/0.1 of acetonitrile/water/DMSO/trifluoroethanol/BSA) were added to stop the reaction. For the time 0 minute well, the D1 solution was added to the well before addition of the enzyme. After last time point, plate was centrifuged 2 minutes at 1000 rpm and 600 µL of supernatant transferred to clean wells. The quenched reaction mixtures were analyzed by LC/MS to determine the concentration of GA repeats of different lengths.

Detection

The chromatography and mass spectrometry conditions utilized are shown in Table 26 and Table 27, respectively.

Figure 10A:
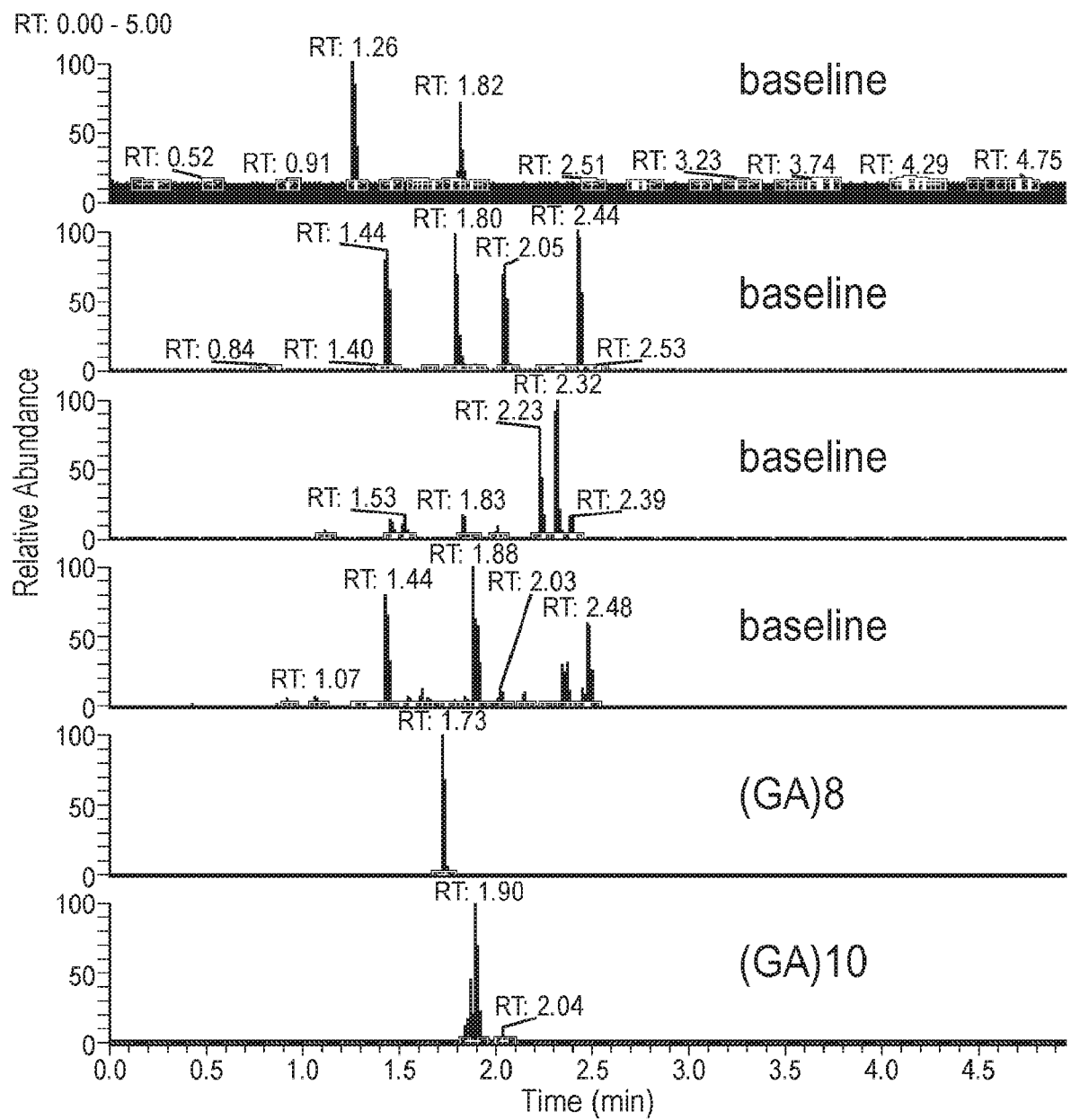
FIGS. 10A-10C are LC/MS profiles showing results from the digestion of $(GA)_{10}$ by 33 µg/mL and 330 µg/mL of elastase.
Figure 10B:
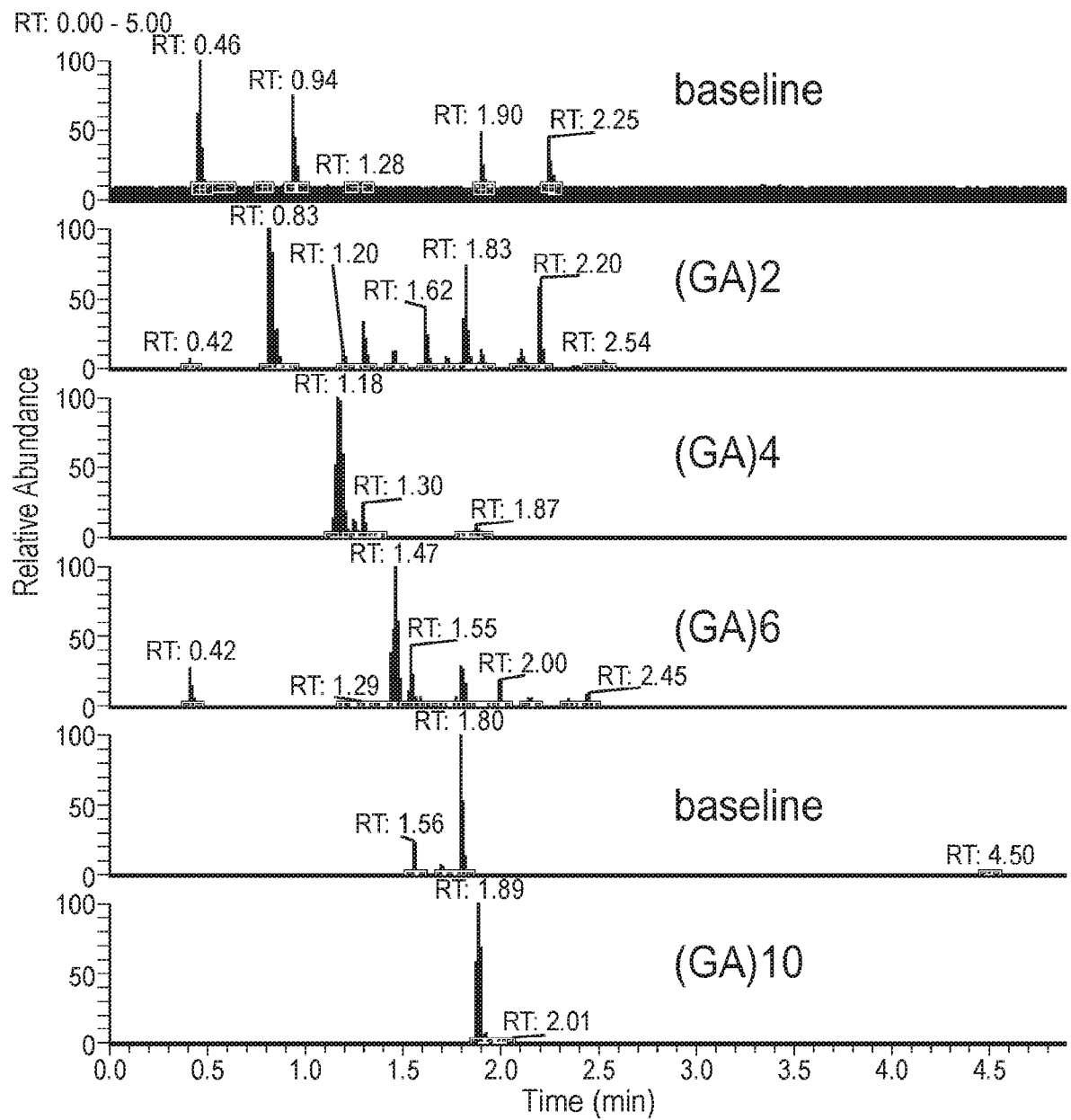
Figure 10C:
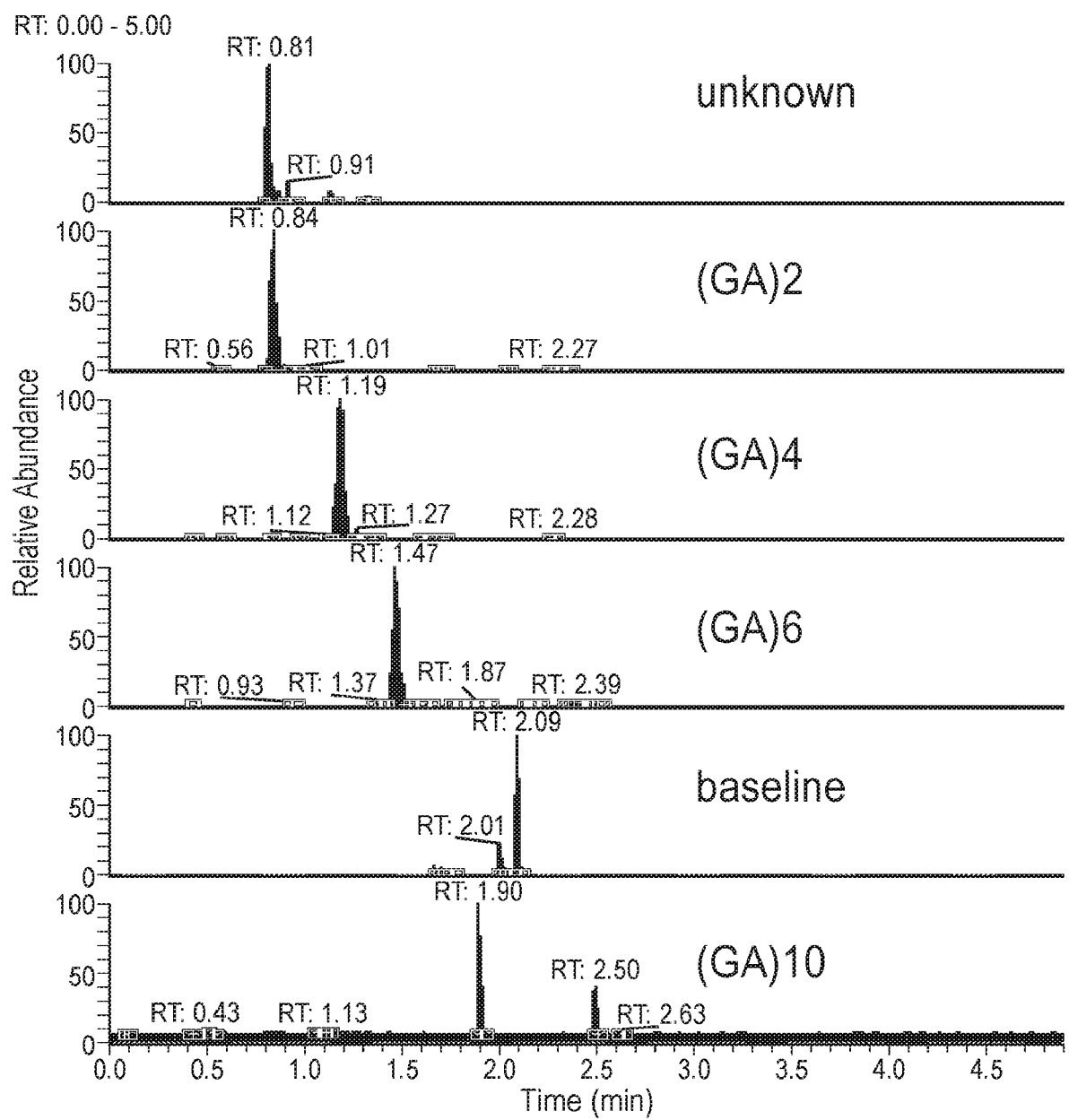

Example 4.1. Cleavage of Various Concentrations of $(GA)_{10}$ by 330 µg/mL and 33 µg/mL Elastase Solutions Digestion of $(GA)_{10}$ (50 µM) by elastase 330 µg/mL and 33 µg/mL was performed as described above. The results for 33 µg/mL and 330 µg/mL elastase at 60 minutes are shown in FIGS. 1A-10C (FIG. 10A—no elastase; FIG. 10B 33 µg/mL elastase; FIG. 10C 330 µg/mL elastase).

TABLE 26

| HPLC conditions for detecting GA repeats of different lengths: | |
|---|---|
| LC/MS System | Thermo Accela UPLC/TSQ Quantum Ultra |
| Column | Waters Xbridge Amide 2.1X50 mm, 3.5 µm |
| Injection Volume | 2 µL |
| Temperature | 45° C. |
| Gradient | |
| Mobile phase A | 0.2% FA in water |
| Mobile phase B | 0.2% FA in acetonitrile |

| Time (Min) | % A | % B | Flow rate (µL/min) |
|---|---|---|---|
| 0 | 5 | 95 | 600 |
| 2.5 | 30 | 70 | 600 |
| 2.6 | 5 | 95 | 1000 |
| 5 | 5 | 95 | 1000 |

TABLE 27

| Mass spectrometry conditions for detecting GA repeats of different lengths | | | | |
|---|---|---|---|---|
| Name | Precursor ion | Product Ion | CE | Tube Lens |
| $(GA)_1$ | 147.0 | 90.0 | 5 | 59 |
| $(GA)_2$ | 275.1 | 147.0 | 10 | 82 |

TABLE 27-continued

Mass spectrometry conditions for detecting GA repeats of different lengths

| Name | Precursor ion | Product Ion | CE | Tube Lens |
|---|---|---|---|---|
| $(GA)_4$ | 531.1 | 212.0 | 32 | 107 |
| $(GA)_6$ | 787.1 | 211.9 | 49 | 128 |
| $(GA)_8$ | 1043.2 | 495.1 | 44 | 145 |
| $(GA)_{10}$ | 1299.6 | 495.1 | 54 | 195 |
| | | 623.2 | 49 | 195 |
| | | 751.4 | 48 | 195 |

Example 4.2. Cleavage of $(GA)_{10}$ by Elastase Immobilized on Agarose Resin

This example describes a method of monitoring the digestive activity of elastase immobilized on agarose resin on $(GA)_{10}$.

Elastase can be immobilized on NETS-activated agarose resin by a routine method as commonly used by persons of ordinary skill in the art (e.g., the binding reaction described in the POROS™ 20 AL, EP and OH Perfusion Chromatography Bulk Media for Activated Affinity Chromatography Product Information Sheet, ThermoFisher Scientific, Waltham, Mass., Pub. No. 8-0031-40-0993, Rev. C., (incorporated herein by reference in its entirety)). $(GA)_{10}$ can be prepared as previously described in Chang et al. (2016) *J Biol Chem;* 291(10):4903-11, herein incorporated by reference in its entirety. In brief, $(GA)_{10}$ can be dissolved in hexafluoroisopropanol to a concentration of 4 mg/ml (2 mM) and incubated at room temperature for 2 hours. The hexafluoroisopropanol can then be evaporated under vacuum. $(GA)_{10}$ may then be dissolved in dichloroacetic acid and further diluted in 100 mM phosphatase buffer and pH adjusted to 7.4.$(GA)_{10}$ can be treated with immobilized elastase for 5 and 60 minutes, and digestion products analyzed by LC/MS as described above.

Numbered Embodiments

Embodiments disclosed herein include embodiments P1 to P174, as provided in the numbered embodiments of the disclosure:

Embodiment P1: A method for treating a subject suffering from a neurological disorder characterized by the presence of toxic proteins comprising contacting the cerebrospinal fluid (CSF) of the subject with an agent capable of removing or degrading the toxic protein.

Embodiment P2: The method of embodiment P1, wherein the toxic protein is a dipeptide repeat protein possessing 2 or more dipeptide repeats.

Embodiment P3: The method of embodiment P2, wherein the dipeptide repeat is selected from glycine-alanine (GA), glycine-arginine (GR), alanine-proline (AP), glycine-proline (GP) and proline-arginine (PR) wherein the order of the two amino acids comprising the dipeptide repeat can be reversed.

Embodiment P4: The method of embodiment P3, wherein the dipeptide repeat is glycine-arginine (GR).

Embodiment P5: The method of embodiment P3, wherein the dipeptide repeat is glycine-alanine (GA).

Embodiment P6: The method of any one of embodiments P2 to P5, wherein the dipeptide repeat protein possesses 2 or more dipeptide repeats.

Embodiment P7: The method of embodiment P6, wherein the dipeptide repeat protein possesses 4 or more dipeptide repeats.

Embodiment P8: The method of embodiment P6, wherein the dipeptide repeat protein possesses 6 or more dipeptide repeats.

Embodiment P9: The method of embodiment P6, wherein the dipeptide repeat protein possesses 8 or more dipeptide repeats.

Embodiment P10: The method of embodiment P6, wherein the dipeptide repeat protein possesses 10 or more dipeptide repeats.

Embodiment P11: The method of embodiment P6, wherein the dipeptide repeat protein possesses 75 or more dipeptide repeats.

Embodiment P12: The method of embodiment P6, wherein the dipeptide repeat protein possesses 150 or more dipeptide repeats.

Embodiment P13: The method of embodiment P6, wherein the dipeptide repeat protein possesses 700 or more dipeptide repeats.

Embodiment P14: The method of any one of embodiments P1 to P13, wherein the neurological disorder is characterized by a chromosome 9 open reading frame 72 (C9orf72) mutation (i.e., a C9orf72 positive neurological disease).

Embodiment P15: The method of embodiment P14, wherein the neurological disorder is selected from the group consisting of C9orf72 positive amyotrophic lateral sclerosis (ALS), C9orf72 positive frontotemporal dementia (FTD), C9orf72 positive frontotemporal lobar degeneration (FTLD).

Embodiment P16: The method of any one of embodiments P1 to P15, wherein the agent is an enzyme.

Embodiment P17: The method of embodiment P16, wherein the enzyme is a protease.

Embodiment P18: The method of embodiment P17, wherein the protease is able to reduce the concentration of toxic protein (e.g., dipeptide repeat proteins) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P19: The method of embodiment P17 or P18, wherein the protease can reduce the concentration of toxic proteins (e.g., dipeptide proteins) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P20: The method of any one of embodiments P17 to P19, wherein the protease is characterized by an active site capable of selectively recognizing the peptide sequence of the toxic protein over other proteins normally occurring in the CSF and is further capable of specific cleavage of at least one peptide bond of the toxic protein over cleavage of peptide bonds of proteins normally occurring in the CSF.

Embodiment P21: The method of embodiment P20, wherein the toxic protein is a dipeptide repeat protein and the protease is characterized by an active site capable of selectively recognizing the dipeptide sequence of the dipeptide repeat protein over other proteins normally occurring in the CSF and is further capable of specific cleavage of the peptide bond of the dipeptide sequence over cleavage of peptide bonds of proteins normally occurring in the CSF.

Embodiment P22: The method of any one of embodiments P17 to P21, wherein the protease is characterized by an active site capable of specific cleavage at positively charged P1 or P1' residues.

Embodiment P23: The method of embodiment P22, wherein the protease is characterized by an active site capable of specific cleavage at P1 or P1' arginine residues.

Embodiment P24: The method of any one of embodiments P17 to P23, wherein the protease is characterized by an active site capable of specific cleavage at P1 or P1' proline residues.

Embodiment P25: The method of any one of embodiments P17 to P24, wherein the protease is characterized by an active site capable of specific cleavage at small hydrophobic P1 or P1' residues.

Embodiment P26: The method of embodiment P25, wherein the protease is characterized by an active site capable of specific cleavage at P1 or P1' alanine residues.

Embodiment P27: The method of embodiment P25, wherein the protease is characterized by an active site capable of specific cleavage at P1 or P1' valine residues.

Embodiment P28: The method of any one of embodiments P17 to P27, wherein the protease is selected from the group consisting of trypsin, thrombin, proteinase K, elastase, Factor Xa, kallikreins (e.g., kallikrein-6 or kallikrein-5), clostripains, calpains, cathepsins (e.g., cathepsin-B) and thermolysin.

Embodiment P29: The method of embodiment P28, wherein the protease is trypsin.

Embodiment P30: The method of embodiment P28, wherein the protease is elastase.

Embodiment P31: The method of embodiment P28, wherein the protease is clostripain.

Embodiment P32: The method of embodiment P31, wherein the clostripain is not activated with a reducing agent.

Embodiment P33: The method of any one of embodiments P17 to P32, wherein the protease is capable of effecting the degradation of the toxic proteins (e.g., dipeptide repeat proteins) without significant effects on the concentration of proteins naturally occurring in the CSF.

Embodiment P34: The method of any one of embodiments P17 to P33, wherein the protease has higher specificity and lower affinity for the toxic proteins (e.g., dipeptide repeat proteins) compared to proteins normally occurring in the CSF.

Embodiment P35: The method of any one of embodiments P17 to P33, wherein the protease has higher specificity and higher affinity for the toxic proteins (e.g., dipeptide repeat proteins) compared to proteins normally occurring in the CSF.

Embodiment P36: The method of any one of embodiments P17 to P35, wherein the protease has higher efficiency cleaving at least one peptide bond of the toxic proteins (e.g., dipeptide repeat proteins) compared to the peptide bonds of proteins normally occurring in the CSF.

Embodiment P37: The method of any one of embodiments P17 to P36, wherein the protease is a protease naturally occurring in CSF.

Embodiment P38: The method of embodiment P37, wherein the protease is a kallikrein.

Embodiment P39: The method of embodiment P38, wherein the kallikrein is kallikrein-6 or kallikrein-5.

Embodiment P40: The method of any one of embodiments P17 to P19, P22 to P32, and P37 to P39, wherein the protease is not selective for the degradation of toxic proteins (e.g., dipeptide repeat proteins) over other proteins normally occurring in the CSF.

Embodiment P41: The method of any one of embodiments P1 to P40 comprising a step of removing the CSF from the subject prior to contacting it with the agent and a step of reintroducing the CSF back into the subject after contacting it with the agent; or the method comprising contacting the CSF of the subject to an agent immobilized to a solid surface or support in a device implanted into the body of the subject, optionally wherein the agent or the agent immobilized to the solid surface or support is extracted and reintroduced to the implanted device during treating the subject for over an extended period of time, optionally wherein the extended period is an intermittent period of 2-12 months.

Embodiment P42: The method of embodiment P41, wherein the agent is immobilized (e.g., the agent is a protease immobilized on a solid substrate).

Embodiment P43: The method of embodiment P42, wherein the agent (e.g., the protease) is immobilized on a solid support.

Embodiment P44: The method of embodiment P43, wherein the solid support is a porous solid support.

Embodiment P45: The method of embodiment P43 or P44, wherein the agent (e.g., the protease) is attached to the support by covalent binding.

Embodiment P46: The method of any one of embodiments P43 to P45, wherein the support is a cross-linked resin.

Embodiment P47: The method of embodiment P46, wherein the cross-linked resin is an agarose resin.

Embodiment P48: The method of embodiment P42, wherein the agent is immobilized by cross-linking to porous beads or membranes (e.g., the agent is a protease cross-linked to porous beads or membranes).

Embodiment P49: The method of embodiment P42, wherein the agent is immobilized by precipitation (e.g., as an amorphous or crystalline precipitate).

Embodiment P50: The method of embodiment P49, wherein the precipitated agent is cross-linked (e.g., to form a cross-linked amorphous or crystalline precipitate, e.g., cross-linked protease crystals, e.g., cross-linked amorphous protease precipitate).

Embodiment P51: The method of embodiment P42, wherein the agent is lyophilized to form a dry powder and the powder is placed inside a porous coating to form beads.

Embodiment P52: The method of any one of embodiments P41 to P51 further comprising a step of filtering the CSF prior to reintroducing the CSF back into the subject.

Embodiment P53: The method of any one of embodiments P1 to P40, wherein the agent is directly introduced into the CSF of the subject.

Embodiment P54: A composition comprising: (a) cerebrospinal fluid (CSF) of a subject suffering from a neurological disorder characterized by the production of toxic proteins; and (b) an agent capable of degrading or removing the toxic proteins.

Embodiment P55: The composition of embodiment P54, wherein the toxic protein is a dipeptide repeat protein possessing 2 or more dipeptide repeats.

Embodiment P56: The composition of embodiment P55, wherein the dipeptide repeat is selected from glycine-alanine (GA), glycine-arginine (GR), alanine-proline (AP), glycine-proline (GP) and proline-arginine (PR) wherein the order of the two amino acids comprising the dipeptide repeat can be reversed.

Embodiment P57: The composition of embodiment P56, wherein the dipeptide repeat is glycine-arginine (GR).

Embodiment P58: The composition of embodiment P56, wherein the dipeptide repeat is glycine-alanine (GA).

Embodiment P59: The composition of any one of embodiments P54 to P56, wherein the dipeptide repeat protein possesses 2 or more dipeptide repeats.

Embodiment P60: The composition of embodiment P59, wherein the dipeptide repeat protein possesses 4 or more dipeptide repeats.

Embodiment P61: The composition of embodiment P59, wherein the dipeptide repeat protein possesses 6 or more dipeptide repeats.

Embodiment P62: The composition of embodiment P59, wherein the dipeptide repeat protein possesses 8 or more dipeptide repeats.

Embodiment P63: The composition of embodiment P59, wherein the dipeptide repeat protein possesses 10 or more dipeptide repeats.

Embodiment P64: The composition of embodiment P59, wherein the dipeptide repeat protein possesses 75 or more dipeptide repeats.

Embodiment P65: The composition of embodiment P59, wherein the dipeptide repeat protein possesses 150 or more dipeptide repeats.

Embodiment P66: The composition of embodiment P59, wherein the dipeptide repeat protein possesses 700 or more dipeptide repeats.

Embodiment P67: The composition of embodiment P54 to P66, wherein the neurological disorder is characterized by a chromosome 9 open reading frame 72 (C9orf72) mutation (i.e., a C9orf72 positive neurological disease).

Embodiment P68: The composition of embodiment P67, wherein the neurological disorder is selected from the group consisting of C9orf72 positive amyotrophic lateral sclerosis (ALS), C9orf72 positive frontotemporal dementia (FTD), C9orf72 positive frontotemporal lobar degeneration (FTLD).

Embodiment P69: The composition of any one of embodiments P54 to P68, wherein the agent is an enzyme.

Embodiment P70: The composition of embodiment P69, wherein the enzyme is a protease.

Embodiment P71: The composition of embodiment P70, wherein the protease is able to reduce the concentration of toxic protein (e.g., dipeptide repeat proteins) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P72: The composition of embodiment P70 or P71, wherein the protease can reduce the concentration of toxic proteins (e.g., dipeptide proteins) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P73: The composition of any one of embodiments P70 to P72, wherein the protease is characterized by an active site capable of selectively recognizing the peptide sequence of the toxic protein over other proteins normally occurring in the CSF and is further capable of specific cleavage of at least one peptide bond of the toxic protein over cleavage of peptide bonds of proteins normally occurring in the CSF.

Embodiment P74: The composition of embodiment P73, wherein the toxic protein is a dipeptide repeat protein and the protease is characterized by an active site capable of selectively recognizing the dipeptide sequence of the dipeptide repeat protein over other proteins normally occurring in the CSF and is further capable of specific cleavage of the peptide bond of the dipeptide sequence over cleavage of peptide bonds of proteins normally occurring in the CSF.

Embodiment P75: The composition of any one of embodiments P70 to P74, wherein the protease is characterized by an active site capable of specific cleavage at positively charged P1 or P1' residues.

Embodiment P76: The composition of embodiment P75, wherein the protease is characterized by an active site capable of specific cleavage at P1 or P1' arginine residues.

Embodiment P77: The composition of any one of embodiments P70 to P76, wherein the protease is characterized by an active site capable of specific cleavage at P1 or P1' proline residues.

Embodiment P78: The composition of any one of embodiments P70 to P77, wherein the protease is characterized by an active site capable of specific cleavage at small hydrophobic P1 or P1' residues.

Embodiment P79: The composition of embodiment P78, wherein the protease is characterized by an active site capable of specific cleavage at P1 or P1' alanine residues.

Embodiment P80: The composition of embodiment P78, wherein the protease is characterized by an active site capable of specific cleavage at P1 or P1' valine residues.

Embodiment P81: The composition of embodiment P70 to P80, wherein the protease is selected from the group consisting of trypsin, thrombin, proteinase K, elastase, Factor Xa, kallikreins (e.g., kallikrein-6 or kallikrein-5), clostripains, calpains, cathepsins (e.g., cathepsin-B) and thermolysin.

Embodiment P82: The composition of embodiment P81, wherein the protease is trypsin.

Embodiment P83: The composition of embodiment P81, wherein the protease is elastase.

Embodiment P84: The composition of embodiment P81, wherein the protease is clostripain.

Embodiment P85: The composition of embodiment P84, wherein the clostripain is not activated with a reducing agent.

Embodiment P86: The composition of any one of embodiments P70 to P85, wherein the protease is capable of effecting the degradation of the toxic proteins (e.g., dipeptide repeat proteins) without significant effects on the concentration of proteins naturally occurring in the CSF.

Embodiment P87: The composition of any one of embodiments P70 to P86, wherein the protease has higher specificity and lower affinity for the toxic proteins (e.g., dipeptide repeat proteins) compared to proteins normally occurring in the CSF.

Embodiment P88: The composition of any one of embodiments P70 to P86, wherein the protease has higher specificity and higher affinity for the toxic proteins (e.g., dipeptide repeat proteins) compared to proteins normally occurring in the CSF.

Embodiment P89: The composition of any one of embodiments P70 to P88, wherein the protease has higher efficiency cleaving at least one peptide bond of the toxic proteins (e.g., dipeptide repeat proteins) compared to the peptide bonds of proteins normally occurring in the CSF.

Embodiment P90: The composition of any one of embodiments P70 to P89, wherein the protease is a protease naturally occurring in CSF.

Embodiment P91: The composition of embodiment P90, wherein the protease is a kallikrein.

Embodiment P92: The composition of embodiment P90, wherein the kallikrein is kallikrein-6 or kallikrein-5.

Embodiment P93: The composition of any one of embodiments P70 to P72, P75 to P85, and P90 to P91, wherein the protease is not selective for the degradation of toxic proteins (e.g., dipeptide repeat proteins) over other proteins normally occurring in the CSF.

Embodiment P94: The composition of any one of embodiments P54 to P93, wherein the agent is immobilized (e.g., the agent is a protease immobilized on a solid substrate).

Embodiment P95: The composition of embodiment P94, wherein the agent (e.g., the protease) is immobilized on a solid support.

Embodiment P96: The composition of embodiment P95, wherein the solid support is a porous solid support.

Embodiment P97: The composition of embodiment P95 or P96, wherein the agent (e.g., the protease) is attached to the solid support by covalent binding.

Embodiment P98: The composition of any one of embodiments P94 to P97, wherein the solid support is a cross-linked resin.

Embodiment P99: The composition of embodiment P98, wherein the cross-linked resin is an agarose resin.

Embodiment P100: The composition of embodiment P94, wherein the agent is immobilized by cross-linking to porous beads or membranes (e.g., the agent is a protease cross-linked to porous beads or membranes).

Embodiment P101: The composition of embodiment P94, wherein the agent is immobilized by precipitation (e.g., as an amorphous or crystalline precipitate).

Embodiment P102: The composition of embodiment P101, wherein the precipitated agent is cross-linked (e.g., to form a cross-linked amorphous or crystalline precipitate, e.g., cross-linked protease crystals, e.g., cross-linked amorphous protease precipitate).

Embodiment P103: The composition of embodiment P94, wherein the agent is lyophilized to form a dry powder and the powder is placed inside a porous coating to form beads.

Embodiment P104: A method of diagnosing and treating a subject suffering from a neurological disorder characterized by the production of toxic proteins, the method comprising: (a) receiving information regarding the presence of toxic proteins in the cerebrospinal fluid of the subject or receiving information regarding C9orf72 status of a subject and if the subject has been determined to have toxic proteins in the CSF, or if the subject has been determined to be C9orf72 positive diagnosing the subject as susceptible to the treatment of step (b); and (b) treating the subject diagnosed as susceptible in step a) by contacting the cerebrospinal fluid (CSF) of the subject with an agent (e.g., an enzyme, e.g., a protease) capable of removing or degrading the toxic proteins.

Embodiment P105: The method of embodiment P104, wherein the C9orf72 status of a subject is determined by analyzing a biological sample from the subject.

Embodiment P106: The method of embodiment P105, wherein the biological sample is a blood sample.

Embodiment P107: The method of embodiments P105 or P106, wherein the biological sample is analyzed for the presence of mutations in the C9orf72 gene.

Embodiment P108: The method of embodiment P104, wherein if the subject's status has been determined to be C9orf72 positive, step (a) of the method further comprises receiving information regarding the presence of toxic proteins in the CSF of the subject, and if the subject has been determined to have toxic proteins in the CSF, diagnosing the subject to be susceptible to the treatment of step (b).

Embodiment P109: The method of any one of embodiments P104 to P108, wherein the toxic protein is a dipeptide repeat protein possessing 2 or more dipeptide repeats.

Embodiment P110: The method of embodiment P109, wherein the dipeptide repeat is selected from glycine-alanine (GA), glycine-arginine (GR), alanine-proline (AP), glycine-proline (GP) and proline-arginine (PR) wherein the order of the two amino acids comprising the dipeptide repeat can be reversed.

Embodiment P111: The method of embodiment P110, wherein the dipeptide repeat is glycine-arginine (GR).

Embodiment P112: The method of embodiment P110, wherein the dipeptide repeat is glycine-alanine (GA).

Embodiment P113: The method of any one of embodiments P110 to P112, wherein the dipeptide repeat protein possesses 2 or more dipeptide repeats.

Embodiment P114: The method of embodiment P113, wherein the dipeptide repeat protein possesses 4 or more dipeptide repeats.

Embodiment P115: The method of embodiment P113, wherein the dipeptide repeat protein possesses 6 or more dipeptide repeats.

Embodiment P116: The method of embodiment P113, wherein the dipeptide repeat protein possesses 8 or more dipeptide repeats.

Embodiment P117: The method of embodiment P113, wherein the dipeptide repeat protein possesses 10 or more dipeptide repeats.

Embodiment P118: The method of embodiment P113, wherein the dipeptide repeat protein possesses 75 or more dipeptide repeats.

Embodiment P119: The method of embodiment P113, wherein the dipeptide repeat protein possesses 150 or more dipeptide repeats.

Embodiment P120: The method of embodiment P113, wherein the dipeptide repeat protein possesses 700 or more dipeptide repeats.

Embodiment P121: The method of any one of embodiments P104 to P120, wherein the agent is an enzyme.

Embodiment P122: The method of embodiment P121, wherein the enzyme is a protease.

Embodiment P123: The method of embodiment P122, wherein the protease is able to reduce the concentration of toxic protein (e.g., dipeptide repeat proteins) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P124: The method of embodiment P122 or P123, wherein the protease can reduce the concentration of toxic proteins (e.g., dipeptide proteins) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P125: The method of embodiment P122 to P124, wherein the protease is characterized by an active site capable of selectively recognizing the peptide sequence of the toxic protein over other proteins normally occurring in the CSF and is further capable of specific cleavage of at least one peptide bond of the toxic protein over cleavage of peptide bonds of proteins normally occurring in the CSF.

Embodiment P126: The method of embodiment P125, wherein the toxic protein is a dipeptide repeat protein and the protease is characterized by an active site capable of selectively recognizing the dipeptide sequence of the dipeptide repeat protein over other proteins normally occurring in the CSF and is further capable of specific cleavage of the peptide bond of the dipeptide sequence over cleavage of peptide bonds of proteins normally occurring in the CSF.

Embodiment P127: The method of embodiments P122 to P126, wherein the protease is characterized by an active site capable of specific cleavage at positively charged P1 or P1' residues.

Embodiment P128: The method of embodiment P127, wherein the protease is characterized by an active site capable of specific cleavage at P1 or P1' arginine residues.

Embodiment P129: The method of embodiments P122 to P128, wherein the protease is characterized by an active site capable of specific cleavage at P1 or P1' proline residues.

Embodiment P130: The method of embodiments P122 to P129, wherein the protease is characterized by an active site capable of specific cleavage at small hydrophobic P1 or P1' residues.

Embodiment P131: The method of embodiment P130, wherein the protease is characterized by an active site capable of specific cleavage at P1 or P1' alanine residues.

Embodiment P132: The method of any one of embodiments P122 to P131, wherein the protease is selected from the group consisting of trypsin, thrombin, proteinase K, elastase, Factor Xa, kallikreins (e.g., kallikrein-6 or kallikrein-5), clostripains, calpains, cathepsins (e.g., cathepsin-B) and thermolysin.

Embodiment P133: The method of embodiment P132, wherein the protease is trypsin.

Embodiment P134: The method of embodiment P132, wherein the protease is elastase.

Embodiment P135: The method of embodiment P132, wherein the protease is clostripain.

Embodiment P136: The method of embodiment P135, wherein the clostripain is not activated with a reducing agent.

Embodiment P137: The method of any one of embodiments P122 to P136, wherein the protease is capable of effecting the degradation of the toxic proteins (e.g., dipeptide repeat proteins) without significant effects on the concentration of proteins naturally occurring in the CSF.

Embodiment P138: The method of any one of embodiments P122 to P137, wherein the protease has higher specificity and lower affinity for the toxic proteins (e.g., dipeptide repeat proteins) compared to proteins normally occurring in the CSF.

Embodiment P139: The method of any one of embodiments P122 to P137, wherein the protease has higher specificity and higher affinity for the toxic proteins (e.g., dipeptide repeat proteins) compared to proteins normally occurring in the CSF.

Embodiment P140: The method of any one of embodiments P122 to P139, wherein the protease has higher efficiency cleaving at least one peptide bond of the toxic proteins (e.g., dipeptide repeat proteins) compared to the peptide bonds of proteins normally occurring in the CSF.

Embodiment P141: The method of any one of embodiments P122 to P140, wherein the protease is a protease naturally occurring in CSF.

Embodiment P142: The method of embodiment P141, wherein the protease is a kallikrein.

Embodiment P143: The method of embodiment P141, wherein the kallikrein is kallikrein-6 or kallikrein-5.

Embodiment P144: The method of any one of embodiments P122 to P124 and P127 to P143, wherein the protease is not selective for the degradation of toxic proteins (e.g., dipeptide repeat proteins) over other proteins normally occurring in the CSF.

Embodiment P145: The method of any one of embodiments P122 to P144 comprising a step of removing the CSF from the subject prior to contacting it with the protease and a step of reintroducing the CSF back into the subject after contacting it with the agent; or the method comprising contacting the CSF of the subject to the protease immobilized to a solid surface or support in a device implanted into the body of the subject, optionally wherein the protease or the protease immobilized to the solid surface or support is extracted and reintroduced to the implanted device during treating the subject for over an extended period of time, optionally wherein the extended period is an intermittent period of 2-12 months.

Embodiment P146: The method of embodiment P145, wherein the agent is immobilized (e.g., the agent is a protease immobilized on a solid substrate).

Embodiment P147: The method of embodiment P146, wherein the agent (e.g., the protease) is immobilized on a solid support.

Embodiment P148: The method of embodiment P147, wherein the solid support is a porous solid support.

Embodiment P149: The method of embodiment P147 or P148, wherein the agent (e.g., the protease) is attached to the solid support by covalent binding.

Embodiment P150: The method of embodiments P147 to P149, wherein the solid support is a cross-linked resin.

Embodiment P151: The method of embodiment P94, wherein the cross-linked resin is an agarose resin.

Embodiment P152: The method of embodiment P146, wherein the agent is immobilized by cross-linking to porous beads or membranes (e.g., the agent is a protease cross-linked to porous beads or membranes).

Embodiment P153: The method of embodiment P146, wherein the agent is immobilized by precipitation (e.g., as an amorphous or crystalline precipitate).

Embodiment P154: The method of embodiment P153, wherein the precipitated agent is cross-linked (e.g., to form a cross-linked amorphous or crystalline precipitate, e.g., cross-linked protease crystals, e.g., cross-linked amorphous protease precipitate).

Embodiment P155: The method of embodiment P146, wherein the agent is lyophilized to form a dry powder and the powder is placed inside a porous coating to form beads.

Embodiment P156: The method of any one of embodiments P145 to P155 further comprising a step of filtering the CSF prior to reintroducing the CSF back into the subject.

Embodiment P157: The method of any one of embodiments P104 to P144, wherein the agent is directly introduced into the CSF of the subject.

Embodiment P158: The method of any one of embodiments P1 to P40, or P104 to P144 further comprising a step of removing the CSF from the subject prior to contacting the CSF with a device (100) comprising protease immobilized on an agarose column, and a step of reintroducing the CSF back into the subject after contacting the CSF with the device (100).

Embodiment P159: The method of embodiment P158, wherein the subject is a non-human animal.

Embodiment P160: The method of any one of embodiments P1 to P40, or P104 to P144, wherein the CSF contacts a device implanted in the subject, wherein the device comprises the agent immobilized on a substrate.

Embodiment P161: The method of embodiment P160, wherein the agent is introduced into or extracted from the device by injection.

Embodiment P162: The method of embodiment P160 or P161, wherein the subject is human.

Embodiment P163: The method of any one of embodiments P42 to P50, or P146 to P154, or the composition of any one of embodiments P94-P102, wherein the agent is a protease and wherein the protease is immobilized at a concentration of about 1 mg/ml to about 10 mg/ml.

Embodiment P164: The method of embodiment P17 or P122, or the composition of embodiment P70, wherein the protease is a serine protease.

Embodiment P165: The method or composition of embodiment P164, wherein the serine protease is selected from the group consisting of trypsin, elastase and thrombin.

Embodiment P166: The method of embodiment P17 or P122, or the composition of embodiment P70, wherein the protease is an aspartic protease.

Embodiment P167: The method or composition of embodiment P166, wherein the aspartic protease is pepsin or endothiapepsin.

Embodiment P168: The method of embodiment P17 or P122, or the composition of embodiment P70, wherein the protease is not a metalloprotease.

Embodiment P169: The method of embodiment P17 or P122, or the composition of embodiment P70, wherein the protease is not a cysteine protease.

Embodiment P170: The method of embodiment P17 or P122, or the composition of embodiment P70, wherein the protease is not dependent on a non-covalently bound cofactor for its proteolytic activity.

Embodiment P171: The method of embodiment P17 or P122, or the composition of embodiment P70, wherein the protease is a microbial protease, and wherein the microbial protease is optionally endothiapepsin.

Embodiment P172: A kit comprising a suitably formulated agent capable of degrading or removing a toxic protein from the cerebrospinal fluid (CSF) of a subject.

Embodiment P173: A kit comprising a system for contacting cerebrospinal fluid (CSF) of a subject with an agent suitably formulated for degrading or removing a toxic protein from the CSF, wherein the kit optionally comprises the agent.

Embodiment P174: The kit of embodiment P172 or P173, wherein the kit further comprises instructions for treating the CSF with the agent.

Equivalents And Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. In the cases where elements are presented as lists, e.g., in Markush group format, each subgroup of the elements is also considered to be disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

The entire disclosure of the issued patents, published patent applications, journal articles, and other publications, referred to herein is incorporated by reference. If the information in the incorporated references conflicts with the instant specification, the specification shall control. Any particular embodiment of the present invention that falls within the prior art may be explicitly excluded from any one or more of the claims. As such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a neurological disorder characterized by the presence of a dipeptide repeat protein in cerebrospinal fluid (CSF), the method comprising contacting the CSF of a subject in need thereof with an effective amount of a protease capable of removing the dipeptide repeat protein, wherein the dipeptide repeat protein comprises two or more repeats of a dipeptide amino acid sequence,
wherein the protease is immobilized at a concentration of 1-10 milligrams per milliliter of the protease, the neurological disorder is selected from the group consisting of amyotrophic lateral sclerosis (ALS) and frontotemporal dementia (FTD),
wherein the protease is proteinase K.

2. The method of claim 1, wherein the dipeptide amino acid sequence is selected from the group consisting of glycine-alanine (GA), glycine-arginine (GR), alanine-proline (AP), glycine-proline (GP), and proline-arginine (PR).

3. The method of claim 1, wherein the dipeptide repeat protein is a mutant chromosome 9 open reading frame 72 (C9orf72) protein.

4. The method of claim 1, wherein the protease is contacted with the CSF in vivo.

5. The method of claim 1, wherein the protease is immobilized to a solid substrate.

6. The method of claim 5, wherein the solid substrate is selected from the group consisting of porous solid substrate and cross-linked resin.

7. The method of claim 1, further comprising the step of detecting the dipeptide repeat protein from the CSF of the subject.

8. The method of claim 7, wherein the step of detection is conducted prior to the step of contacting, thereby identifying the subject as suitable for the treatment.

9. A method of treating a neurological disorder characterized by the presence of a dipeptide repeat protein in cerebrospinal fluid (CSF), the method comprising contacting the CSF of a subject in need thereof with an effective amount of a protease capable of removing the dipeptide repeat protein, wherein the dipeptide repeat protein comprises two or more repeats of a dipeptide amino acid sequence, wherein the neurological disorder is selected from the group consisting of amyotrophic lateral sclerosis (ALS) and frontotemporal dementia (FTD), wherein the protease is proteinase K and is immobilized to an agarose substrate.

10. The method of claim 9, wherein the dipeptide amino acid sequence is selected from the group consisting of glycine-alanine (GA), glycine-arginine (GR), alanine-proline (AP), glycine-proline (GP), and proline-arginine (PR).

11. The method of claim 9, wherein the dipeptide repeat protein is a mutant chromosome 9 open reading frame 72 (C9orf72) protein.

12. The method of claim 9, wherein the protease is contacted with the CSF in vivo.

13. The method of claim 9, further comprising the step of detecting the dipeptide repeat protein from the CSF of the subject.

14. The method of claim 13, wherein the step of detection is conducted prior to the step of contacting, thereby identifying the subject as suitable for the treatment.

15. A method of treating a neurological disorder characterized by the presence of a dipeptide repeat protein in cerebrospinal fluid (CSF), the method comprising contacting the CSF of a subject in need thereof with an effective amount of a protease capable of removing the dipeptide repeat protein, wherein the dipeptide repeat protein comprises two or more repeats of a dipeptide amino acid sequence, wherein the protease is immobilized at a concentration of 1-10 milligrams per milliliter of the protease, the neurological disorder is selected from the group consisting of amyotrophic lateral sclerosis (ALS) and frontotemporal dementia (FTD), wherein the protease is proteinase K and the protease has higher specificity and higher affinity to the dipeptide repeat protein compared to a plurality of other proteins occurring in the CSF.

16. The method of claim 15, wherein the dipeptide amino acid sequence is selected from the group consisting of glycine-alanine (GA), glycine-arginine (GR), alanine-proline (AP), glycine-proline (GP), and proline-arginine (PR).

17. The method of claim 15, wherein the dipeptide repeat protein is a mutant chromosome 9 open reading frame 72 (C9orf72) protein.

18. The method of claim 15, wherein the protease is contacted with the CSF in vivo.

19. The method of claim 15, wherein the protease is immobilized to a solid substrate.

20. The method of claim 19, wherein the solid substrate is selected from the group consisting of porous solid substrate and cross-linked resin.

21. The method of claim 15, further comprising the step of detecting the dipeptide repeat protein from the CSF of the subject.

22. The method of claim 21, wherein the step of detection is conducted prior to the step of contacting, thereby identifying the subject as suitable for the treatment.

* * * * *